(12) United States Patent
Losey et al.

(10) Patent No.: US 11,980,652 B2
(45) Date of Patent: *May 14, 2024

(54) COMPOSITIONS AND METHODS FOR SUBCUTANEOUS ADMINISTRATION OF CANCER IMMUNOTHERAPY

(71) Applicant: Mural Oncology, Inc., Waltham, MA (US)

(72) Inventors: Heather C. Losey, Lexington, MA (US); Jared Lopes, Wilmington, MA (US); Lei Sun, Waltham, MA (US); Raymond J. Winquist, Marshfield, MA (US)

(73) Assignee: Mural Oncology, Inc., Waltham, MA (US)

( * ) Notice: Subject to any disclaimer, the term of this patent is extended or adjusted under 35 U.S.C. 154(b) by 35 days.

This patent is subject to a terminal disclaimer.

(21) Appl. No.: 17/568,251

(22) Filed: Jan. 4, 2022

(65) Prior Publication Data

US 2022/0241370 A1 Aug. 4, 2022

Related U.S. Application Data

(63) Continuation of application No. 16/897,920, filed on Jun. 10, 2020, now Pat. No. 11,246,906.

(60) Provisional application No. 62/932,160, filed on Nov. 7, 2019, provisional application No. 62/924,356, filed on Oct. 22, 2019, provisional application No. 62/860,182, filed on Jun. 11, 2019.

(51) Int. Cl.
| | |
|---|---|
| *A61K 38/00* | (2006.01) |
| *A61K 9/00* | (2006.01) |
| *A61K 38/16* | (2006.01) |
| *A61K 39/395* | (2006.01) |
| *A61P 35/00* | (2006.01) |
| *C07K 16/28* | (2006.01) |

(52) U.S. Cl.
CPC ............ *A61K 38/16* (2013.01); *A61K 9/0019* (2013.01); *A61K 39/3955* (2013.01); *A61P 35/00* (2018.01); *C07K 16/2818* (2013.01)

(58) Field of Classification Search
CPC ... A61K 38/16; A61K 9/0019; C07K 16/2818
See application file for complete search history.

(56) References Cited

U.S. PATENT DOCUMENTS

| | | | |
|---|---|---|---|
| 9,844,582 B2 | 12/2017 | Wittrup et al. | |
| 2013/0336924 A1 | 12/2013 | Alvarez et al. | |
| 2014/0234962 A1 | 8/2014 | Alvarez | |
| 2016/0175458 A1 | 6/2016 | Alvarez et al. | |
| 2017/0233448 A1* | 8/2017 | Malek | A61P 43/00 424/85.2 |

FOREIGN PATENT DOCUMENTS

| | | |
|---|---|---|
| WO | WO 2013184942 A1 | 12/2013 |
| WO | WO 2014170032 A1 | 10/2014 |
| WO | WO 2016100788 A1 | 6/2016 |
| WO | WO 2019094916 A1 | 5/2019 |
| WO | WO 2020249687 A1 | 12/2020 |
| WO | WO 2020249693 A1 | 12/2020 |

OTHER PUBLICATIONS

Alkermes PLC Securities and Exchange Commission Form 8-K Current report filing, Internet Citation, Jan. 7, 2019. http://pdf.secdatabase.com/1739/0001564590-19-000274.pdf.
Anonymous: "Alkermes Initiates Clinical Study of ALKS 4230 Administered Subcutaneously in Patients With Advanced Solid Tumors", News from Alkermes, May 19, 2019, XP002800274, https://www.prnewswire.com/news-releases/alkermes-initiates-clinical-study-of-alks-4230-administered-subcutaneously-in-advanced-solid-tumors-300801629.html.
Anonymous: "A Dose Escalation and Cohort Expansion Study of Subcutaneously-Administered Cytokine ALKS 4230) (Nemvaleukin Alfa) as a Single Agent and in Combination With Anti-PD-1-Antibody (Pembrolizumab) in Subjects With Select Advanced or Metastatic Solid Tumors (Artistry-2)", ClinicalTrials.gov, Dec. 2019. https://clinicaltrials.gov/ct/2/show/NCT03861793.
Charych et al., "NKTR-214, an Engineered Cytokine with Biased IL2 Receptor Binding, Increased Tumor Exposure, and Marked Efficacy in Mouse Tumor Models", *Clinical Cancer Search*, 22(3):680-690, 2016.
International Preliminary Report on Patentability for International Application No. PCT/EP2020/66234, dated Dec. 23, 2021, 14 pages.
International Preliminary Report on Patentability for International Application No. PCT/IB2020/000860, dated Apr. 28, 2022, 9 pages.
International Search Report and Written Opinion for International Application No. PCT/EP2020/066234, dated Sep. 24, 2020, 20 pages.
International Search Report and Written Opinion for International Application No. PCT/EP2020/066266, dated Sep. 30, 2020, 12 pages.
International Search Report and Written Opinion for International Application No. PCT/IB2020/000860, dated Feb. 25, 2021, 13 pages.
Lopes et al., "Ex vivo expansion and activation of human lymphocytes with a selective activator of effector cells", *Cancer Research*, vol. 75, Supplement 15, 2015. Abstract 3158. https://doi.org/10.1158/1538-7445.AM2015-3158.
Lopes et al., "Characterization of the pharmacodynamic immune response to a novel immunotherapeutic agent, ALKS 4230, in mice and non-human primates", *Cancer Research*, vol. 77, Supplement 13, Jul. 2017. Abstract 2663, https://doi.org/10.1158/1538-7445.AM2017-2663.

(Continued)

*Primary Examiner* — Jeanette M Lieb
(74) *Attorney, Agent, or Firm* — Fish & Richardson P.C.

(57) ABSTRACT

The invention provides compositions, methods and treatment regimens for treating cancer comprising periodic subcutaneous administration of the fusion protein of SEQ ID NO:1 to a cancer patient resulting in enhanced activation of CD8+ T-cells with minimal effects on regulatory T cell ($T_{reg}$) expansion and providing enhanced anti-tumor efficacy while also mitigating T cell inactivation/exhaustion.

58 Claims, 22 Drawing Sheets

Specification includes a Sequence Listing.

(56) References Cited

OTHER PUBLICATIONS

Lopes et al., "ALKS-4230: a novel engineered IL-2 fusion protein with an improved cellular selectivity profile for cancer immunotherapy", *Journal for Immunotherapy of Cancer*, vol. 8, No. 1, Apr. 2020.
Losey, et al. "Efficacy of ALKS 4230, a novel immunotherapeutic agent, in murine syngeneic tumor models alone and in combination with immune checkpoint inhibitors", *Cancer Research*, vol. 77, Supplement 13, 2017. Abstract 591. https://doi.org/10.1158/1538-7445.AM2017-591.
Pfannenstiel et al., "A novel, individualized xenograft model of cancer immunotherapy and tumor growth inhibition by ALKS 4230", *Journal for Immunotherapy of Cancer*, vol. 5, Supplement 2, Nov. 2017. Abstract P351.
Powderly, J., "Phase 1/2 study of subcutaneously administered ALKS 4230 as monotherapy and in combination with pembrolizumab in patients with advanced solid tumors: Artistry-2", *Journal for Immunotherapy of Cancer*, 2020, Abstract 373, 8(Suppl. 3): A1-A559 (A227).
Sun et al., "First-in-human dose selection for ALKS 4230, an investigational immunotherapeutic agent", *Experimental and Molecular Therapeutics*, vol. 77, Supplement 13, Jul. 2017. Abstract 4088. https://doi.org/10.1158/1538-7445.AM2017-4088.
Sun et al., "P425 Pharmacokinetics and pharmacodynamic effects of ALKS 4230, an investigational immunotherapeutic agent, in cynomolgus monkeys after intravenous and subcutaneous administration", *Journal for Immunotherapy of Cancer*, vol. 6, Supplement 1, Nov. 2018.
Vaishampayan et al. "Intravenous administration of ALKS 4230 as monotherapy and in combination with pembrolizumab in a phase I study of patients with advanced solid tumors", *Journal of Clinical Oncology*, vol. 37, Supplement 15, Abstract, May 2019.
Vaishampayan et al., "ALKS 4230, an engineered IL-2 fusion protein, in monotherapy dose-escalation and combination therapy with pembrolizumab in patients with solid tumors: Artistry-1 trial", *Journal of Immunotherapy of Cancer*, vol. 7, Supplement 1, pp. 243-244, Nov. 2019. Abstract P447. https://doi.org/10.1186/S40425-019-0763-1.
Wang et al., "Structure of the Quaternary Complex of Interleukin-2 with Its, and $\alpha$, $\beta$ and $\gamma_c$ Receptors", *Science*, 310:1159-1163, 2005.
Vaishampayan et al., "Safety, pharmacokinetics and pharmacodynamic effects of ALKS 4230 in patients with advanced solid tumors from the ongoing dose escalation of a first in human (FIH) study", *Journal for Immuno Therapy of Cancer* 6(Suppl1):P423 (2018).

\* cited by examiner

US 11,980,652 B2

COMPOSITIONS AND METHODS FOR SUBCUTANEOUS ADMINISTRATION OF CANCER IMMUNOTHERAPY

RELATED APPLICATIONS

This application is a continuation of U.S. patent application Ser. No. 16/897,920, filed Jun. 10, 2020, which claims the benefit of U.S. Provisional Application Nos. 62/860,182, filed Jun. 11, 2019; 62/932,160, filed Nov. 7, 2019; and 62/924,356, filed Oct. 22, 2019. The entire teachings of the above applications are incorporated herein by reference.

BACKGROUND OF THE INVENTION

The fusion protein of SEQ ID NO: 1 is a human interleukin-2 (IL-2) variant fusion protein designed for selective binding of the intermediate-affinity interleukin-2 (IL-2) receptor, IL-2Rβγ. The selectivity of the fusion protein of SEQ ID NO: 1 is achieved through the stable fusion of circularly permuted (cp) IL-2 fused to the IL-2Rα chain (CD25) of the IL-2 receptor.

The fusion protein of SEQ ID NO: 1 has advantages over native IL-2 as a therapeutic in that its selective targeting and activation of IL-2Rβγ results in the selective activation of subsets of CD8+ T cells and NK cells, which can drive anti-tumor immune responses. The administration of the fusion protein of SEQ ID NO:1 is beneficial to cancer patients as it reduces the immune suppressing effects of CD4+ regulatory T-cells ($T_{regs}$), while increasing CD8+ memory T-cells, thereby recruiting the patient's own immune system to eliminate cancer cells. The fusion protein of SEQ ID NO: 1 also exhibits lasting effects following administration, thereby further improving the patient's response to the treatment.

Fusion proteins are often given by intravenous (IV) administration so that the formulation is directly available in the blood stream. It would however be advantageous if a medicament could be given subcutaneously. Subcutaneous administration is a minimally invasive mode of administration. The convenience and speed of subcutaneous delivery allows increased patient compliance and quicker access to medication when needed. Subcutaneous (SC) administration is also the most versatile mode of administration that can be used for short term and long-term therapies. Subcutaneous administration can be performed by injection or by implantation of a sustained or timed-release device beneath the surface of the skin. The site of the injection or device can be rotated when multiple injections or devices are needed. Subcutaneous formulations are usually much easier to handle for the patient, especially since the drug treatment may have to be taken regularly during the patient's life.

Subcutaneous administration of certain proteins has been shown to provide a lower Cmax with a longer Tmax compared to IV administration while providing pharmacodynamic effects that are comparable between the two routes of administration. It would be desirable if subcutaneous formulations and treatment regimens of the fusion protein of SEQ ID NO: 1 could be identified that are equal to, or even surpass the pharmacokinetics (PK) and pharmacodynamics (PD), tolerability profiles and immunogenicity profiles as compared to IV delivery of the fusion protein of SEQ ID NO: 1.

SUMMARY OF THE INVENTION

The invention provides compositions, methods and treatment regimens for periodic subcutaneous administration of the fusion protein of SEQ ID NO: 1 in accordance with the invention providing certain advantages for delivering the fusion protein of SEQ ID NO: 1 to a patient in need of cancer treatment as compared to daily SC or IV delivery of SEQ ID NO: 1. It has been unexpectedly discovered that periodic SC administration of the fusion protein of SEQ ID NO: 1 also provides enhanced activation of CD8+ T-cells with minimal effects on regulatory T cell expansion resulting in enhanced anti-tumor activity while also mitigating T cell inactivation/exhaustion.

Accordingly, the invention provides a method of treating cancer in a patient comprising periodically subcutaneously administering to the patient a dose of the fusion protein of SEQ ID NO: 1 wherein the periodic dosing is once every about 3 days to once every about 60 days. Preferably the periodic dosing is once every about 3 days to once every about 21 days. Preferably, the periodic dosing is once every 3 days, once every 4 days, once every 7 days, once every 14 days or once every 21 days.

Preferably, the invention provides pharmaceutical compositions for subcutaneous administration comprising a dose of the fusion protein of SEQ ID NO: 1 of about 0.1 mg to about 30 mg. Preferably, the invention provides pharmaceutical compositions for subcutaneous administration comprising a dose of the fusion protein of SEQ ID NO: 1 of: about 0.1 mg to about 30 mg; about 0.3 mg to about 30 mg; about 0.3 mg to about 25 mg; about 0.3 mg to about 20 mg; about 0.3 mg to about 15 mg; about 0.3 mg to about 10 mg; about 0.3 mg to about 3 mg; about 0.3 mg to about 1 mg; about 1 mg to about 30 mg; about 1 mg to about 25 mg; about 1 mg to about 20 mg; about 1 mg to about 15 mg; about 1 mg to about 10 mg; about 1 mg to about 3 mg; about 3 mg to about 30 mg; about 3 mg to about 25 mg; about 3 mg to about 20 mg; about 3 mg to about 15 mg; about 3 mg to about 10 mg; about 10 mg to about 30 mg; about 10 mg to about 25 mg; about 10 mg to about 20 mg; or about 10 mg to about 15 mg.

Preferably, the dose of SEQ ID NO: 1 for subcutaneous administration is expressed in terms of µg/kg as is often preferred for calculating dose based on the weight of a pediatric patient but is also useful for calculating dose based on the weight of an adult. Preferred doses of SEQ ID NO: 1 for subcutaneous administration in terms of µg/kg range from: about 1 µg/kg to about 500 µg/kg; about 1 µg/kg to about 250 µg/kg; about 1 µg/kg to about 100 µg/kg; about 1 µg/kg to about 50 µg/kg; about 1 µg/kg to about 25 µg/kg; about 1 µg/kg to about 15 µg/kg; about 1 µg/kg to about 10 µg/kg; about 1 µg/kg to about 5 µg/kg; about 5 µg/kg to about 500 µg/kg; about 5 µg/kg to about 250 µg/kg; about 5 µg/kg to about 100 µg/kg; about 5 µg/kg to about 50 µg/kg; about 5 µg/kg to about 25 µg/kg; about 5 µg/kg to about 15 µg/kg; about 5 µg/kg to about 10 µg/kg; about 15 µg/kg to about 500 µg/kg; about 15 µg/kg to about 250 µg/kg; about 15 µg/kg to about 100 µg/kg; about 15 µg/kg to about 50 µg/kg; about 15 µg/kg to about 25 µg/kg; about 50 µg/kg to about 500 µg/kg; about 50 µg/kg to about 250 µg/kg; about 50 µg/kg to about 100 µg/kg; about 150 µg/kg to about 500 µg/kg; about 150 µg/kg to about 250 µg/kg; about 200 µg/kg to about 500 µg/kg; about 250 µg/kg to about 350 µg/kg; about 300 µg/kg to about 500 µg/kg; about 300 µg/kg to about 400 µg/kg; about 400 µg/kg to about 500 µg/kg or a corresponding fixed dose thereof based on, for example, a 60-70 kg adult or a corresponding fixed dose based on a child, for example, a child of about 12 kg to about 50 kg or more.

Preferably the subcutaneous dose of SEQ ID NO: 1 in terms of µg/kg is about 5 µg/kg; about 16 µg/kg; about 50 µg/kg; or about 500 µg/kg or a corresponding fixed dose thereof based on, for example, a 60-70 kg adult or a corresponding fixed dose based on a child, for example, a child of about 12 kg to about 50 kg or more.

Preferably, the periodic subcutaneous administration results in a greater CD8+ T cell expansion as compared to daily subcutaneous administration. Preferably, periodic subcutaneous dosing results in a greater ratio of CD8+ T cells to $T_{regs}$ as compared to daily subcutaneous administration. Preferably the increase in circulating CD8+ T cells is at least 2-fold over baseline prior to periodic subcutaneous administration of the fusion protein of SEQ ID NO: 1 to the patient. Preferably the cancer being treated is renal cell carcinoma (RCC), lymphomas, melanoma, hepatic cell carcinoma (HCC), non-small cell lung cancer (NSCLC), small cell lung cancer (SCLC), squamous cell carcinoma of the head and neck (SCCHN) breast cancer, pancreatic cancer, prostate cancer, colon and rectal cancer, bladder cancer, cervical cancer, thyroid cancer, esophageal cancer, oral cancer, mesothelioma, and non-melanoma skin cancer. Preferably wherein the patient has a lower risk of T cell exhaustion. Preferably, the patient has a lower risk of capillary leak syndrome (CLS) or cytokine release syndrome (CRS). Preferably the patient has a lower risk of weight loss. Preferably further comprising co-administering to the patient a therapeutically effective amount of a therapeutic agent. Preferably the therapeutic agent is a PARP inhibitor, an immune checkpoint protein inhibitor a cytotoxic agent or a chemotherapeutic agent. Preferably the therapeutic agent is an immune checkpoint protein inhibitor. Preferably the immune checkpoint inhibitor inhibits the interaction of PD-1 and PD-L1. Preferably wherein the immune checkpoint inhibitor is pembrolizumab. Preferably the ratio of increase in IFNγ present in a patient's peripheral blood, serum or plasma resulting from subcutaneous administration is at least about 2-fold greater as compared to intravenous administration of an equivalent dose. Preferably the ratio of increase in IFNγ present in a patient's peripheral blood, serum or plasma resulting from subcutaneous administration is at least about 5-fold greater as compared to intravenous administration of an equivalent dose. Preferably the ratio of increase in IFNγ present in a patient's peripheral blood, serum or plasma when resulting from subcutaneous administration is at least about 7-fold greater as compared to intravenous administration normalized for the same dose. Preferably the ratio of increase in IL-6 present in a patient's peripheral blood, serum or plasma when resulting from subcutaneous administration is at least about 2-fold less as compared to intravenous administration of an equivalent dose. Preferably the cancer being treated is a solid tumor. Preferably, the solid tumor is a carcinoma, sarcoma or lymphoma. Preferably, the cancer being treated is a blood cancer. Preferably, wherein the blood cancer is leukemia, non-Hodgkin lymphoma, Hodgkin lymphoma and multiple myeloma. Preferably, the pembrolizumab is co-administered prior to, simultaneously with, or subsequent to, administration of the fusion protein of SEQ ID NO:1. Preferably, the pembrolizumab is co-administered in a separate composition from the fusion protein of SEQ ID NO: 1. Preferably pembrolizumab is administered in an amount of 200 mg by I.V. injection or infusion. Preferably pembrolizumab is administered on the first day of administration of the fusion protein of SEQ ID NO: 1. Preferably pembrolizumab is administered about once a week. Preferably pembrolizumab is administered about once every 3 weeks. Preferably the dose is provided as a pharmaceutical composition formulated for subcutaneous administration. Preferably, the pharmaceutical composition is a stable aqueous solution ready for administration. Preferably the pharmaceutical composition is lyophilized. Preferably the pharmaceutical composition is reconstituted with a pharmaceutically acceptable vehicle suitable for injection. Preferably the pharmaceutical composition comprises a dose of about 1 mg to about 30 mgs of the fusion protein of SEQ ID NO: 1. Preferably the pharmaceutical composition comprises a dose of about 1 mg, 3 mg, 10 mg or 30 mg of the fusion protein of SEQ ID NO: 1. Preferably the fusion protein is a variant of the fusion protein of SEQ ID NO: 1 comprising an amino acid sequence having at least about 75%, at least about 80%, at least about 85%, at least about 90%, at least about 95%, at least about 98%, or at least about 99%, amino acid sequence identity to a contiguous stretch of SEQ ID NO: 1 of at least 20 amino acids up to the full length of SEQ ID NO: 1.

DETAILED DESCRIPTION OF THE INVENTION

Definitions

Figure 1:
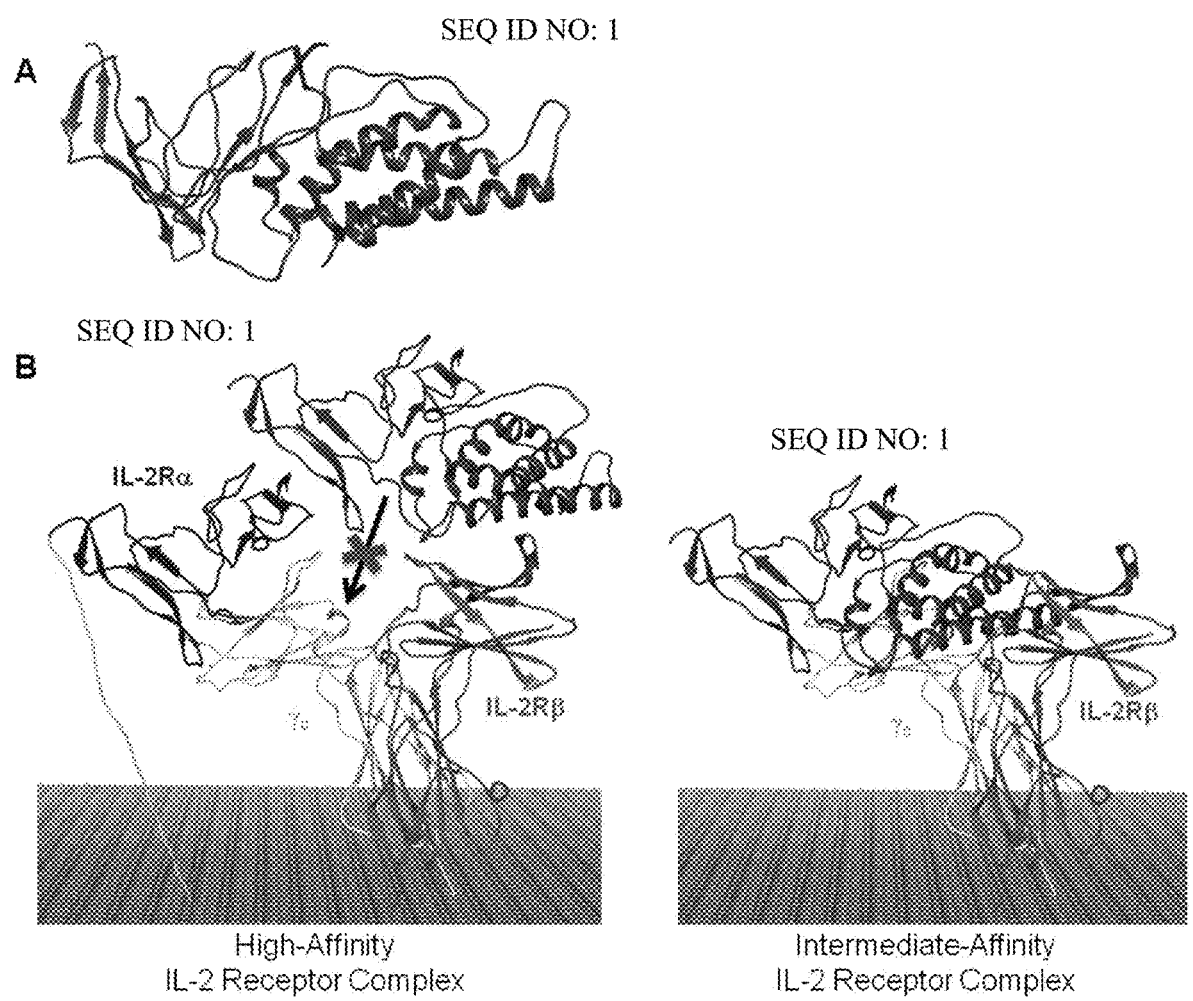
FIG. 1 shows diagrams of structural models of the fusion protein of SEQ ID NO: 1 (panel A) and its selective binding intermediate-affinity IL-2 receptor (panel B). The structural models in panels A and B were generated using the experimentally determined crystal structure of the quaternary complex of human IL-2 bound to the trimeric high-affinity receptor (Wang et al., Science. 2005; 310(5751):1159-1163. doi: 10.1126/science.1117893).

Those skilled in the art will recognize or be able to ascertain using no more than routine experimentation, many equivalents to the specific embodiments in accordance with the invention described herein. The scope of the present invention is not intended to be limited to the following description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

As used herein, the term "about" or "approximately" as applied to one or more values of interest, refers to a value that is similar to a stated reference value. In certain embodiments, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The term "pharmaceutically acceptable" preferably means approved or approvable by a regulatory agency of the Federal or a state government or the corresponding agency in countries other than the United States, or that is listed in the U.S. Pharmacopoeia or other generally recognized pharmacopoeia, for use in animals, and more particularly, in humans.

The term "protein" or "peptide" as used herein refers to a at least two or more amino acid residues linked together by peptide bond. The amino acid sequence in a protein or peptide is shown in the standard format, i.e., from amino terminus (N-terminus) to carboxyl terminus (C-terminus).

The term "fusion protein" designates a protein or peptide linked together with another protein or peptide by peptide bond between their respective N- and C-terminal amino acid residues or verse visa, or by insertion of the first protein or peptide into the internal region of the second protein or peptide by two peptide bonds at the N- and C-termini of the inserted protein or peptide. A peptide bond is a covalent chemical bond formed between carboxyl group of one amino acid and the amine group of another amino acid. A fusion protein is produced by expression of the fusion protein gene in an expression host, in which the coding sequence for the first protein or peptide is linked to the coding sequence of the second protein or peptide.

The "fusion protein of SEQ ID NO: 1" is also referred to herein as "cpIL-2:IL-2Rα" and is described in PCT application publication number, WO 2013/184942. The fusion protein of SEQ ID NO: 1 is a circularly permuted (cp) IL-2 variant fused to the extracellular domain of the IL-2Rα portion of the IL-2 receptor and has the following amino acid sequence:

(SEQ ID NO: 1)
SKNFHLRPRDLISNINVIVLELKGSETTFMCEYAD

ETATIVEFLNRWITFSQSIISTLTGGSSSTKKTQL

QLEHLLLDLQMILNGINNYKNPKLTRMLTFKFYMP

```
            -continued
KKATELKHLQCLEEELKPLEEVLNLAQGSGGGSEL

CDDDPPEIPHATFKAMAYKEGTMLNCECKRGFRRI

KSGSLYMLCTGNSSHSSWDNQCQCTSSATRNTTKQ

VTPQPEEQKERKTTEMQSPMQPVDQASLPGHCREP

PPWENEATERIYHFVVGQMVYYQCVQGYRALHRGP

AESVCKMTHGKTRWTQPQLICTG.
```

The invention also contemplates the use of a variant of the fusion protein of SEQ ID NO: 1 having an amino acid sequence having sequence identity that is about 75%, 80%, 85%, 90%, 91%, 92%, 93%, 94%, 95%, 96%, 97%, 98%, 99% or higher over a contiguous stretch of about 20 amino acids up to the full length of SEQ ID NO: 1. A variant of the SEQ ID NO: 1 may have a defined sequence identity as compared to SEQ ID NO: 1 over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a variant of the fusion protein of SEQ ID NO: 1 can comprise an amino acid sequence having at least about 75%, at least about 80%, at least about 85%, at least about 90%, at least about 95%, at least about 98%, or at least about 99%, amino acid sequence identity to a contiguous stretch of SEQ ID NO: 1 of at least 20 amino acids and preferably from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length of SEQ ID NO: 1.

The term "IL-2 therapy" includes administration of immunotherapy based on IL-2 and its associated biological functions as an immunotherapy including but not limited to maintenance of CD4+ regulatory T cells and differentiation of CD4+ T cells into a variety of subsets; promotion of CD8+ T-cell and NK cell cytotoxicity activity, and modulation of T-cell differentiation programs in response to antigen, promoting naive CD4+ T-cell differentiation into T helper-1 (Th1) and T helper-2 (Th2) cells while inhibiting T helper-17 (Th17) differentiation. Therefore "IL-2 therapy" as used herein includes but is not limited to immunotherapy with rhIL-2 or a variant of rhIL-2 such as the Fusion Protein of SEQ ID NO: 1.

The terms "high dose IL-2" and "HD IL-2" include a dose of interleukin-2 (IL-2) of about or at least about 600,000 International Units (IU)/kg of body weight (kg)/dose, or about or at least about 720,000 IU/kg/dose.

The terms "low dose IL-2" and "LD IL-2" include a dose of interleukin-2 (IL-2) of less than about 600,000 IU/kg of body weight/dose, such as about 60,000 or about 72,000 IU/kg/dose, e.g., from about 60,000 to about 72,000 IU/kg/dose.

As used herein, the term "subject" or "patient" refers to any organism to which a composition in accordance with the present disclosure may be administered, e.g., for experimental, diagnostic, prophylactic, and/or therapeutic purposes. Typical subjects include animals (e.g., mammals such as mice, rats, rabbits, non-human primates, and humans) and/or plants. Preferably "patient" refers to a human subject who may seek or be in need of treatment, requires treatment, is receiving treatment, will receive treatment, or a subject who is under care by a trained professional for a particular disease or condition. The "patient" can be a child (>1-17 years). In still other embodiments, the patient can be an infant (1 year and younger). In yet still other embodiments, the patient can be a pediatric patient, wherein the term "pediatric" is used as understood by those skilled in the art. For example, pediatric patients include infants, children and adolescents.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable excipient" refers to a diluent, adjuvant, excipient or carrier with which a compound of the disclosure is administered. A pharmaceutically acceptable excipient is generally a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include water, any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this present disclosure.

The term "recombinant production" refers to the techniques for manipulating and combining two or more DNA sequences together that include recombination, PCR (polymerase chain reaction), in vitro mutagenesis, and direct DNA synthesis. These techniques are described in numerous published books and manuals, including the "Current protocols in molecular biology" (Ausubel eds. 2008. John Wiley & Son).

As used herein any form of administration or coadministration of a "combination", "combined therapy" and/or "combined treatment regimen" refers to at least two therapeutically active agents which may be administered or co-administered", simultaneously, in either separate or combined formulations, or sequentially at different times separated by minutes, hours or days. In general, each agent will be administered at a dose and/or on a time schedule determined for that agent.

As used herein, the term "parenteral" refers to dosage forms that are intended for administration as an injection or infusion and includes subcutaneous, intravenous, intra-arterial, intraperitoneal, intracardiac, intrathecal, and intramuscular injection, as well as infusion injections usually by the intravenous route.

The term "therapeutic agent" encompasses any agent administered to treat a symptom or disease in an individual in need of such treatment in addition to, or in combination with, SEQ ID NO: 1. Such additional therapeutic agent may comprise any active ingredients suitable for the particular indication being treated, preferably those with complementary activities that do not adversely affect each other. Preferably, an additional therapeutic agent is an anti-inflammatory agent.

The term "chemotherapeutic agent" refers to a compound or a derivative thereof that can interact with a cancer cell, thereby reducing the proliferative status of the cell and/or killing the cell for example, by impairing cell division or DNA synthesis, or by damaging DNA, effectively targeting fast dividing cells. Examples of chemotherapeutic agents include, but are not limited to, alkylating agents (e.g., cyclophosphamide, ifosfamide); metabolic antagonists (e.g., methotrexate (MTX), 5-fluorouracil or derivatives thereof); a substituted nucleotide; a substituted nucleoside; DNA demethylating agents (also known as antimetabolites; e.g., azacitidine); antitumor antibiotics (e.g., mitomycin, adriamycin); plant-derived antitumor agents (e.g., vincristine, vindesine, TAXOL®, paclitaxel, abraxane); cisplatin; carboplatin; etoposide; and the like. Such agents may further include, but are not limited to, the anti-cancer agents trimethotrexate (TMTX); temozolomide; raltitrexed; S-(4-Nitrobenzyl)-6-thioinosine (NBMPR); 6-benzyguanidine (6-BG); a nitrosoureas a nitrosourea (rabinopyranosyl-N-methyl-N-nitrosourea (Aranose), Carmustine (BCNU, BiCNU), Chlorozotocin, Ethylnitrosourea (ENU), Fotemustine, Lomustine (CCNU), Nimustine, N-Nitroso-N-methylurea (NMU), Ranimustine (MCNU), Semustine, Streptozocin (Streptozotocin)); cytarabine; and camptothecin; or a therapeutic derivative of any thereof.

The phrase "therapeutically effective amount" or an "effective amount refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration can be indicative of whether a therapeutically effective amount has been used. In reference to cancer or pathologies related to unregulated cell division, a therapeutically effective amount refers to that amount which has the effect of (1) reducing the size of a tumor (i.e. tumor regression), (2) inhibiting (that is, slowing to some extent, preferably stopping) aberrant cell division, for example cancer cell division, (3) preventing or reducing the metastasis of cancer cells, and/or, (4) relieving to some extent (or, preferably, eliminating) one or more symptoms associated with a pathology related to or caused in part by unregulated or aberrant cellular division, including for example, cancer.

An "effective amount" is also that amount that results in desirable PD and PK profiles and desirable immune cell profiling upon administration of the therapeutically active compositions of the invention.

The terms "treating" or "treatment" of a disease (or a condition or a disorder) as used herein refer to preventing the disease from occurring in a human subject or an animal subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and causing regression of the disease. The terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance. With regard to cancer, these terms also mean that the life expectancy of an individual affected with a cancer may be increased or that one or more of the symptoms of the disease will be reduced. With regard to cancer, "treating" also includes enhancing or prolonging an anti-tumor response in a subject.

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

"Progression free survival (PFS)," as used in the context of the cancers described herein, refers to the length of time during and after treatment of the cancer until objective tumor progression or death of the patient. The treatment may be assessed by objective or subjective parameters; including the results of a physical examination, neurological examination, or psychiatric evaluation. In preferred aspects, PFS may be assessed by blinded imaging central review and may further optionally be confirmed by ORR or by blinded independent central review (BICR).

"Overall survival (OS)" may be assessed by OS rate at certain time points (e.g., 1 year and 2 years) by the Kaplan-Meier method and corresponding 95% CI will be derived based on Greenwood formula by study treatment for each tumor type. OS rate is defined as the proportion of participants who are alive at the time point. OS for a participant is defined as the time from the first dosing date to the date of death due to any cause.

As used herein a "complete response" (CR) is the disappearance of all signs of cancer in response to treatment. A complete response may also be referred to herein as "total remission".

As used herein the term "partial response" (PR) means a decrease in the size of the tumor, or in the extent of cancer in the body in response to treatment. A partial response may also be referred to herein as "partial remission".

The term "cancer", as used herein, shall be given its ordinary meaning, as a general term for diseases in which abnormal cells divide without control.

The term "reducing a tumor" or "tumor regression" as used herein refers to a reduction in the size or volume of a tumor mass, a decrease in the number of metastasized tumors in a subject, a decrease in the proliferative status (the degree to which the cancer cells are multiplying) of the cancer cells, and the like.

The term "enhancing", as used herein, refers to allowing a subject or tumor cell to improve its ability to respond to a treatment disclosed herein. For example, an enhanced response may comprise an increase in responsiveness of at least 5%, 10%, 15%, 20%, 25%, 30%, 35%, 40%, 45%, 50%, 55%, 60%, 65%, 70%, 75%, 80%, 85%, 90%, 95% or 98% or more. As used herein, "enhancing" can also refer to enhancing the number of subjects who respond to a treatment such as a combination therapy comprising chemotherapy, drug-resistant immunocompetent cells, and immune checkpoint inhibitors. For example, an enhanced response may refer to a total percentage of subjects who respond to a treatment wherein the percentage is of at least 5%, 10%, 15%, 20%, 25%, 30%, 35%, 40%, 45%, 50%, 55%, 60%, 65%, 70%, 75%, 80%, 85%, 90%, 95% or 98% or more.

"Immune checkpoint proteins" regulate T cell function in the immune system. T cells play a central role in cell-mediated immunity. Immune checkpoint proteins interact with specific ligands that send a signal into the T cell and essentially switch off or inhibit T cell function. Cancer cells take advantage of this system by driving high levels of expression of immune checkpoint proteins on their surface that results in control of the T cells expressing immune checkpoint proteins on the surface of T cells that enter the tumor microenvironment, thus suppressing the anticancer immune response. As such, inhibition of immune checkpoint proteins by agents referred to herein as "immune checkpoint inhibitors" or "checkpoint inhibitors" would result in restoration of T cell function and an immune response to the cancer cells. Examples of immune checkpoint proteins include, but are not limited to: CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, OX40, B-7 family ligands or a combination thereof. Preferably, the immune checkpoint inhibitor interacts with a ligand of a immune checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, OX40, A2aR, B-7 family ligands or a combination thereof. Examples of immune checkpoint inhibitors include but are not limited to: from a PD-1 antagonist, PD-L1 antagonist, CTLA-4 antagonist, adenosine A2A receptor antagonist, B7-H3 antagonist, B7-114 antagonist, BTLA antagonist, KIR antagonist, LAG3 antagonist, TIM-3 antagonist, VISTA antagonist or TIGIT antagonist.

Fusion Protein of SEQ ID NO: 1

A recombinant human IL-2 variant fusion protein, described in WO 2013/184942, is a circularly permuted (cp) IL-2 variant fused to the extracellular domain of the IL-2Rα portion of the IL-2 receptor and is referred to herein as the "fusion protein of SEQ ID NO: 1" or has the following amino acid sequence:

```
                                    (SEQ ID NO: 1)
SKNFHLRPRDLISNINVIVLELKGSETTFMCEYAD

ETATIVEFLNRWITFSQSIISTLTGGSSSTKKTQL
```

-continued
```
QLEHLLLDLQMILNGINNYKNPKLTRMLTFKFYMP

KKATELKHLQCLEEELKPLEEVLNLAQGSGGGSEL

CDDDPPEIPHATFKAMAYKEGTMLNCECKRGFRRI

KSGSLYMLCTGNSSHSSWDNQCQCTSSATRNTTKQ

VTPQPEEQKERKTTEMQSPMQPVDQASLPGHCREP

PPWENEATERIYHFVVGQMVYYQCVQGYRALHRGP

AESVCKMTHGKTRWTQPQLICTG.
```

It is contemplated that fusion proteins that are closely related to SEQ ID NO: 1, such as those fusion proteins having sequence identities of about 80%, 85%, 90%, 91%, 92%, 93%, 94%, 95%, 96%, 97%, 98%, 99% or higher identity over a contiguous sequence of at least about 20 amino acids up to the full length of SEQ ID NO: 1 may also be suitable for administration in accordance with the methods of the invention.

The fusion protein of SEQ ID NO: 1 (FIG. 1, Panel A) is designed to selectively bind to and activate the intermediate-affinity IL-2R (FIG. 1, Panel B), but not the high-affinity IL-2R (FIG. 1, Panel B). The IL-2Rα domain of the fusion protein of SEQ ID NO: 1 serves to sterically impede the binding of the fusion protein of SEQ ID NO: 1 to the high-affinity IL-2R yet still allow binding to the intermediate-affinity IL-2R.

In vitro and in vivo nonclinical pharmacodynamic (PD) data support selective signaling through the intermediate-affinity IL-2 receptor by the fusion protein of SEQ ID NO: 1, leading to the selective activation and expansion of effector cells such as NK cells and CD8+ T cells, while minimizing the activation and expansion of immunosuppressive regulatory T cells ($T_{regs}$). Additionally, in vivo in mice, the mouse surrogate of fusion protein of SEQ ID NO: 1 displays improved tolerability relative to rhIL-2 at doses that elicit equivalent or greater expansion of effector cells relative to $T_{regs}$.

First in human clinical data described in U.S. Patent Application Ser. No. 62/860,182 indicates that the fusion protein of SEQ ID NO: 1 activates expansion of CD8+ T-cells and NK cells in a dose dependent manner with minimal non-dose-dependent activation of $T_{regs}$ (i.e. in the absence of dose dependent activation of $T_{regs}$). Therefore, the fusion protein of SEQ ID NO: 1 can be dosed in human patients at a concentration that is comparative to high dose rhIL-2 to elicit equivalent or greater expansion of NK cells and CD8+ T cells as compared to, for example, high dose rhIL-2 but with far less (at least two fold less) relative expansion of immunosuppressive $T_{regs}$ as compared to high dose rhIL-2 (Table 2).

Non-clinical and human clinical data described in the Examples infra demonstrates that, for example, periodic subcutaneous dosing of the fusion protein of SEQ ID NO: 1 avoids both T cell exhaustion and the potential for regulatory CD4+ T-cell populations to overwhelm the cytotoxic actions of CD8+ T cells.

Pharmaceutical Compositions

The fusion protein of SEQ ID NO: 1 is preferably formulated for subcutaneous administration via injection to a patient. In general, such compositions are "pharmaceutical compositions" comprising the fusion protein of SEQ ID NO: 1 and one or more pharmaceutically acceptable or physiologically acceptable diluents, carriers or excipients.

The pharmaceutical compositions of the invention are formulated to be compatible with the subcutaneous administration. The pharmaceutical compositions may be also be formulated to suitable for administration in combination with other therapeutically active agents or compounds as described herein in order to treat or prevent the diseases, disorders and conditions as contemplated by the present disclosure.

The pharmaceutical compositions for subcutaneous administration typically comprise a therapeutically effective amount of the fusion protein of SEQ ID NO: 1 and one or more pharmaceutically and physiologically acceptable formulation agents.

After a pharmaceutical composition has been formulated for subcutaneous administration, it can preferably be stored in sterile vials as a solution, suspension, gel, emulsion, solid, or dehydrated or lyophilized powder. Such formulations can be stored either in a ready-to-use form, a lyophilized form requiring reconstitution prior to use, a liquid form requiring dilution prior to use, or other acceptable form.

Preferably, the pharmaceutical composition is provided in a single-use container (e.g., a single-use vial, ampoule, syringe, or autoinjector whereas a multi-use container (e.g., a multi-use vial) is provided in other embodiments. Any drug delivery apparatus can be used to deliver the pharmaceutical composition, including implants (e.g., implantable pumps) and catheter systems, slow injection pumps and devices, all of which are well known to the skilled artisan. Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions can be in the form of a sterile injectable aqueous or oily suspension. This suspension can be formulated according to the known art using those suitable dispersing or wetting agents and suspending agents mentioned herein. The sterile injectable preparation can also be a sterile injectable solution or suspension in a non-toxic parenterally-acceptable diluent or solvent. Acceptable diluents, solvents and dispersion media that can be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. Any bland fixed oil can be employed, including synthetic mono- or diglycerides. Fatty acids such as oleic acid, find use in the preparation of injectables. Prolonged absorption of particular injectable formulations can be achieved by including an agent that delays absorption (e.g., aluminum monostearate or gelatin).

The concentration of a fusion protein of SEQ ID NO: 1 in a formulation for subcutaneous delivery can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Preferably, the invention provides pharmaceutical compositions for subcutaneous administration comprising a dose of the fusion protein of SEQ ID NO: 1 of: about 0.1 mg to about 30 mg; about 0.3 mg to about 30 mg; about 0.3 mg to about 25 mg; about 0.3 mg to about 20 mg; about 0.3 mg to about 15 mg; about 0.3 mg to about 10 mg; about 0.3 mg to about 3 mg; about 0.3 mg to about 1 mg; about 1 mg to about 30 mg; about 1 mg to about 25 mg; about 1 mg to about 20 mg; about 1 mg to about 15 mg; about 1 mg to about 10 mg; about 1 mg to about 3 mg; about 3 mg to about 30 mg; about 3 mg to about 25 mg; about 3 mg to about 20 mg; about 3 mg to about 15 mg; about 3 mg to about 10 mg; about 10 mg to about 30 mg; about 10 mg to about 25 mg; about 10 mg to about 20 mg; or about 10 mg to about 15 mg.

Preferably, the invention provides pharmaceutical compositions for subcutaneous administration comprising a dose of the fusion protein of SEQ ID NO: 1 of at least about 0.1 mg, 0.2 mg, 0.3 mg, 0.4 mg, 0.5 mg, 0.6 mg, 0.5 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg or 30 mg. The pharmaceutical compositions of the invention may optionally include a pharmaceutically acceptable excipient.

Preferably, the invention provides pharmaceutical compositions for subcutaneous administration comprising a dose of the fusion protein of SEQ ID NO: 1 in terms of µg/kg as is often preferred for calculating dose in pediatric patients but is also useful for calculating dose for adults, preferably at a dose of: about 1 µg/kg to about 500 µg/kg; about 1 µg/kg to about 250 µg/kg; about 1 µg/kg to about 100 µg/kg; about 1 µg/kg to about 50 µg/kg; about 1 µg/kg to about 25 µg/kg; about 1 µg/kg to about 15 µg/kg; about 1 µg/kg to about 10 µg/kg; about 1 µg/kg to about 5 µg/kg; about 5 µg/kg to about 500 µg/kg; about 5 µg/kg to about 250 µg/kg; about 5 µg/kg to about 100 µg/kg; about 5 µg/kg to about 50 µg/kg; about 5 µg/kg to about 25 µg/kg; about 5 µg/kg to about 15 µg/kg; about 5 µg/kg to about 10 µg/kg; about 15 µg/kg to about 500 µg/kg; about 15 µg/kg to about 250 µg/kg; about 15 µg/kg to about 100 µg/kg; about 15 µg/kg to about 50 µg/kg; about 15 µg/kg to about 25 µg/kg; about 50 µg/kg to about 500 µg/kg; about 50 µg/kg to about 250 µg/kg; about 50 µg/kg to about 100 µg/kg; about 150 µg/kg to about 500 µg/kg; about 150 µg/kg to about 250 µg/kg; about 200 µg/kg to about 500 µg/kg; about 250 µg/kg to about 350 µg/kg; about 300 µg/kg to about 500 µg/kg; about 300 µg/kg to about 400 µg/kg; about 400 µg/kg to about 500 µg/kg or a corresponding fixed dose thereof based on, for example, a 60-70 kg adult or a corresponding fixed dose based on a child, for example, a child of about 12 kg to about 50 kg or more.

Subcutaneous Dosing Regimens

The periodic subcutaneous (SC) route of administration of the fusion protein of SEQ ID NO: 1 is expected to produce a lower maximum drug concentration in serum with a prolonged exposure profile as compared to the intravenous (IV) route of administration and may therefore result in improved tolerability compared with the IV route of administration. Additionally, the SC route of administration is expected to facilitate direct delivery to the lymph nodes, which may provide enhanced immunological effects relative to IV dosing. A periodic SC dosing schedule (i.e., q3d, q4d, q7d, q14d or q21d) may provide a more convenient alternative to daily SC or IV dosing.

It has been discovered that periodic subcutaneous administration of the fusion protein of SEQ ID NO: 1 results in greater expansion of circulating CD8$^+$ T cells compared to daily subcutaneous dosing regimen (e.g. qdx5) with minimal differences in T$_{regs}$ resulting in greater anti-tumor efficacy and minimal T cell exhaustion.

Preferably the fusion protein of SEQ ID NO: 1 is periodically administered once every about 3 days (q3d) to once every about 60 days (q60d), preferably once every 3 days (q3d) to once every about 21 days (q21d), and preferably once every 4 days (q4d), once every 7 days (q7d), once every 14 days (q14d) or once every 21 days (q21d).

Preferably the fusion protein of SEQ ID NO: 1 is subcutaneously administered at doses of about 0.1 to 30 mgs. Preferably the fusion protein of SEQ ID NO: 1 is subcutaneously administered at doses of: about 0.1 mg to about 30 mg; about 0.3 mg to about 30 mg; about 0.3 mg to about 25 mg; about 0.3 mg to about 20 mg; about 0.3 mg to about 15 mg; about 0.3 mg to about 10 mg; about 0.3 mg to about 3 mg; about 0.3 mg to about 1 mg; about 1 mg to about 30 mg; about 1 mg to about 25 mg; about 1 mg to about 20 mg; about 1 mg to about 15 mg; about 1 mg to about 10 mg; about 1 mg to about 3 mg; about 3 mg to about 30 mg; about 3 mg to about 25 mg; about 3 mg to about 20 mg; about 3 mg to about 15 mg; about 3 mg to about 10 mg; about 10 mg to about 30 mg; about 10 mg to about 25 mg; about 10 mg to about 20 mg; or about 10 mg to about 15 mg.

Preferably, the fusion protein of SEQ ID NO: 1 is subcutaneously administered at doses expressed in terms of μg/kg as is often preferred for calculating dose in pediatric patients but is also useful for calculating dose for adults, and preferably at a dose of: about 1 μg/kg to about 500 μg/kg; about 1 μg/kg to about 250 μg/kg; about 1 μg/kg to about 100 μg/kg; about 1 μg/kg to about 50 μg/kg; about 1 μg/kg to about 25 μg/kg; about 1 μg/kg to about 15 μg/kg; about 1 μg/kg to about 10 μg/kg; about 1 μg/kg to about 5 μg/kg; about 5 μg/kg to about 500 μg/kg; about 5 μg/kg to about 250 μg/kg; about 5 μg/kg to about 100 μg/kg; about 5 μg/kg to about 50 μg/kg; about 5 μg/kg to about 25 μg/kg; about 5 μg/kg to about 15 μg/kg; about 5 μg/kg to about 10 μg/kg; about 15 μg/kg to about 500 μg/kg; about 15 μg/kg to about 250 μg/kg; about 15 μg/kg to about 100 μg/kg; about 15 μg/kg to about 50 μg/kg; about 15 μg/kg to about 25 μg/kg; about 50 μg/kg to about 500 μg/kg; about 50 μg/kg to about 250 μg/kg; about 50 μg/kg to about 100 μg/kg; about 150 μg/kg to about 500 μg/kg; about 150 μg/kg to about 250 μg/kg; about 200 μg/kg to about 500 μg/kg; about 250 μg/kg to about 350 μg/kg; about 300 μg/kg to about 500 μg/kg; about 300 μg/kg to about 400 μg/kg; about 400 μg/kg to about 500 μg/kg or a corresponding fixed dose thereof based on, for example, a 60-70 kg adult or a corresponding fixed dose based on a child, for example, a child of about 12 kg to about 50 kg or more.

Preferably the increase in circulating CD8+ T-cells resulting from periodic subcutaneous administration of the fusion protein of SEQ ID NO: 2 is at least about a 2-fold, at least about a 3-fold, at least about a 4-fold, at least about a 5-fold, at least about a 6-fold, at least about a 7-fold, at least about an 8-fold, about, a 9-fold, about a 10-fold, or more as compared to baseline. Preferably the ratio of increase in circulating CD8+ T cells resulting from periodic subcutaneous administration of the fusion protein of SEQ ID NO: 2 is greater relative to the ratio of increase in circulating T regulatory cells.

However, a common limitation of prior cancer immunotherapies (e.g., aldesleukin) is the exhaustion of T cells due to continuous stimulation by immunotherapy. Continuous activation of CD4$^+$ T cells and CD8$^+$ T cells by cancer immunotherapy can lead to a functionally inactivated/'exhausted' state or even cell death. Over-stimulation resulting in T cell exhaustion would be undesirable, potentially limiting the magnitude or duration of the therapeutic response. Cancer immunotherapy may also be compromised by treatment-related increases in the regulatory T cell population which act to silence the cytotoxic actions of CD8$^+$ T cells. Periodic subcutaneous dosing of the fusion protein of SEQ ID NO: 1 according to the invention may avoid both T-cell exhaustion and the potential for regulatory T-cell populations to overwhelm the cytotoxic actions of CD8+ T cells.

It has also been discovered that periodic dosing regimens of the invention showed an overall preference for expansion of CD8+ T-cells relative to NK cells, for example. It is known that increased of CD8+ T cells in the periphery and in the tumor environment a is prognostic to good response to immunotherapy.

Another surprising benefit of periodic subcutaneous dosing of the fusion protein of SEQ ID NO: 1 is that higher overall doses can be delivered with improved tolerability and less frequent dosing while achieving comparable or better anti-tumor efficacy and avoiding T cell exhaustion.

It has also been surprisingly discovered that subcutaneous administration of the fusion protein of SEQ ID NO: 1 when periodically administered at doses of about 0.3 to 30 mgs once every about 3 days (q3d) to once every about 60 days (q60d), preferably once every 3 days (q3d) to once every about 21 days (q21d), and preferably once every 4 days (q4d), once every 7 days (q7d), once every 14 days (q14d) or once every 21 days (q21d), provides other desirable and unexpected PD, PK, and immune cell profile results including that the maximal fold change in IFNγ cytokine levels over baseline as measured in the patient's blood serum after q7d subcutaneous administration is at least 2-fold greater and preferably between 2 fold and 5 fold greater than that of qdx5 intravenous administration of an equivalent dose of the fusion protein of SEQ ID NO: 1.

The maximal fold change in IL-6 cytokine levels over baseline as measured in the patient's blood serum after q7d subcutaneous administration is at least 2-fold less and preferably between 2 fold and 5 fold less than that of qdx5 intravenous administration of an equivalent dose of the fusion protein of SEQ ID NO: 1.

IFNγ is a pleiotropic cytokine with anti-tumor and immunomodulatory properties. IFNγ directly acts as a cytotoxic CD8+ T cell differential signal and it is essential for the induction of cytotoxic T cell precursor proliferation. IFNγ also upregulates cell surface MEW class II on APCs thus promoting peptide-specific activation of regulatory CD4+ T cells. In addition, IFNγ activates macrophages toward a pro-inflammatory profile, anti-tumor profile.

IL-6 on the other hand is a pro-inflammatory cytokine released by various cells in the tumor microenvironment including the cancerous cells. IL-6 plays a critical role in the expansion and differentiation of tumor cells. Increased levels of IL-6 in the serum and tumor site has been demonstrated in several cancers. Usually this increase is accompanied with a poor prognosis and lower survival rate. Downregulation of IL-6 has been correlated with a better response to cancer treatment.

Preferably the dosing regimens of the invention provide subcutaneously administering a pharmaceutical composition comprising the fusion protein of SEQ ID NO: 1 about every 3 days (q3d), about every 4 days (q4d), about every 5 days (q5d), about every 6 days (q6d), about every 7 days (q7d), about every 8 days (q8d), about every 9 days (q9d), about every 10 days Q10d), about every 11 days (q11d), about every 12 days (q12d), about every days 13 days (q13d), about every 14 days (q14d), about every 15 days (q15d), about every 16 days (q16d) about every 17 days (q17), about every 18 days (q18d), about every 19 days (q19d), about every 20 days (q20d), about every 21 days, about every 22 days, about every 23 days, about every 24 days, about every 25 days, about every 26 days, about every 27 days, or about every 28 days.

Preferably the fusion protein of SEQ ID NO: 1 is subcutaneously administered in a dose of about 0.1 mg, 1 mg, 3 mg, 6, mg, 10 mg or 30 mg about once every 3 days (q3d), about once every 4 days (q4d), about once every 7 days (q7d), about once every 14 days (q14d) or about once every 21 days (q21d).

Preferably the dosing regimen for administration of the fusion protein provides for one or more treatment courses. A first course of treatment may take place over a period of days ranging from 1-90 days. Preferably a single treatment course extends for a period of 7 days, 14 days, 21 days, 4 weeks, 6 weeks, 8 weeks, 10 weeks, 12 weeks, 4 months, 5 months, 6 months, 7 months 8 months 9 months, 10 months, 11 months, 12 months or longer. A treatment course may involve subcutaneous administration of the fusion protein of SEQ ID NO: 1 one or more times during the treatment course. There may be one or more consecutive courses of treatment such as a first treatment course followed by a second course of treatment, preferably with period of time such as one day to 1 year between the two courses of treatment.

Preferably a first course of treatment comprises subcutaneously administering the fusion protein of SEQ ID NO: 1 once every 3 days for 2-3 weeks, once every 4 days for 2-3 weeks, once every 7 days for 2-3 week or once every 21 days which may be repeated 2 or 3 times.

Formulations and pharmaceutical compositions comprising the fusion protein of SEQ ID NO: 1 suitable for SC administration and amounts effective for these uses will depend upon the severity of the disease or condition and the general state of the patient's health. Single or multiple administrations of the formulations may be administered depending on the dosage and frequency as required and tolerated by the patient.

In general, dosing parameters of monotherapy with the fusion protein of SEQ ID NO: 1 or any of the combination therapies described herein dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount can be more than the calculated ED50, in other situations the effective amount can be less than the calculated ED50, and in still other situations the effective amount can be the same as the calculated ED50.

In addition, an effective dose of the fusion protein of SEQ ID NO: 1 can be an amount that, when administered in one or more doses to a subject, produces a desired result relative to a healthy subject. For example, for a subject experiencing a particular disorder, an effective dose can be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

Preferably, the patient is administered the fusion protein of SEQ ID NO: 1 again if after initial treatment the cancer reoccurs. For example, if the patient is initially treated for a solid tumor, and the tumor returns or more tumors develop, the patient is administered SEQ ID NO: 1, as, for example, another course or series of courses of SEQ ID NO: 1.

Preferably, the fusion protein of SEQ ID NO: 1 is administered by subcutaneous injection subcutaneously injected into the same site of a patient (e.g., administered to the upper arm, anterior surface of the thigh, lower portion of the abdomen, or upper back) for repeat or continuous injections. Preferably the fusion protein of SEQ ID NO:1 is administered to different or rotating sites of a patient. Preferably the fusion protein of SEQ ID NO: 1 is administered by a subcutaneously implanted device. Preferably, the implanted device provides a timed release of the fusion protein of SEQ ID NO: 1. Preferably, the implanted device provides a continuous release of the protein of SEQ ID NO: 1.

The invention provides dosages contained in a "unit dosage form". The phrase "unit dosage form" refers to physically discrete units, each unit containing a predetermined amount of the fusion protein of SEQ ID NO: 1 either alone or in combination one or more additional complementary therapeutic agents (e.g. immune checkpoint inhibitors) sufficient to produce the desired effect. It will be appreciated that the parameters of a unit dosage form will depend on the particular agent and the effect to be achieved.

Combination Therapy with Immune Checkpoint Protein Inhibitors

Figure 2:
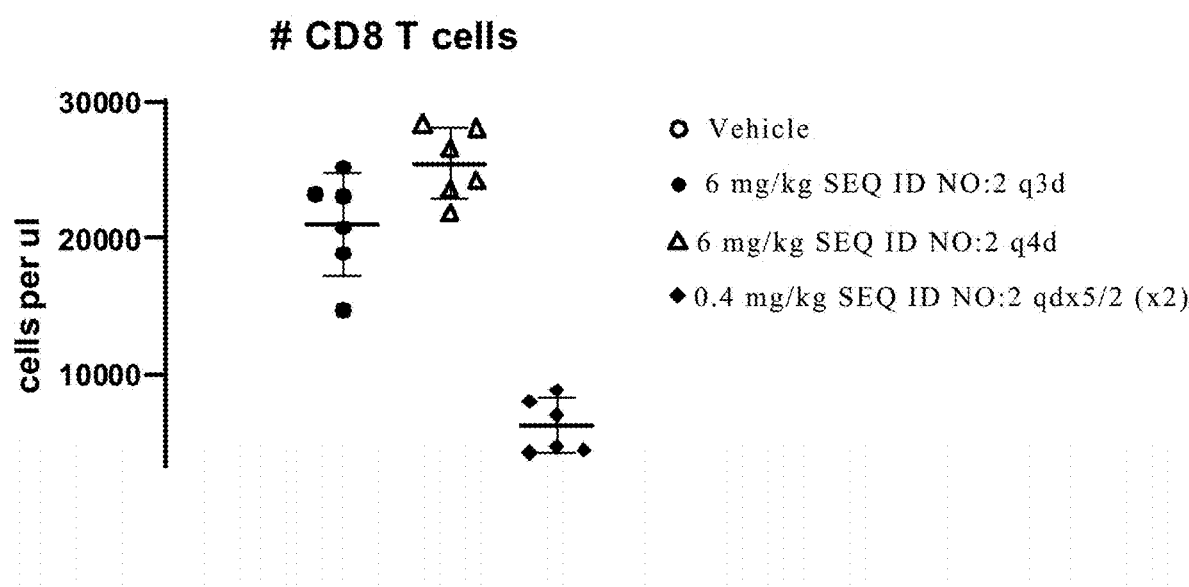
FIG. 2 is a plot graph comparing expansion of total CD8+ T-cells in FVB mice administered periodic SC dosing of SEQ ID NO: 2 at once every 3 days and once every 4 days and daily SC dosing day for 5 days with two days off.

Preferably, the fusion protein of SEQ ID NO: 1 is administered with another therapeutic and/or anti-cancer agent as described infra. Preferably the therapeutic agent is the immune checkpoint inhibitor, pembrolizumab. Preferably pembrolizumab is administered in a separate composition from the fusion protein of SEQ ID NO: 1. prior to, subsequent to, or simultaneously infusion of SEQ ID NO: 1. Preferably, pembrolizumab is administered in a dose of about 200 μg or as per the standard prescribing recommendations which is usually about once every 21 days. Preferably, pembrolizumab is administered on the first day of each course of treatment with SEQ ID NO: 1. An exemplary treatment regimen is shown in FIG. 2. Preferably, when co-administering the fusion protein of SEQ ID NO: 1 with pembrolizumab, the first course of treatment with the SEQ ID NO: 1 and all subsequent courses of treatment are generally about 21 day courses wherein the fusion protein of SEQ ID NO: 1 is subcutaneously administered only once every 3, 4, 7, 10, 14, or 21 days and pembrolizumab is administered once every 21 days.

All of the dosing regimens of the invention and described above preferably result in an increase in circulating NK cells and CD8+ T cells in a patient with minimal, effects on the expansion of regulatory T cells. Preferably, all of the dosing regimens of the invention result in a ratio of increase in CD8+ T cells that is greater relative to the ratio of increase in circulating $T_{reg}$ cells in the patient. As compared to high dose or low dose rhIL-2 therapy, all dosing regimens of the invention require less frequent dosing as compared to dosing 3 times per day dosing of high dose or low dose rhIL-2.

Preferably the fusion protein of SEQ ID NO: 1 and pharmaceutical compositions thereof, in combination with one or more immune checkpoint inhibitors to treat and/or prevent various diseases, disorders and conditions (e.g., cancers) is effected by utilizing particular dosing parameters that serve to minimize any adverse effects associated with administration of the individual therapies by themselves. By way of example, the addition of the periodic subcutaneous administration of the fusion protein of SEQ ID NO: 1 in a treatment regimen comprising an immune checkpoint inhibitor (e.g. pembrolizumab) might allow a reduction of the amount of immune checkpoint inhibitor needed to achieve the therapeutic goal, thus reducing (or even eliminating) severe and fatal immune-mediated adverse reactions that prompted the FDA to require a "black box" warning on certain immune checkpoint inhibitors (e.g. pembrolizumab).

The treatment regimens of the invention are administered to the patient until the patient is cured or until the patient is no longer benefiting from the treatment regimen.

Improved Safety Profile

Potential advantages of periodic subcutaneous dosing over daily subcutaneous or intravenous administration include: (i) lowering risk of T cell exhaustion associated with continuous T cell stimulation associated with cancer immunotherapy; (ii) lowering the risk of regulatory T cell stimulation overwhelming CD8+ T cell stimulation as a result of cancer immunotherapy; (iii) lower peak serum drug concentrations with a prolonged exposure profile, which may result in a milder safety profile and improved tolerability; (iv) lymphatic absorption, which may facilitate direct immunologic effects; (v) a more convenient dosing schedule than daily inpatient intravenous dosing, (vi) lower risk of patient weight loss; vii) higher effective dosing of the fusion protein of SEQ ID NO: 1 but with less frequent dosing, and viii) lowered risk of elevated pro-inflammatory cytokine production. The methods of the invention reduce the risk of side effects often associated with IV administration or daily SC dosing as well as reducing the risk of side effects usually associated with high dose IL-2 therapy (e.g. aldesleukin) while maintaining the desired therapeutic activity of IL-2 therapy. Such side effects include, but are not limited to, capillary leak syndrome (CLS) and cytokine release syndrome (CRS), another syndrome associated with immune therapy with cytokines that often accompanies and/or overlaps with CLS.

Also, as used herein, an "improved safety profile", or a "lower risk of side effects", or "reduced frequency or severity of a side effect" may be about a 1% decrease, about a 2% decrease, about a 3% decrease, about a 4% decrease, about a 5% decrease, about a 6% decrease, about a 7% decrease, about an 8% decrease, about a 9% decrease, about a 10% decrease, about a 20% decrease, about a 30% decrease, about a 40% decrease, about a 50% decrease, about a 60% decrease, about a 70% decrease, about an 80% decrease, about a 90% decrease, about a 100%, decrease in the manifestation of side effects or symptoms normally associated with IL-2 therapy and mitigates effects that may be the result of IV or daily SC administration of SEQ ID NO: 1.

Preferably the dosing regimen of the fusion protein of SEQ ID NO: 1 in accordance with the invention reduces the frequency and severity of capillary leak syndrome (CLS) also referred to herein as vascular leak syndrome (VLS). The risks of other side effects include, but are not limited to, cytokine-release syndrome (CRS). CRS is a serious side effect of immunotherapy having symptoms that may overlap clinically with those of CLS and yet may cause symptoms that are entirely different from CRS. CRS is thought to result from proliferating T cells that release large quantities of cytokines, including IL-6, IFN-γ, TNF, IL-2, IL-2-receptor a, IL-8, IL-10, and GM-CSF. Patients with CRS may experience any one or more of fever, cardiovascular symptoms including tachycardia, hypotension, arrhythmias, decreased cardiac ejection fraction, pulmonary symptoms including edema, hypoxia, dyspnea, and pneumonitis, acute renal injury usually caused by reduced renal perfusion, hepatic and gastrointestinal symptoms including elevated serum transaminases and bilirubin, diarrhea, colitis, nausea, and abdominal pain, hematologic symptoms including cytopenia such as grade 3-4 anemia, thrombocytopenia, leukopenia, neutropenia, and lymphopenia, derangements of coagulation including prolongation of the prothrombin time and activated partial thromboplastin time (PTT), D-dimer elevation, low fibrinogen, disseminated intravascular coagulation, macrophage activation syndrome (MAS), hemorrhage, B-cell aplasia, and hypogammaglobulinemia, infectious diseases including bacteremia, *Salmonella*, urinary tract infections, viral infections such as influenza, respiratory syncytial virus, and herpes zoster virus, musculoskeletal symptoms including elevated creatine kinase, myalgias and weakness, neurological symptoms including delirium, confusion, and seizure.

MAS overlaps clinically with CRS with subjects potentially experiencing hepatosplenomegaly, lymphadenopathy, pancytopenia, liver dysfunction, disseminated intravascular coagulation, hypofibrinogenemia, hyperferritinemia, and hypertriglyceridemia. Like CRS, subjects with MAS exhibit elevated levels of cytokines, including IFN-γ and GMCSF. Preferably the dosing regimen of the fusion protein of SEQ ID NO: 1 in accordance with the invention reduces the frequency and severity of MAS.

Another side effect of immunotherapy including IL-2 therapy is tumor lysis syndrome (TLS), which occurs when the contents of cells are released as a result of therapy causing cell death, most often with lymphoma and leukemia. TLS is characterized by blood ion and metabolite imbalance, and symptoms include nausea, vomiting, acute uric acid nephropathy, acute kidney failure, seizures, cardiac arrhythmias, and death. Preferably the dosing regimen of the fusion protein of SEQ ID NO: 1 in accordance with the invention reduces the frequency and severity of TLS.

Neurotoxicity may result from immunotherapy including IL-2 therapy and symptoms may include cerebral edema, delirium, hallucinations, dysphasia, akinetic mutism, headache, confusion, alterations in wakefulness, ataxia, apraxia, facial nerve palsy, tremor, dysmetria, and seizure. Preferably the dosing regimen of the fusion protein of SEQ ID NO: 1 in accordance with the invention reduces the frequency and severity of neurotoxicity.

Patients undergoing IL-2 immunotherapy may experience one or more side effects or symptoms that are not necessarily caused by CLS, CRS, MAS or TLS including anemia, aphasia, arrhythmia, arthralgia, back pain, blood and bone marrow disorders, blood and lymphatic system disorders, cardiac disorders, chills, coagulation disorders, colitis, confused state, constitutional symptoms, cough, decreased appetite, diarrhea, disorientation, dizziness, dyspnea, encephalopathy, fatigue, fever, gastrointestinal disorders, general cardiovascular disorders, hemorrhage, hepatic disorders, hyperglycemia, hypokalemia, hypothyroidism, increased ALT, increased AST, increased C-reactive protein, infection febrile neutropenia, leukopenia, malaise, abnormal metabolic laboratory-testing results, metabolism nutrition disorders, mucosal inflammation, musculoskeletal disorders, myalgia nausea, nervous system disorders, neurologic disorders, neutropenia edema, pain, palmar-plantar erythrodysesthesia, paresthesia, pneumonia, pruritus, pulmonary disorders, pyrexia, rash, renal genitourinary disorders, respiratory disorders, skin and subcutaneous tissue disorders, somnolence, speech disorders, sweats thoracic mediastinal disorders, thrombocytopenia, tremor, tumor flare, tumor lysis syndrome, vascular disorders, and vomiting. Preferably the dosing regimen of the fusion protein of SEQ ID NO: 1 in accordance with the invention reduces the frequency and severity of these other side effects.

Cancer Indications

The treatment regimens of the invention using the fusion protein of SEQ ID NO: 1 are useful in the treatment of many types of cancer. The term "cancer", as used herein, shall be given its ordinary meaning, as a general term for diseases in which abnormal cells divide without control. In particular, and in the context of the embodiments of the present invention, cancer refers to angiogenesis-related cancer. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Glioblastoma, Childhood; Glioblastoma, Adult; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell Lung Cancer, Small Cell Lung Cancer; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Neurofibroma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland' Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult. Benign tumors have less of a tendency to invade and are less likely to metastasize.

The term "reducing a tumor" as used herein refers to a reduction in the size or volume of a tumor mass, a decrease in the number of metastasized tumors in a subject, a decrease in the proliferative status (the degree to which the cancer cells are multiplying) of the cancer cells, and the like.

The treatment regimens of the invention are particularly suited for treating solid tumors including but not limited to: lymphomas, melanoma, renal cell carcinoma (RCC), hepatic cell carcinoma (HCC), non-small cell lung cancer (NSCLC), small cell lung cancer (SCLC), squamous cell carcinoma of the head and neck (SCCHN) and including advanced solid tumors and tumors that have previously been treated with anti-cancer therapy but remain refractory to previous therapies.

Complementary Immunotherapies and Other Combination Therapies

While the fusion protein of SEQ ID NO: 1 may be used as a monotherapy in the treatment regimens in accordance with the invention, the combination of the fusion protein of SEQ ID NO: 1 with other anticancer treatments in the context of the invention is also contemplated. Other therapeutic treatment regimens include other therapeutic immunotherapies such as adoptive cell transfer regimens, antigen-specific vaccination, inhibition of DNA repair proteins (e.g. inhibitors of the nucleic enzyme poly(adenosine 5'-diphospho-ribose) (polymerase "poly(ADP-ribose) polymerase" PARP inhibitors") and blockade of immune checkpoint inhibitory molecules, for example cytotoxic T lymphocyte-associated antigen 4 (CTLA-4) and programmed death 1 (PD-1) antibodies.

Immune checkpoint proteins regulate T cell function in the immune system. T cells play a central role in cell-mediated immunity. Immune checkpoint proteins interact with specific ligands that send a signal into the T cell and essentially switch off or inhibit T cell function. Cancer cells take advantage of this system by driving high levels of expression of checkpoint proteins on their surface that results in control of the T cells expressing immune checkpoint proteins on the surface of T cells that enter the tumor microenvironment, thus suppressing the anticancer immune response. As such, inhibition of immune checkpoint proteins by agents referred to herein as "immune checkpoint protein (ICP) inhibitors" would result in restoration of T cell function and an immune response to the cancer cells. Examples of immune checkpoint proteins include, but are not limited to: CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, OX40, B-7 family ligands or a combination thereof. Preferably, the immune checkpoint inhibitor interacts with a ligand of an immune checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, OX40, A2aR, B-7 family ligands or a combination thereof. Preferably, the immune checkpoint inhibitor is a biologic therapeutic or a small molecule. Preferably, the immune checkpoint protein inhibitor is a monoclonal antibody, a humanized antibody, a fully human antibody, a fusion protein or a combination thereof. Preferably, the PD1 immune checkpoint protein inhibitor comprises one or more anti-PD-1 antibodies, including nivolumab and pembrolizumab.

The combination therapy methods described herein include administering at least one checkpoint protein inhibitor in combination with the fusion protein of SEQ ID NO: 1. The invention is not limited to any specific checkpoint protein inhibitor so long as the checkpoint protein inhibitor inhibits one or more activities of the target checkpoint proteins when administered in an effective amount as monotherapy or in combination with the fusion protein of SEQ ID NO: 1. In some instances, due to, for example, synergistic effects, minimal inhibition of the checkpoint protein by the checkpoint protein inhibitor may be sufficient in the presence of SEQ ID NO: 1. Many checkpoint protein inhibitors are known in the art.

Exemplary PD-1/PD-L1 based immune checkpoint inhibitors include antibody-based therapeutics. Exemplary treatment methods that employ PD-1/PD-L1 based immune checkpoint inhibition are described in U.S. Pat. Nos. 8,728, 474 and 9,073,994, and EP Patent No, 1537878B1, and, for example, include the use of anti-PD-1 antibodies. Exemplary anti-PD-1 antibodies are described, for example, in U.S. Pat. Nos. 8,952,136, 8,779,105, 8,008,449, 8,741,295, 9,205,148, 9,181,342, 9,102,728, 9,102,727, 8,952,136, 8,927,697, 8,900,587, 8,735,553, and 7,488,802. Exemplary anti-PD-1 antibodies include, for example, nivolumab (OPDIVO®, Bristol-Myers Squibb Co.), pembrolizumab (KEYTRUDA®, Merck Sharp & Dohme Corp.), PDR001 (Novartis Pharmaceuticals), and pidilizumab (CT-011, Cure Tech). Exemplary anti-PD-L1 antibodies are described, for example, in U.S. Pat. Nos. 9,273,135, 7,943,743, 9,175,082, 8,741,295, 8,552,154, and 8,217,149. Exemplary anti-PD-L1 antibodies include, for example, atezolizumab (TECENTRIQ®, Genentech), durvalumab (AstraZeneca), MED14736, avelumab, and BMS 936559 (Bristol Myers Squibb Co.).

In certain embodiments, a method or composition described herein is administered in combination with a CTLA-4 inhibitor. In the CTLA-4 pathway, the interaction of CTLA-4 on a T-cell with its ligands (e.g., CD80, also known as B7-1, and CD86) on the surface of an antigen presenting cells (rather than cancer cells) leads to T-cell inhibition. Exemplary CTLA-4 based immune checkpoint inhibition methods are described in U.S. Pat. Nos. 5,811,097, 5,855,887, 6,051,227. Exemplary anti-CTLA-4 antibodies are described in U.S. Pat. Nos. 6,984,720, 6,682,736, 7,311,910; 7,307,064, 7,109,003, 7,132,281, 6,207,156, 7,807,797, 7,824,679, 8,143,379, 8,263,073, 8,318,916, 8,017,114, 8,784,815, and 8,883,984, International (PCT) Publication Nos. WO98/42752, WO00/37504, and WO01/14424, and European Patent No. EP 1212422 B1. Exemplary CTLA-4 antibodies include ipilimumab or tremelimumab.

Preferably, a method or composition of the invention is administered in combination with (i) a PD-1 or PD-L1 inhibitor, e.g., a PD-1 or PD-L1 inhibitor disclosed herein, and (ii) CTLA-4 inhibitor, e.g., a CTLA-4 inhibitor disclosed herein.

Examples of FDA Approved Immune Checkpoint Protein Inhibitors Includes:
  ipilimumab (YERVOY®)
  pembrolizumab (KEYTRUDA®)
  atezolizumab (TECENTRIQ®)
  durvalumab (IMFINZ®)
  avelumab (BAVENCIO®)
  nivolumab (OPDIVO®).

A preferred treatment regimen of the invention combines the fusion protein of SEQ ID NO: 1 subcutaneously administered in accordance with the invention with the immune checkpoint inhibitor, pembrolizumab. Preferably, pembrolizumab is administered on the first day of each treatment cycle of the treatment regimen according to the invention. Preferably 200 mg of pembrolizumab is administered in accordance with manufacturer's recommendations, generally once every three weeks or 21 days.

Treatment regimens with the fusion protein of SEQ ID NO: 1 in accordance with the invention may also be combined with other therapeutic agents and/or anti-cancer agents in addition to, or instead of, immune checkpoint inhibitors. Preferably, the therapeutic agent and/or anti-cancer agent is an antibody. Preferably, the therapeutic agent is a therapeutic protein. Preferably, the therapeutic agent is a small molecule. Preferably the anticancer agent is an antigen. Preferably, the therapeutic agent is a population of cells. Preferably, the therapeutic agent is a therapeutic antibody. Preferably the therapeutic agent is another cytotoxic and/or chemotherapeutic agent. The term "cytotoxic agent" as used herein refers to a substance that inhibits or prevents a cellular function and/or causes cell death or destruction. Chemotherapeutic agent" includes chemical compounds useful in the treatment of cancer.

Antibodies

Preferably the subcutaneous administration of SEQ ID NO: 1 may be combined with a therapeutic antibody. Methods of producing antibodies, and antigen-binding fragments thereof, are well known in the art and are disclosed in, e.g., U.S. Pat. No. 7,247,301, US2008/0138336, and U.S. Pat. No. 7,923,221, all of which are herein incorporated by reference in their entirety. Therapeutic antibodies that can be used in the methods of the present invention include, but are not limited to, any of the art-recognized therapeutic antibodies that are approved for use, in clinical trials, or in development for clinical use. In some embodiments, more than one therapeutic antibody can be included in the combination therapy of the present invention. Non-limiting examples of therapeutic antibodies include the following, without limitation:

trastuzumab (HERCEPTIN™. by Genentech, South San Francisco, Calif.), which is used to treat HER-2/neu positive breast cancer or metastatic breast cancer;
  bevacizumab (AVASTIN™ by Genentech), which is used to treat colorectal cancer, metastatic colorectal cancer, breast cancer, metastatic breast cancer, non-small cell lung cancer, or renal cell carcinoma;
  rituximab (RITUXAN™ by Genentech), which is used to treat non-Hodgkin's lymphoma or chronic lymphocytic leukemia;
  pertuzumab (OMNITARG™ by Genentech), which is used to treat breast cancer, prostate cancer, non-small cell lung cancer, or ovarian cancer;
  cetuximab (ERBITUX™ by ImClone Systems Incorporated, New York, N.Y.), which can be used to treat colorectal cancer, metastatic colorectal cancer, lung cancer, head and neck cancer, colon cancer, breast cancer, prostate cancer, gastric cancer, ovarian cancer, brain cancer, pancreatic cancer, esophageal cancer, renal cell cancer, prostate cancer, cervical cancer, or bladder cancer;
  IMC-1C11 (ImClone Systems Incorporated), which is used to treat colorectal cancer, head and neck cancer, as well as other potential cancer targets;
  tositumomab and tositumomab and iodine $I^{131}$ (BEXXAR™ by Corixa Corporation, Seattle, Wash.), which is used to treat non-Hodgkin's lymphoma, which can be CD20 positive, follicular, non-Hodgkin's lymphoma, with and without transformation, whose disease is refractory to Rituximab and has relapsed following chemotherapy;
  $In^{111}$ ibritumomab tiuxetan; $Y^{90}$ ibritumomab tiuxetan; $I^{111}$ ibritumomab tiuxetan and $Y^{90}$ ibritumomab tiuxetan (ZEVALIN™ by Biogen Idec, Cambridge, Mass.), which is used to treat lymphoma or non-Hodgkin's lymphoma, which can include relapsed follicular lymphoma; relapsed or refractory, low grade or follicular non-Hodgkin's lymphoma; or transformed B-cell non-Hodgkin's lymphoma;
  EMD 7200 (EMD Pharmaceuticals, Durham, N.C.), which is used for treating for treating non-small cell lung cancer or cervical cancer;
  SGN-30 (a genetically engineered monoclonal antibody targeted to CD30 antigen by Seattle Genetics, Bothell, Wash.), which is used for treating Hodgkin's lymphoma or non-Hodgkin's lymphoma;
  SGN-15 (a genetically engineered monoclonal antibody targeted to a Lewisy-related antigen that is conjugated to doxorubicin by Seattle Genetics), which is used for treating non-small cell lung cancer;
  SGN-33 (a humanized antibody targeted to CD33 antigen by Seattle Genetics), which is used for treating acute myeloid leukemia (AML) and myelodysplastic syndromes (MDS);

SGN-40 (a humanized monoclonal antibody targeted to CD40 antigen by Seattle Genetics), which is used for treating multiple myeloma or non-Hodgkin's lymphoma;

SGN-35 (a genetically engineered monoclonal antibody targeted to a CD30 antigen that is conjugated to auristatin E by Seattle Genetics), which is used for treating non-Hodgkin's lymphoma;

SGN-70 (a humanized antibody targeted to CD70 antigen by Seattle Genetics), that is used for treating renal cancer and nasopharyngeal carcinoma;

SGN-75 (a conjugate comprised of the SGN70 antibody and an Auristatin derivative by Seattle Genetics); and SGN-17/19 (a fusion protein containing antibody and enzyme conjugated to melphalan prodrug by Seattle Genetics), which is used for treating melanoma or metastatic melanoma.

The therapeutic antibodies to be used in the methods of the present invention are not limited to those described herein. For example, the following approved therapeutic antibodies can also be used in the methods of the invention: brentuximab vedotin (ADCETRIS™) for anaplastic large cell lymphoma and Hodgkin lymphoma, ipilimumab (MDX-101; YERVOY™) for melanoma, ofatumumab (ARZ-ERRA™) for chronic lymphocytic leukemia, panitumumab (VECTIBIX™) for colorectal cancer, alemtuzumab (CAMPATH™) for chronic lymphocytic leukemia, ofatumumab (ARZERRA™) for chronic lymphocytic leukemia, gemtuzumab ozogamicin (MYLOTARG™) for acute myelogenous leukemia.

Antibodies for use in accordance with the invention can also target molecules expressed by immune cells, such as, but not limited to, tremelimumab (CP-675,206) and ipilimumab (MDX-010) which targets CTLA4 and has the effect of tumor rejection, protection from re-challenge, and enhanced tumor-specific T cell responses; OX86 which targets OX40 and increases antigen-specific CD8+ T cells at tumor sites and enhances tumor rejection; CT-011 which targets PD 1 and has the effect of maintaining and expanding tumor specific memory T cells and activates NK cells; BMS-663513 which targets CD137 and causes regression of established tumors, as well as the expansion and maintenance of CD8+ T cells, and daclizumab (ZENAPAX™) which targets CD25 and causes transient depletion of CD4+ CD25+FOXP3+Tregs and enhances tumor regression and increases the number of effector T cells. A more detailed discussion of these antibodies can be found in, e.g., Weiner et al., Nature Rev. Immunol 2010; 10:317-27.

Preferably, the antibody is a pro-inflammatory and/or pro-tumorigenic cytokine targeting antibody including, but not limited to, anti-TNF antibodies, anti-IL-1Ra receptor targeting antibodies, anti-IL-1 antibodies, anti-IL-6 receptor antibodies, and anti-IL-6 antibodies. Preferably antibodies include those that target pro-inflammatory T helper type 17 cells (TH17).

The therapeutic antibody can be a fragment of an antibody; a complex comprising an antibody; or a conjugate comprising an antibody. The antibody can optionally be chimeric or humanized or fully human.

Therapeutic Proteins and Polypeptides

Preferably the methods of the invention include subcutaneous administration of the fusion protein of SEQ ID NO: 1 in accordance with the treatment regimen of the invention in combination with a therapeutic protein or peptide. Therapeutic proteins that are effective in treating cancer are well known in the art, Preferably, the therapeutic polypeptide or protein is a "suicide protein" that causes cell death by itself or in the presence of other compounds.

A representative example of such a suicide protein is thymidine kinase of the herpes simplex virus. Additional examples include thymidine kinase of varicella zoster virus, the bacterial gene cytosine deaminase (which converts 5-fluorocytosine to the highly toxic compound 5-fluorouracil), p450 oxidoreductase, carboxypeptidase G2, beta-glucuronidase, penicillin-V-amidase, penicillin-G-amidase, beta-lactamase, nitroreductase, carboxypeptidase A, linamarase (also referred to as β-glucosidase), the E. coli gpt gene, and the E. coli Deo gene, although others are known in the art. In some embodiments, the suicide protein converts a prodrug into a toxic compound.

As used herein, "prodrug" means any compound useful in the methods of the present invention that can be converted to a toxic product, i.e. toxic to tumor cells. The prodrug is converted to a toxic product by the suicide protein. Representative examples of such prodrugs include: ganciclovir, acyclovir, and FIAU (1-(2-deoxy-2-fluoro-β-D-arabinofuranosyl)-5-iod-ouracil) for thymidine kinase; ifosfamide for oxidoreductase; 6-methoxypurine arabinoside for VZV-TK; 5-fluorocytosine for cytosine deaminase; doxorubicin for beta-glucuronidase; CB 1954 and nitrofurazone for nitroreductase; and N-(Cyanoacetyl)-L-phenylalanine or N-(3-chloropropionyl)-L-phenylalanine for carboxypeptidase A. The prodrug may be administered readily by a person having ordinary skill in this art. A person with ordinary skill would readily be able to determine the most appropriate dose and route for the administration of the prodrug.

Preferably the therapeutic protein or polypeptide, is a cancer suppressor, for example p53 or Rb, or a nude acid encoding such a protein or polypeptide. Those of skill know of a wide variety of such cancer suppressors and how to obtain them and/or the nucleic acids encoding them.

Other examples of anti-cancer/therapeutic proteins or polypeptides include pro-apoptotic therapeutic proteins and polypeptides, for example, p15, p16, or p21$^{WAF-1}$.

Cytokines, and nucleic acid encoding them may also be used as therapeutic proteins and polypeptides. Examples include: GM-CSF (granulocyte macrophage colony stimulating factor); TNF-alpha (Tumor necrosis factor alpha); Interferons including, but not limited to, IFN-alpha and IFN-gamma; and Interleukins including, but not limited to, Interleukin-1 (IL-1), Interleukin-Beta (IL-beta), Interleukin-2 (IL-2), Interleukin-4 (IL-4), Interleukin-5 (IL-5), Interleukin-6 (IL-6), Interleukin-7 (IL-7), Interleukin-8 (IL-8), Interleukin-10 (IL-10), Interleukin-12 (IL-12), Interleukin-13 (IL-13), Interleukin-14 (IL-14), Interleukin-15 (IL-15), Interleukin-16 (IL-16), Interleukin-18 (IL-18), Interleukin-23 (IL-23), Interleukin-24 (IL-24), although other embodiments are known in the art.

Additional examples of cytocidal genes includes, but is not limited to, mutated cyclin G1 genes. By way of example, the cytocidal gene may be a dominant negative mutation of the cyclin G1 protein (e.g., WO/01/64870).

Vaccines

Preferably, the therapeutic regimens of the invention include subcutaneous administration of a fusion protein of SEQ ID NO: 1 in combination with administration of a cancer vaccine for stimulating a cancer specific-immune response, e.g., innate and adaptive immune responses, for generating host immunity against a cancer (see, e.g., Overwijk, et al. Journal of Experimental Medicine 2008; 198: 569-80). Illustrative vaccines include, but are not limited to, for example, antigen vaccines, whole cell vaccines, dendritic cell vaccines, and DNA vaccines. Depending upon the particular type of vaccine, the vaccine composition may include one or more suitable adjuvants known to enhance a subject's immune response to the vaccine.

The vaccine may, for example, be cellular based, i.e., created using cells from the patient's own cancer cells to identify and obtain an antigen. Exemplary vaccines include tumor cell-based and dendritic-cell based vaccines, where activated immune cells from the subject are delivered back to the same subject, along with other proteins, to further facilitate immune activation of these tumor antigen primed immune cells. Tumor cell-based vaccines include whole tumor cells and gene-modified tumor cells. Whole tumor cell vaccines may optionally be processed to enhance antigen presentation, e.g., by irradiation of either the tumor cells or tumor lysates). Vaccine administration may also be accompanied by adjuvants such as *bacillus* calmette-guerin (BCG) or keyhole limpet hemocyanin (KLH), depending upon the type of vaccine employed. Plasmid DNA vaccines may also be used and can be administered via direct injection or biolistically. Also contemplated for use are peptide vaccines, viral gene transfer vector vaccines, and antigen-modified dentritic cells (DCs).

Preferably the vaccine is a therapeutic cancer peptide-based vaccine. Peptide vaccines can be created using known sequences or from isolated antigens from a subject's own tumor(s) and include neoantigens and modified antigens. Illustrative antigen-based vaccines include those where the antigen is a tumor-specific antigen. For example, the tumor-specific antigen may be selected from a cancer-testis antigen, a differentiation antigen, and a widely occurring overexpressed tumor associated antigen, among others. Recombinant peptide vaccines, based on peptides from tumor-associated antigens, when used in the instant method, may be administered or formulated with, an adjuvant or immune modulator. Illustrative antigens for use in a peptide-based vaccine include, but are not limited to, the following, since this list is meant to be purely illustrative. For example, a peptide vaccine may comprise a cancer-testis antigen such as MAGE, BAGE, NY-ESO-1 and SSX-2, encoded by genes that are normally silenced in adult tissues but transcriptionally reactivated in tumor cells. Alternatively, the peptide vaccine may comprise a tissue differentiation associated antigen, i.e., an antigen of normal tissue origin and shared by both normal and tumorous tissue. For example, the vaccine may comprise a melanoma-associated antigen such as gp100, Melan-A/Mart-1, MAGE-3, or tyrosinase; or may comprise a prostate cancer antigen such as PSA or PAP. The vaccine may comprise a breast cancer-associated antigen such as mammaglobin-A. Other tumor antigens that may be comprised in a vaccine for use in the instant method include, for example, CEA, MUC-1, HER1/Nue, hTERT, ras, and B-raf. Other suitable antigens that may be used in a vaccine include SOX-2 and OCT-4, associated with cancer stem cells or the EMT process.

Antigen vaccines include multi-antigen and single antigen vaccines. Exemplary cancer antigens may include peptides having from about 5 to about 30 amino acids, or from about 6 to 25 amino acids, or from about 8 to 20 amino acids.

As described above, an immunostimulatory adjuvant (different from RSLAIL-2) may be used in a vaccine, in particular, a tumor-associated antigen-based vaccine, to assist in generating an effective immune response. For example, a vaccine may incorporate a pathogen-associated molecular pattern (PAMP) to assist in improving immunity. Additional suitable adjuvants include monophosphoryl lipid A, or other lipopolysaccharides; toll-like receptor (TLR) agonists such as, for example, imiquimod, resiquimod (R-848), TLR3, IMO-8400, and rintatolimod. Additional adjuvants suitable for use include heat shock proteins.

A genetic vaccine typically uses viral or plasmid DNA vectors carrying expression cassettes. Upon administration, they transfect somatic cells or dendritic cells as part of the inflammatory response to thereby result in cross-priming or direct antigen presentation. Preferably, a genetic vaccine is one that provides delivery of multiple antigens in one immunization. Genetic vaccines include DNA vaccines, RNA vaccines and viral-based vaccines.

DNA vaccines for use in the instant methods are bacterial plasmids that are constructed to deliver and express tumor antigen. DNA vaccines may be administered by any suitable mode of administration, e.g., subcantaneous or intradermal injection, but may also be injected directly into the lymph nodes. Additional modes of delivery include, for example, gene gun, electroporation, ultrasound, laser, liposomes, microparticles and nanoparticles.

Preferably, the vaccine comprises a neoantigen, or multiple neoantigens. Preferably, the vaccine is a neoantigen-based vaccine. Preferably a neoantigen-based vaccine (NBV) composition may encode multiple cancer neoantigens in tandem, where each neoantigen is a polypeptide fragment derived from a protein mutated in cancer cells. For instance, a neoantigenic vaccine may comprise a first vector comprising a nucleic acid construct encoding multiple immunogenic polypeptide fragments, each of a protein mutated in cancer cells, where each immunogenic polypeptide fragment comprises one or more mutated amino acids flanked by a variable number of wild type amino acids from the original protein, and each polypeptide fragment is joined head-to-tail to form an immunogenic polypeptide. The lengths of each of the immunogenic polypeptide fragments forming the immunogenic polypeptide can vary.

Viral gene transfer vector vaccines may also be used; in such vaccines, recombinant engineered virus, yeast, bacteria or the like is used to introduce cancer-specific proteins to the patient's immune cells. In a vector-based approach, which can be tumor lytic or non-tumor lytic, the vector can increase the efficiency of the vaccine due to, for example, its inherent immunostimulatory properties. Illustrative viral-based vectors include those from the poxviridae family, such as vaccinia, modified vaccinia strain Ankara and avipoxviruses. Also suitable for use is the cancer vaccine, PROSTVAC, containing a replication-competent vaccinia priming vector and a replication-incompetent fowlbox-boosting vector. Each vector contains transgenes for PSA and three co-stimulatory molecules, CD80, CD54 and CD58, collectively referred to as TRICOM. Other suitable vector-based cancer vaccines include Trovax and TG4010 (encoding MUC1 antigen and IL-2). Additional vaccines for use include bacteria and yeast-based vaccines such as recombinant *Listeria monocytogenes* and *Saccharomyces cerevisae*.

The foregoing vaccines may be combined and/or formulated with adjuvants and other immune boosters to increase efficacy. Depending upon the particular vaccine, administration may be either intratumoral or non-intratumoral (i.e., systemic).

Other cancer antigens that can be used in vaccinations include, but are not limited to, (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen.

In another embodiment, the cancer antigen is a lymphoma antigen (e.g., non-Hodgkin's lymphoma or Hodgkin's lymphoma), a B-cell lymphoma cancer antigen, a leukemia antigen, a myeloma (i.e., multiple myeloma or plasma cell myeloma) antigen, an acute lymphoblastic leukemia antigen, a chronic myeloid leukemia antigen, or an acute myelogenous leukemia antigen. The described cancer antigens are only exemplary, and that any cancer antigen can be targeted in the present invention.

Preferably, the cancer antigen is a mucin-1 protein or peptide (MUC-1) that is found on all human adenocarcinomas: pancreas, colon, breast, ovarian, lung, prostate, head and neck, including multiple myelomas and some B cell lymphomas. Patients with inflammatory bowel disease, either Crohn's disease or ulcerative colitis, are at an increased risk for developing colorectal carcinoma. MUC-1 is a type I transmembrane glycoprotein. The major extracellular portion of MUC-1 has a large number of tandem repeats consisting of 20 amino acids which comprise immunogenic epitopes. In some cancers it is exposed in an unglycosylated form that is recognized by the immune system (Gendler et al., *J Biol Chem* 1990; 265:15286-15293).

In another embodiment, the cancer antigen is a mutated B-Raf antigen, which is associated with melanoma and colon cancer. The vast majority of these mutations represent a single nucleotide change of T-A at nucleotide 1796 resulting in a valine to glutamic acid change at residue 599 within the activation segment of B-Raf. Raf proteins are also indirectly associated with cancer as effectors of activated Ras proteins, oncogenic forms of which are present in approximately one-third of all human cancers. Normal non-mutated B-Raf is involved in cell signaling, relaying signals from the cell membrane to the nucleus. The protein is usually only active when needed to relay signals. In contrast, mutant B-Raf has been reported to be constantly active, disrupting the signaling relay (Mercer and Pritchard, Biochim Biophys Acta (2003) 1653(1):25-40; Sharkey et al., Cancer Res. (2004) 64(5):1595-1599).

Preferably, the cancer antigen is a human epidermal growth factor receptor-2 (HER-2/neu) antigen. Cancers that have cells that overexpress HER-2/neu are referred to as HER-2/neu$^+$ cancers. Exemplary HER-2/neu$^+$ cancers include prostate cancer, lung cancer, breast cancer, ovarian cancer, pancreatic cancer, skin cancer, liver cancer (e.g., hepatocellular adenocarcinoma), intestinal cancer, and bladder cancer.

HER-2/neu has an extracellular binding domain (ECD) of approximately 645 aa, with 40% homology to epidermal growth factor receptor (EGFR), a highly hydrophobic transmembrane anchor domain (TMD), and a carboxyterminal intracellular domain (ICD) of approximately 580 aa with 80% homology to EGFR. The nucleotide sequence of HER-2/neu is available at GENBANK™. Accession Nos. AH002823 (human HER-2 gene, promoter region and exon 1); M16792 (human HER-2 gene, exon 4): M16791 (human HER-2 gene, exon 3); M16790 (human HER-2 gene, exon 2); and M16789 (human HER-2 gene, promoter region and exon 1). The amino acid sequence for the HER-2/neu protein is available at GENBANK™ Accession No. AAA58637. Based on these sequences, one skilled in the art could develop HER-2/neu antigens using known assays to find appropriate epitopes that generate an effective immune response.

Exemplary HER-2/neu antigens include p369-377 (a HER-2/neu derived HLA-A2 peptide); dHER2 (Corixa Corporation); li-Key MHC class II epitope hybrid (Generex Biotechnology Corporation); peptide P4 (amino acids 378-398); peptide P7 (amino acids 610-623); mixture of peptides P6 (amino acids 544-560) and P7; mixture of peptides P4, P6 and P7; HER2 [9$_{754}$]; and the like.

Preferably, the cancer antigen is an epidermal growth factor receptor (EGFR) antigen. The EGFR antigen can be an EGFR variant 1 antigen, an EGFR variant 2 antigen, an EGFR variant 3 antigen and/or an EGFR variant 4 antigen. Cancers with cells that overexpress EGFR are referred to as EGFR cancers. Exemplary EGFR cancers include lung cancer, head and neck cancer, colon cancer, colorectal cancer, breast cancer, prostate cancer, gastric cancer, ovarian cancer, brain cancer and bladder cancer.

Preferably, the cancer antigen is a vascular endothelial growth factor receptor (VEGFR) antigen. VEGFR is considered to be a regulator of cancer-induced angiogenesis. Cancers with cells that overexpress VEGFR are called VEGFR$^+$ cancers. Exemplary VEGFR$^+$ cancers include breast cancer, lung cancer, small cell lung cancer, colon cancer, colorectal cancer, renal cancer, leukemia, and lymphocytic leukemia.

Preferably, the cancer antigen is prostate-specific antigen (PSA) and/or prostate-specific membrane antigen (PSMA) that are prevalently expressed in androgen-independent prostate cancers.

Preferably, the cancer antigen is Gp-100 Glycoprotein 100 (gp 100) is a tumor-specific antigen associated with melanoma.

Preferably, the cancer antigen is a carcinoembryonic (CEA) antigen. Cancers with cells that overexpress CEA are referred to as CEA$^+$ cancers. Exemplary CEA$^+$ cancers include colorectal cancer, gastric cancer and pancreatic cancer. Exemplary CEA antigens include CAP-1 (i.e., CEA aa 571-579), CAP1-6D, CAP-2 (i.e., CEA aa 555-579), CAP-3 (i.e., CEA aa 87-89), CAP-4 (CEA aa 1-11), CAP-5 (i.e., CEA aa 345-354), CAP-6 (i.e., CEA aa 19-28) and CAP-7.

Preferably, the cancer antigen is carbohydrate antigen 10.9 (CA 19.9). CA 19.9 is an oligosaccharide related to the Lewis A blood group substance and is associated with colorectal cancers.

Preferably, the cancer antigen is a melanoma cancer antigen. Melanoma cancer antigens are useful for treating melanoma. Exemplary melanoma cancer antigens include MART-1 (e.g., MART-1 26-35 peptide, MART-1 27-35 peptide); MART-1/Melan A; pMel17; pMel17/gp100; gp100 (e.g., gp 100 peptide 280-288, gp 100 peptide 154-162, gp 100 peptide 457-467); TRP-1; TRP-2; NY-ESO-1; p16; beta-catenin; mum-1; and the like.

Preferably, the cancer antigen is a mutant or wild type ras peptide. The mutant ras peptide can be a mutant K-ras peptide, a mutant N-ras peptide and/or a mutant H-ras peptide. Mutations in the ras protein typically occur at positions 12 (e.g., arginine or valine substituted for glycine), 13 (e.g., asparagine for glycine), 61 (e.g., glutamine to leucine) and/or 59. Mutant ras peptides can be useful as lung cancer antigens, gastrointestinal cancer antigens, hepatoma antigens, myeloid cancer antigens (e.g., acute leukemia, myelodysplasia), skin cancer antigens (e.g., melanoma, basal cell, squamous cell), bladder cancer antigens, colon cancer antigens, colorectal cancer antigens, and renal cell cancer antigens.

In another embodiment of the invention, the cancer antigen is a mutant and/or wildtype p53 peptide. The p53 peptide can be used as colon cancer antigens, lung cancer antigens, breast cancer antigens, hepatocellular carcinoma cancer antigens, lymphoma cancer antigens, prostate cancer antigens, thyroid cancer antigens, bladder cancer antigens, pancreatic cancer antigens and ovarian cancer antigens.

The cancer antigen can be a cell, a protein, a peptide, a fusion protein, DNA encoding a peptide or protein, RNA encoding a peptide or protein, a glycoprotein, a lipoprotein, a phosphoprotein, a carbohydrate, a lipopolysaccharide, a lipid, a chemically linked combination of two or more thereof, a fusion or two or more thereof, or a mixture of two or more thereof, or a virus encoding two or more thereof, or an oncolytic virus encoding two or more thereof. In another embodiment, the cancer antigen is a peptide comprising about 6 to about 24 amino acids; from about 8 to about 20 amino acids; from about 8 to about 12 amino acids; from about 8 to about 10 amino acids; or from about 12 to about 20 amino acids. In one embodiment, the cancer antigen is a peptide having a MHC Class I binding motif or a MHC Class II binding motif. In another embodiment, the cancer antigen comprises a peptide that corresponds to one or more cytotoxic T lymphocyte (CTL) epitopes.

Cell Therapy

Preferably, the methods of the invention include administration of the fusion protein of SEQ ID NO: 1 in combination with administration of a therapeutic cell therapy. Cell therapies that are useful for treating cancer are well known and are disclosed in, e.g., U.S. Pat. No. 7,402,431. In a preferred embodiment, the cell therapy is T cell transplant. In a preferred method, T cells are expanded ex vivo with IL-2 prior to transplantation into a subject. Methods for cell therapies are disclosed in, e.g., U.S. Pat. No. 7,402,431, US2006/0057121, U.S. Pat. Nos. 5,126,132, 6,255,073, 5,846,827, 6,251,385, 6,194,207, 5,443,983, 6,040,177, 5,766,920, and US2008/0279836.

Radiation Therapy

Preferably, the therapeutic regimens of the invention include administration of a fusion protein of SEQ ID NO: 1 in further combination with radiation therapy. The term "radiation therapy" may be used interchangeably with the term "radiotherapy", is a type of cancer treatment that uses beams of intense energy to kill cancer cells. Radiation therapy most often uses X-rays, but gamma rays, electron beams, or protons also can be used. The term "radiation therapy" most often refers to external beam radiation therapy. During this type of radiation, the high-energy beams come from a machine outside of the patient's body that aims the beams at a precise point on the body. Each session is quick and painless, lasting about 15 minutes. As used herein, the term "session" or "session of treatment" refers to each radiotherapy treatment. A radiation therapy "regimen" or "schedule" usually consists of a specific number of treatments given over a set period of time, depending on the type and the stage of the cancer.

Small Molecules

Preferably, the therapeutic regimens of the invention include subcutaneous administration of a fusion protein of SEQ ID NO: 1 in combination with administration of an anticancer small molecule. Small molecules that are effective in treating cancer are well known in the art and include antagonists of factors that are involved in tumor growth, such as EGFR, ErbB2 (also known as Her2) ErbB3, ErbB4, or TNF. Non-limiting examples include small molecule receptor tyrosine kinase inhibitors (RTKIs) that target one or more tyrosine kinase receptors, such as VEGF receptors, FGF receptors, EGF receptors and PDGF receptors.

Many therapeutic small molecule RTKIs are known in the art, including, but are not limited to, vatalanib (PTK787), erlotinib (TARCEVA™), OSI-7904, ZD6474 (ZACTIMA™), ZD6126 (ANG453), ZD1839, sunitinib (SUTENT™), semaxanib (SU5416), AMG706, AG013736, Imatinib (GLEEVEC™), MLN-518, CEP-701, PKC-412, Lapatinib (GSK572016), VELCADE™, AZD2171, sorafenib (NEXAVAR™), XL880, and CHIR-265. Small molecule protein tyrosine phosphatase inhibitors, such as those disclosed in Jiang et al., Cancer Metastasis Rev. 2008; 27:263-72 are also useful for practicing the methods of the invention. Such inhibitors can target, e.g., HSP2, PRL, PTP1B, or Cdc25 phosphatases.

Small molecules that target Bcl-2/Bcl-XL, such as those disclosed in US2008/0058322, are also useful for practicing the methods of the present invention. Further exemplary small molecules for use in the present invention are disclosed in Zhang et al. Nature Reviews: Cancer 2009; 9:28-39. In particular, chemotherapeutic agents that lead to immunogenic cell death such as anthracyclins (Kepp et al., *Cancer and Metastasis Reviews* 2011; 30:61-9) will be well suited for synergistic effects with extended-PK IL-2.

Other Cytotoxic and Chemotherapeutic Agents

Preferably, the methods of the invention include subcutaneous administration of the fusion protein of SEQ ID NO: 1 in combination with administration with chemotherapeutic agents including but not limited to, alkylating agents, antitumor antibiotics, antimetabolic agents, other anti-tumor antibiotics, and plant derived agents.

Alkylating agents are drugs which impair cell function by forming covalent bonds with amino, carboxyl, sulfhydryl and phosphate groups in biologically important molecules. The most important sites of alkylation are DNA, RNA and proteins. Alkylating agents depend on cell proliferation for activity but are not cell-cycle-phase-specific. Alkylating agents suitable for use in the present invention include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitroso-ureas (e. g. BCNU, carmustine, lomustine, streptozocin), nonclassic alkylating agents (e.g., altretamine, dacarbazine, and procarbazine), and platinum compounds (e.g., carboplastin, oxaliplatin and cisplatin).

Antitumor antibiotics like adriamycin intercalate DNA at guanine-cytosine and guanine-thymine sequences, resulting in spontaneous oxidation and formation of free oxygen radicals that cause strand breakage. Other antibiotic agents suitable for use in the present invention include, but are not limited to, anthracyclines (e. g. doxorubicin, daunorubicin, epirubicin, idarubicin and anthracenedione), mitomycin C, bleomycin, dactinomycin, and plicatomycin.

Antimetabolic agents suitable for use in the present invention include but are not limited to, floxuridine, fluorouracil, methotrexate, leucovorin, hydroxyurea, thioguanine, mercaptopurine, cytarabine, pentostatin, fludarabine phosphate, cladribine, asparaginase, and gemcitabine.

Plant derived agents include taxanes, which are semisynthetic derivatives of extracted precursors from the needles of yew plants. These drugs have a novel 14-member ring, the taxane. Unlike the *vinca* alkaloids, which cause microtubular disassembly, the taxanes (e.g., taxol) promote microtubular assembly and stability, therefore blocking the cell cycle in mitosis. Other plant derived agents include, but are not limited to, vincristine, vinblastine, vindesine, vinzolidine, vinorelbine, etoposide, teniposide, and docetaxel.

Compositions for Combination Therapy

Preferably, the fusion protein of SEQ ID NO: 1 is administered in combination (simultaneously or sequentially) with one or more additional therapeutic agents or other therapeutic agents, such as a therapeutic antibody. Preferably, the fusion protein of SEQ ID NO: 1 is subcutaneously administered prior to the administration of one or more therapeutic agents, such as a therapeutic antibody. Preferably, the fusion protein of SEQ ID NO: 1 is subcutaneously administered concurrent with the administration of one or more therapeutic agents, such as a therapeutic antibody. Preferably, the fusion protein of SEQ ID NO: 1 is subcutaneously administered subsequent to the administration of one or more therapeutic agents, such as a therapeutic antibody. Preferably, the fusion protein of SEQ ID NO: 1 and one or more therapeutic agents, such as a therapeutic antibody, are administered simultaneously. Preferably, fusion protein of SEQ ID NO: 1 and one or more therapeutic agents, such as a therapeutic antibody, are administered sequentially. Preferably, the fusion protein of SEQ ID NO: 1 and one or more therapeutic agents, such as a therapeutic antibody, are administered within one, two, or three days of each other.

Preferably, the invention provides for separate pharmaceutical compositions comprising the fusion protein with a pharmaceutically acceptable diluent, carrier, solubilizer, emulsifier, preservative and/or adjuvant and another pharmaceutical composition comprising one or more therapeutic agents, such as a therapeutic antibody, with a pharmaceutically acceptable diluent, carrier, solubilizer, emulsifier, preservative and/or adjuvant.

Preferably, the invention provides for pharmaceutical compositions comprising the fusion protein of SEQ ID NO: 1 and one or more therapeutic or anti-cancer agents in the same composition, together with a pharmaceutically acceptable diluent, carrier, solubilizer, emulsifier, preservative and/or adjuvant.

Recombinant Production

Preferably the fusion protein of SEQ ID NO: 1 is produced using recombinant techniques. The fusion protein of SEQ ID NO: 1 can be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that can be used as host cells include insect cells, mammalian cells, and/or plant cells. Where mammalian host cells are used, they can include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide can be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences and can provide for inducible or constitutive expression where the coding region is operably-linked under the transcriptional control of the transcriptional initiation region, and a transcriptional and translational termination region. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host can be present to facilitate selection of cells containing the vector. Moreover, the expression construct can include additional elements. For example, the expression vector can have one or two replication systems, thus allowing it to be maintained in organisms, for example, in mammalian or insect cells for expression and in a prokaryotic host for cloning and amplification. In addition, the expression construct can contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein can be isolated using metal chelate chromatography methods. Proteins can contain modifications to facilitate isolation.

The fusion protein of SEQ ID NO: 1 can be prepared in substantially pure or isolated form (e.g., free from other polypeptides). The polypeptides can be present in a composition that is enriched for the polypeptide relative to other components that can be present (e.g., other polypeptides or other host cell components). For example, purified fusion protein can be provided such that the fusion protein is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

Preferably, the fusion protein of SEQ ID NO: 1 may be produced using a biological recombinant expression system typically involving transfecting cells with a DNA vector that contains a genetic template encoding the fusion protein of SEQ ID NO: 1 and then culturing the cells so that they transcribe and translate the Fusion Protein. Typically, the cells are then lysed to extract the expressed protein for subsequent purification. Both prokaryotic and eukaryotic in vivo protein expression systems are suitable for use. Preferably, the fusion protein of SEQ ID NO: 1 is produced in CHO cells.

Kits

Also provided are kits comprising a fusion protein of SEQ ID NO: 1 formulated for SC administration, and optionally any other chemotherapeutic or anti-cancer agent. The kits are generally in the form of a physical structure housing various components, as described below, and can be utilized, for example, in practicing the methods described above. A kit can include the fusion protein of SEQ ID NO: 1 (provided in, e.g., a sterile container), which can be in the form of a pharmaceutical composition suitable for administration to a subject. The pharmaceutical composition can be provided in a form that is ready for use or in a form requiring, for example, reconstitution or dilution prior to administration. When the compositions are in a form that needs to be reconstituted by a user, the kit can also include buffers, pharmaceutically acceptable excipients, and the like, packaged with or separately from the fusion protein of SEQ ID NO: 1. When combination therapy (e.g., the fusion protein of SEQ ID NO: 1 and an immune checkpoint inhibitor(s) is contemplated, the kit can contain the several agents separately or they can already be combined in the kit. Similarly, when additional complementary therapy is required (e.g., a fusion protein of SEQ ID NO: 1, an immune checkpoint inhibitor(s), and an additional complementary therapy or agent) is, the kit can contain the several agents separately or two or more of them can already be combined in the kit.

A kit of the invention can be designed for conditions necessary to properly maintain the components housed therein (e.g., refrigeration or freezing). A kit can contain a label or packaging insert including identifying information for the components therein and instructions for their use (e.g., dosing parameters, clinical pharmacology of the active ingredient(s), including mechanism(s) of action, pharmacokinetics and pharmacodynamics, adverse effects, contraindications, etc.).

Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via an internet site, are provided.

EXAMPLES

Example 1—Periodic Subcutaneous Administration in Animal Models with for Limiting T-Cell Exhaustion/Inactivation Introduction/Rationale Activation of CD4+ T cells and CD8+ T cells can lead to a functionally inactivated/'exhausted' state or even cell death. For an immune-oncology therapy, such as aldesleukin, over-stimulation resulting in T cell exhaustion would be catastrophic to the outcome, potentially limiting the magnitude or duration of the therapeutic response. Moreover, immunotherapy can also be minimized by treatment-related increases in the regulatory T cell (Tregs) population which act to silence the cytotoxic actions of CD8+ T cells. Preclinical experiments are described herein to determine if the rodent homolog of the fusion protein of SEQ ID NO: 1 (the rodent homolog is identified as SEQ ID NO: 2) exhibits an improved pharmacodynamic profile following periodic dosing regimens compared to a constant i.e., daily dosing regimen of the rodent homolog or recombinant IL-2. Pharmacodynamic markers of IL-2 treatment were validated which included the assessment of cellular (CD8$^+$ T cells and NK cells) and cytokine (IFN$\gamma$ profiles) following dosing, as well as anti-tumor efficacy in syngeneic tumor models in mice.

In addition, a safety/side effect limitation of the clinical use of aldesleukin is vascular leak syndrome. Therefore, we also evaluated a surrogate marker of vascular leak syndrome, lung wet weights, in mice following both periodic and constant dosing regimens of the rodent homolog of Sequence I.

Experimental Methods

Periodic dosing regimens of SEQ ID NO: 2, the rodent homolog of the fusion protein of SEQ ID NO: 1, were administered to mice with blood/tissue samples harvested at multiple time points to evaluate numbers (i.e., expansion) of memory phenotype CD8$^+$ T cells, NK cells, T$_{regs}$ and effects on circulating levels of cytokines (e.g. IFN$\gamma$, TNF$\alpha$ and IL-6). The dosing regimens included compound dosed once every 3 days (Q3D), once every 4 days (q4d) and once every 7 days/weekly (q7d) for a 2 to 3 week period. The daily dosing regimen consisted of once daily dosing for 5 days (qdx5) followed by 2 days 'off', which was repeated to cover a 2 week period. Body weights were measured daily during the study. Upon study completion, lung tissues were excised from all animals and weighed ("wet") once and then again subsequent to a drying procedure to calculate the net weights due to water, termed 'wet lung weights'.

Experiments were also conducted in tumor-bearing mice (MC38 tumor model) to evaluate anti-tumor efficacy for the different dosing regimens. Dosing commenced when subcutaneously implanted tumor cells grew to an average tumor size of 100 mm$^3$. Tumor size was monitored in both vehicle and compound-dosed groups, typically an n=10 in all treatment groups. The dosing regimens tested were as follows.

TABLE 1

| Group # | Test Article | Lot | Dose (mg/kg) | Dose Volume (ml/kg) | Dosing Frequency | Dosing Route | Dosing Days |
|---|---|---|---|---|---|---|---|
| 1 (n = 10) | PBS (VEH) | NA | NA | 10 | Q4d | SC | 1, 5, 9, 13, 17 |
| 2 (n = 10) | Seq ID No. 2 | Wx1 | 3 | 10 | Q3d | SC | 1, 4, 7, 10, 13, 16, 19 |

TABLE 1-continued

| Group # | Test Article | Lot | Dose (mg/kg) | Dose Volume (ml/kg) | Dosing Frequency | Dosing Route | Dosing Days |
|---|---|---|---|---|---|---|---|
| 3 (n = 10) | Seq ID No. 2 | Wx1 | 6 | 10 | Q4d | SC | 1, 5, 9, 13, 17 |
| 4 (n = 10) | Seq ID No. 2 | Wx1 | 9 | 10 | Q4d | SC | 1, 5, 9, 13, 17 |
| 5 (n = 10) | Seq ID No. 2 | Wx1 | 9 | 10 | Q7d | SC | 1, 8, 15 |
| 6 (n = 10) | Seq ID No. 2 | Wx1 | 12 | 10 | Q7d | SC | 1, 8, 15 |
| 7 (n = 10) | Seq ID No. 2 | Wx1 | 0.8 | 10 | 5/2/5/2/5 | SC | 1-5, 8-12, 15-19 |

Design of SEQ ID NO: 2:

Murine IL-2 and IL2Ra sequences were obtained (UniProtKB-P04351 and P01590 respectively) and sequence alignments of the mouse sequences and human sequences (UnitProtKB P60568 and P01589) and were used to map the mouse sequences to the circularly permuted human IL-2 sequence of SEQ ID NO: 1.

The resulting mouse ortholog of SEQ ID NO: 2 has the following amino acid sequence:

(SEQ ID NO: 2)
SKSFQLEDAENFISNIRVTVVKLKGSDNTFECQFD

DESATVVDFLRRWIAFCQSIISTSPQGGSSSTQQQ

QQHLEQLLMDLQELLSRMENYRNLKLPRMLTFKFY

LPKQATELKDLQCLEDELGPLRHVLDLTQGSGGGS

ELCLYDPPEVPNATFKALSYKNGTILNCECKRGFR

RLKELVYMRCLGNSWSSNCQCTSNSHDKSRKQVTA

QLEHQKEQQTTTDMQKPTQSMHQENLTGHCREPPP

WKHEDSKRIYHFVEGQSVHYECIPGYKALQRGPAI

SICKMKCGKTGWTQPQLTCVDGSHHHHHH.

The His-tag at the C-terminal end of SEQ ID NO: 2 is used for purification and may be present in the expressed protein or optionally may be removed. The construct used to recombinantly produce the protein may optionally include a signal peptide, for example, a signal peptide having the following amino acid sequence: MYRMQLLSCIALSLA-LVTNS (SEQ ID NO: 3).

Results

Figure 3:
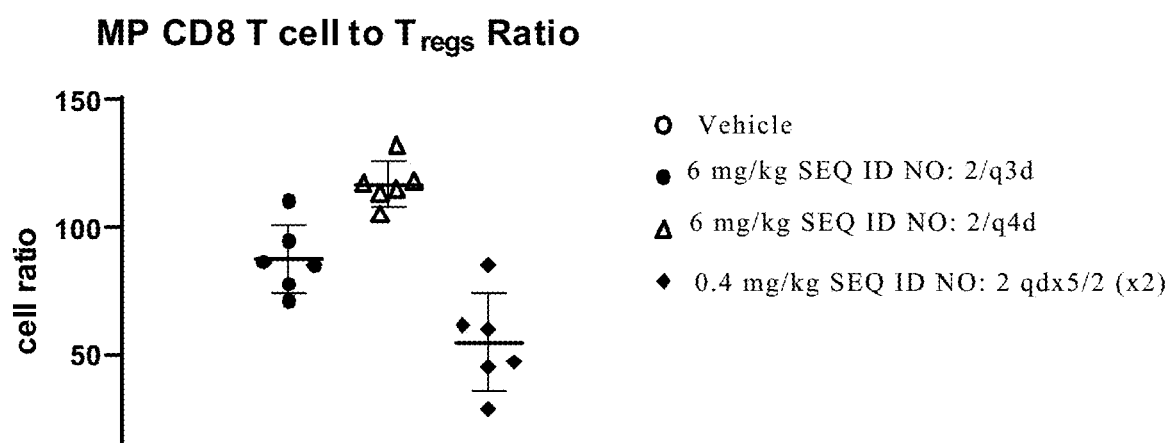
FIG. 3 is a plot graph comparing the cell ratio of CD8+ T-cells to $T_{regs}$ in FVB mice administered periodic SC dosing of SEQ ID NO: 2 at once every 3 days, once every 4 days and daily SC dosing day for 5 days with two days off.
Figure 4:
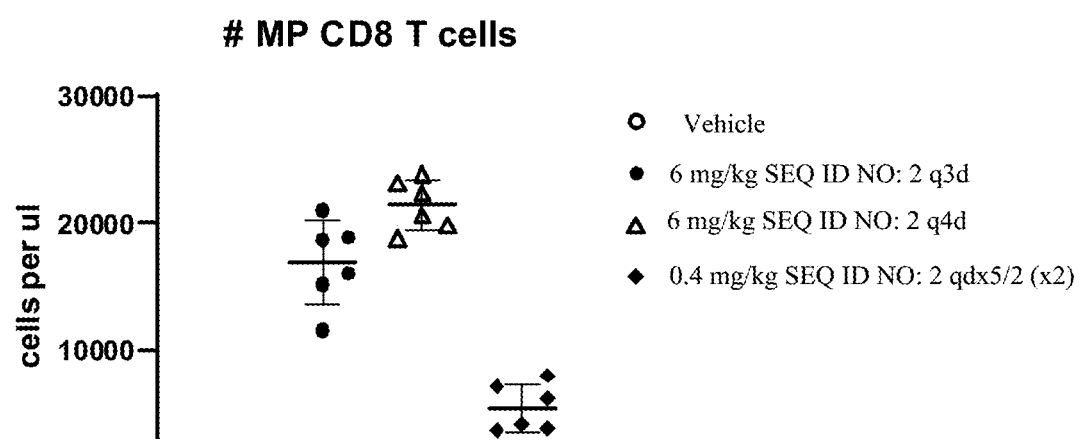
FIG. 4 is a plot graph comparing expansion of memory phenotype CD8+ T-cells in FVB mice administered periodic SC dosing of SEQ ID NO: 2 at once every 3 days and once every 4 days and daily SC dosing day for 5 days with two days off.
Figure 5:
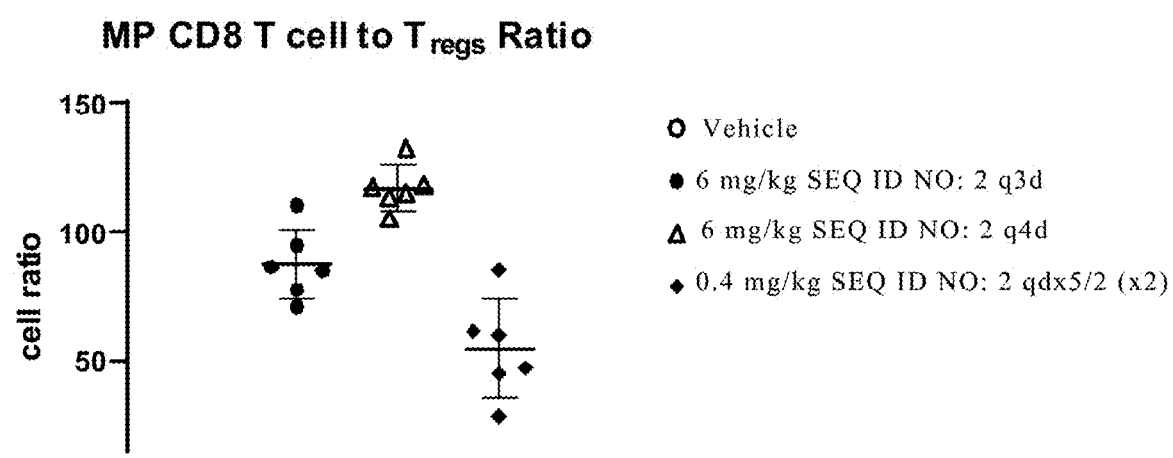
FIG. 5 is a plot graph comparing the cell ratio of memory phenotype CD8+ T-cells to $T_{regs}$ in FVB mice administered periodic SC dosing of SEQ ID NO: 2 at once every 3 days, once every 4 days and daily SC dosing day for 5 days with two days off.
Figure 6A:
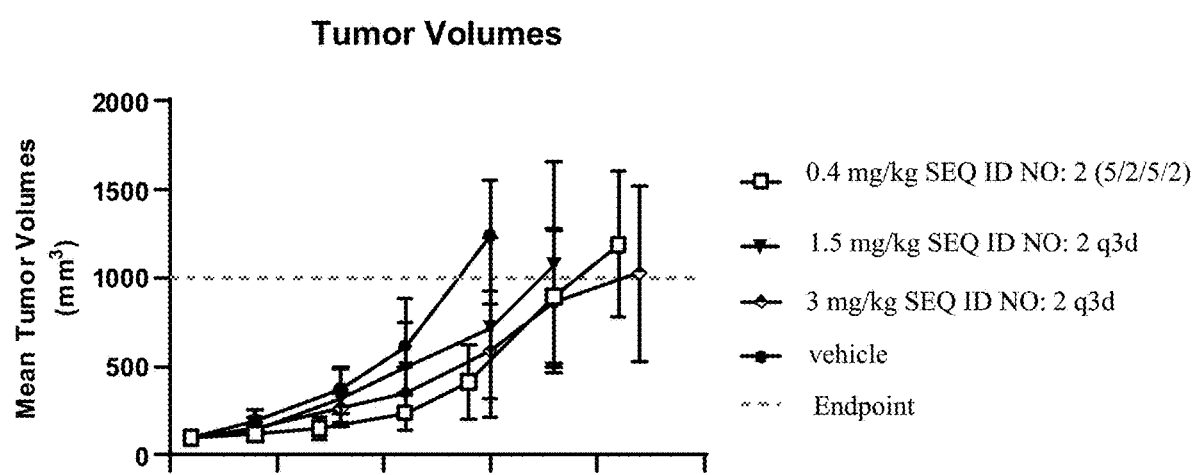
FIG. 6A is a graph comparing the anti-tumor efficacy in MC38 tumor bearing C57Bl/6 mice administered periodic SC dosing of SEQ ID NO: 2, at two different doses (1.5 mg/kg and 3 mg/kg) once every 3 days (q3d) to daily SC dosing for 5 days (qdx5) with 2 days off.
Figure 6B:
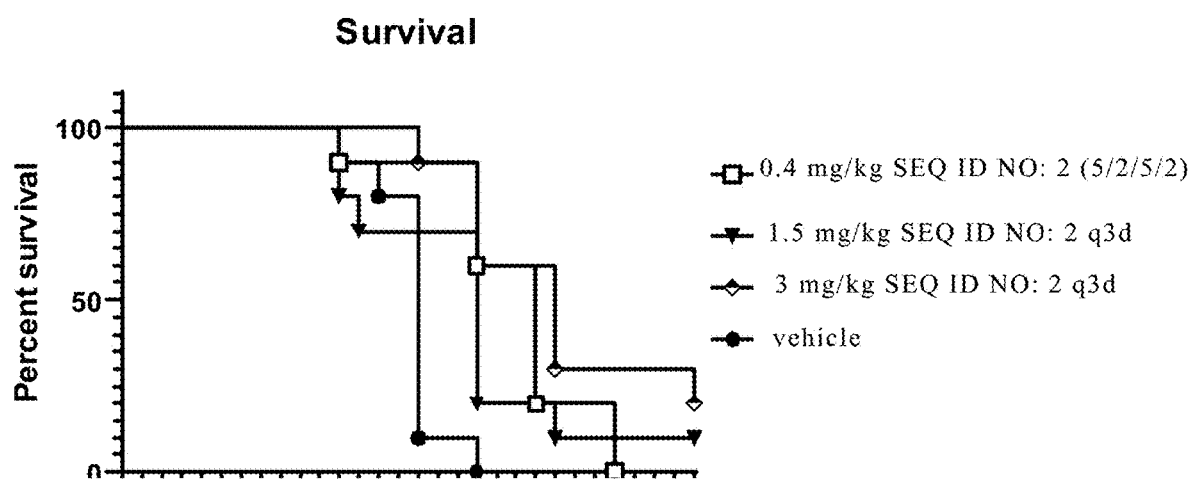
FIG. 6B is a graph comparing percent survival MC38 tumor bearing mice administered periodic SC dosing of SEQ ID NO: 2, at two different doses (1.5 mg/kg and 3 mg/kg) once every 3 days (q3d) to daily SC dosing for 5 days (qdx5) with 2 days off.
Figure 7:
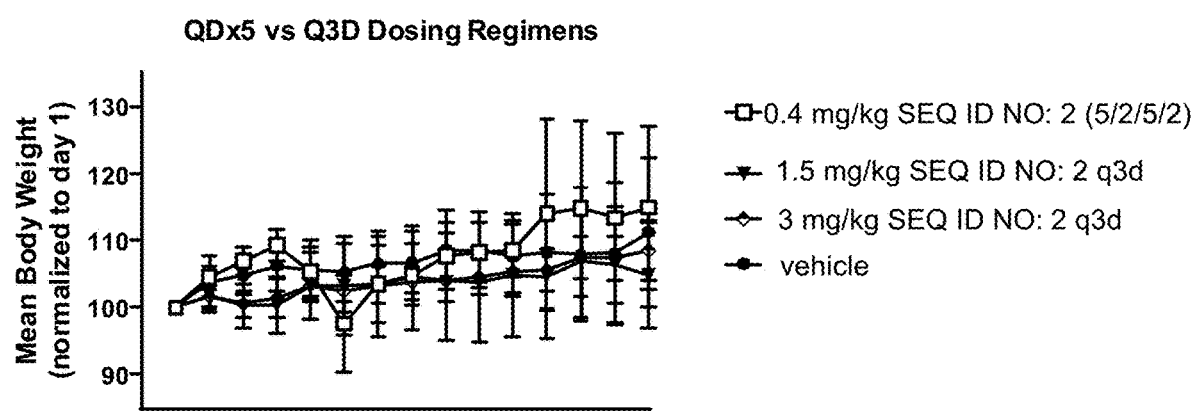
FIG. 7 is a graph comparing mean body weight of MC38 tumor bearing mice administered periodic SC dosing of SEQ ID NO: 2, at two different doses (1.5 mg/kg and 3 mg/kg) once every 3 days (q3d) to daily SC dosing for 5 days (qdx5) with 2 days off.

In general, all dosing regimens were well tolerated, with periodic dosing regimens resulting in improved measures of tolerability relative to the QDx5 dosing regimen. Periodic dosing regimens (Q3D, Q4D, Q7D) were associated with statistically greater increases in total $CD8^+$ T cells compared to the daily SC dosing regimen (FIG. 2) and increases in the ratio of CD8+ T cells to $T_{regs}$ (FIG. 3). Periodic dosing regimens (Q3D, Q4D, Q7D) were associated with statistically greater increases in memory phenotype $CD8^+$ T cells compared to the daily dosing regimen (FIG. 4) and increases in the ratios of memory phenotype CD8+ T cells to $T_{regs}$ (FIG. 5). Moreover, periodic dosing resulted in equivalent or greater anti-tumor efficacy compared to a daily dosing regimen (FIG. 6). These periodic dosing regimens showed no significant body weight loss, unlike the QDx5 regimen, which displayed a 5-10% body weight loss, with the lowest body weight observed on Day 6 of the study (FIG. 7). Of note, greater total amounts of SEQ ID NO: 2 can be delivered with improved tolerability with less frequent dosing (e.g. 0.4-0.8 mg/kg administered QDx5 results in 2-4 mg/kg per mouse total delivered in a given week; 3 mg/kg Q3D results in 9 mg/kg total administered in a 1 week period; 3 mg/kg Q4D results in 6 mg/kg total delivered in a 1 week period; 6 mg/kg Q7D is equivalent to 6 mg/kg in a 1 week period).

Figure 10:
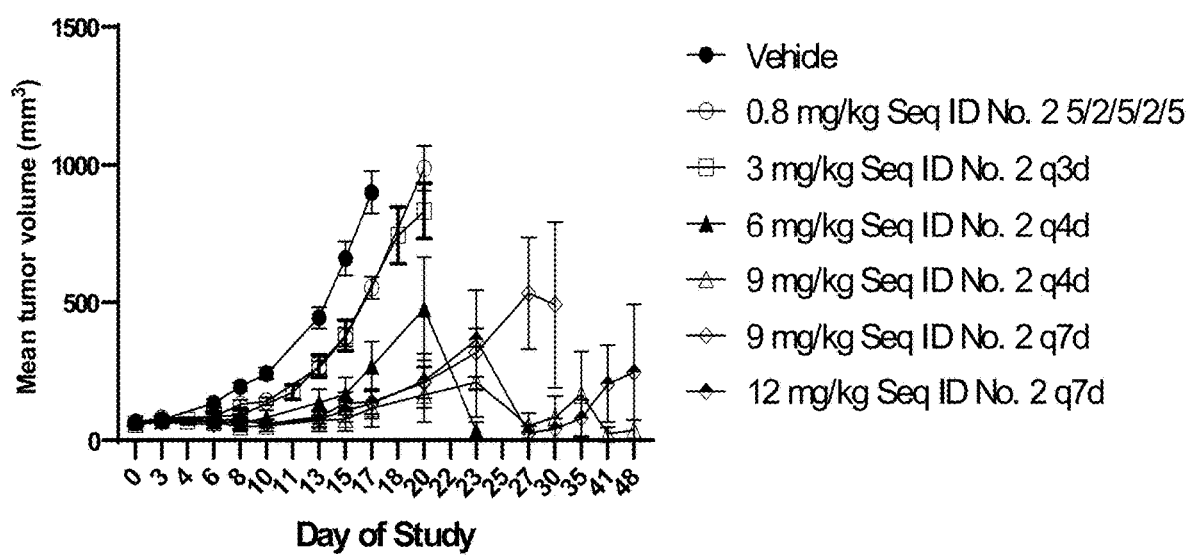
FIG. 10 is a graph comparing the anti-tumor efficacy in MC38 tumor bearing C57Bl/6 mice administered periodic SC dosing of SEQ ID NO: 2, at various doses once every 3 days (q3d) to once every 7 days (q7d) and daily SC dosing for 5 days (qdx5) with 2 days off.
Figure 11:
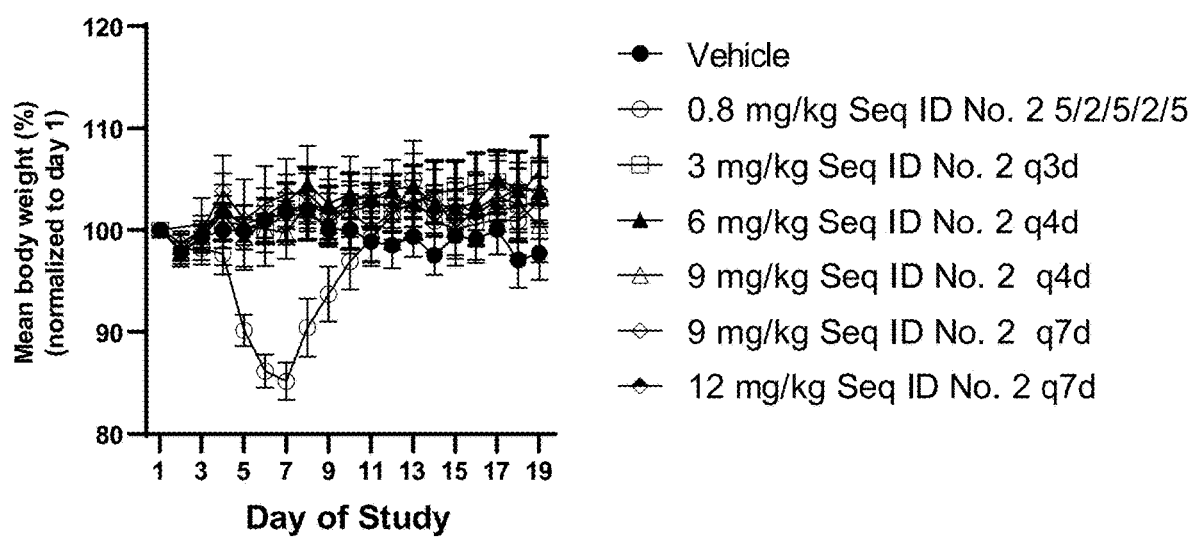
FIG. 11 is a graph comparing mean body weight in MC38 tumor bearing C57Bl/6 mice administered periodic SC dosing of SEQ ID NO: 2, at various doses once every 3 days (q3d) to once every 7 days (q7d) and daily SC dosing for 5 days (qdx5) with 2 days off
Figure 12:
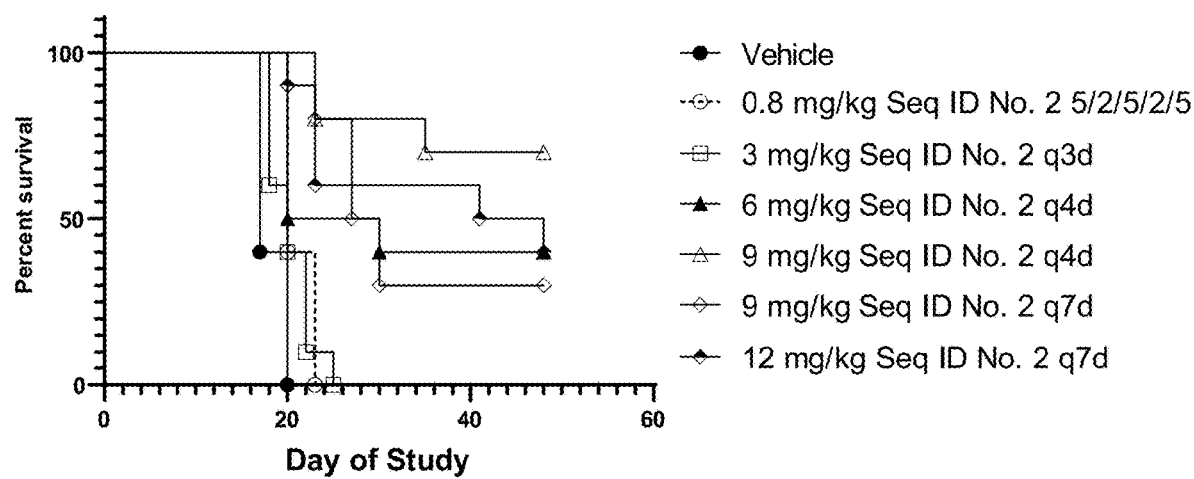
FIG. 12 is a graph comparing percent survival in MC38 tumor bearing C57Bl/6 mice administered periodic SC dosing of SEQ ID NO: 2, at various doses once every 3 days (q3d) to once every 7 days (q7d) and daily SC dosing for 5 days (qdx5) with 2 days off.

The results from the dosing regimens described in Table 1 in tumor bearing mice (MC38 Tumor Model) (FIGS. 10-12) also showed improved tolerability and improved anti-tumor efficacy as compared to the daily dosing regimen.

Conclusions

Periodic dosing regimens of the rodent homolog of SEQ ID NO: 1 are associated with a profound improvement in circulating pharmacodynamic markers, both cellular and cytokine profiles, compared to a constant dosing regimen of the rodent homolog or rIL-2. Importantly, this improved pharmacodynamic profile was associated with improvements in measures of tolerability and anti-tumor efficacy. These findings are consistent with the working hypothesis that periodic or intermittent exposure of SEQ ID NO: 1 and its rodent homolog, SEQ ID NO: 2 will provide an unexpected additional anti-tumor benefit compared to more constant dosing or sustained exposure.

Example 2—Comparison of SQ and IV Administration of SEQ ID NO: 1 in Humans

Study Protocol (Cohort 1 from Phase 1/2 Study Described in Example 3)

A study comparing escalating daily IV doses of SEQ ID NO: 1 and a periodic (q7d) subcutaneous dose of SEQ ID NO: 1 was carried out. Serum IFNγ levels and IL-6 levels were measured as described in Example 3.

Equivalent doses of IV and SC were determined by comparison of intravenous and subcutaneous exposure obtained in a post-hoc analysis of primate and human PK and PD assessments of subjects administered SEQ ID NO: 1. Briefly, the PK of SEQ ID NO: 1 after SC administration in humans were predicted using the PK data from the ongoing first-in-human clinical study described in U.S. Patent Application Ser. No. 62/860,182 in patients with advance solid tumors who received IV administration of SEQ ID NO: 1 and IV to SC scaling factor estimated based on monkey PK data. The single dose PK of SEQ ID NO: 1 evaluated in cynomolgus monkeys after IV and SC administration of SEQ ID NO: 1 were used to estimate the PK parameters in monkeys for estimation of IV to SC scaling factor.

PK profiles of SEQ ID NO: 1 in humans after SC administration of SEQ ID NO: 1 were simulated using the predicted PK parameters. The peak concentration (Cmax) of SEQ ID NO: 1 after a SC dose of 0.3 mg is predicted to be 2.6 ng/mL as compared to the observed mean Cmax of 20 ng/mL in humans after an IV dose of 1 μg/kg. The total systemic exposure over the first week (AUC0-168h) after a SC dose of 0.3 mg is predicted to be 150 ng*h/mL as compared to the AUC0-168h of 399 ng*h/mL after IV administration of 1 μg/kg/day once daily for 5 days.

In addition, a prolonged absorption phase followed by a slow elimination phase is predicted for SC administration of SEQ ID NO: 1 in humans, with Cmax predicted to be reached (Tmax) at 12 hours and terminal half-life (t1/2) predicted to be ~30 hours. In contrast, Tmax was observed at the end of the 30-min infusion for the IV administration of SEQ ID NO: 1 followed by a rapid decline of serum concentration levels with a terminal half-life of ~5 hours. In summary, a SC dose of 0.3 mg in once weekly or less frequent dosing schedule is predicted to result in peak concentration and total weekly exposure lower than that of IV administration of SEQ ID NO:1 at 1 μg/kg/day once daily for 5 consecutive days.

Results and Discussion

The data from Cohort 1 of the ongoing Phase ½ monotherapy clinical study protocol described in Example 3 showed transient elevation of serum IFNγ with minimal elevation of IL-6 at the q7d subcutaneous administration of 3 mg of SEQ ID NO: 1 as compared to the equivalent qdx5 IV administration dose of 1 μg/kg of SEQ ID NO: 1.

Figure 8:
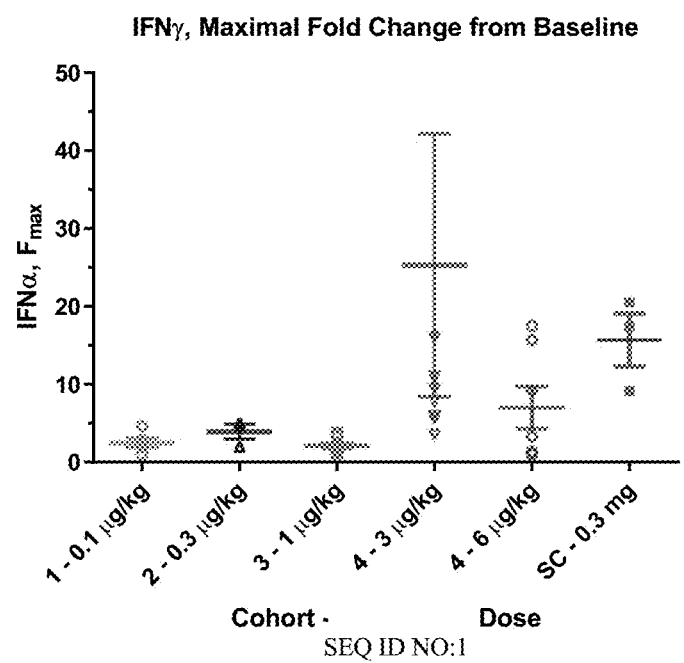
FIG. 8 is a graph comparing maximal fold change in IFNγ over baseline in human patients who have been administered with the fusion protein of SEQ ID NO: 1 at various IV doses or as a SC dose in accordance with the invention.

The maximal fold change in IFNγ cytokine levels over baseline as measured in the patient's blood serum after q7d subcutaneous administration is at least 2-fold greater than that of qdx5 intravenous administration of an equivalent dose of the fusion protein of SEQ ID NO: 1 (FIG. 8).

Figure 9:
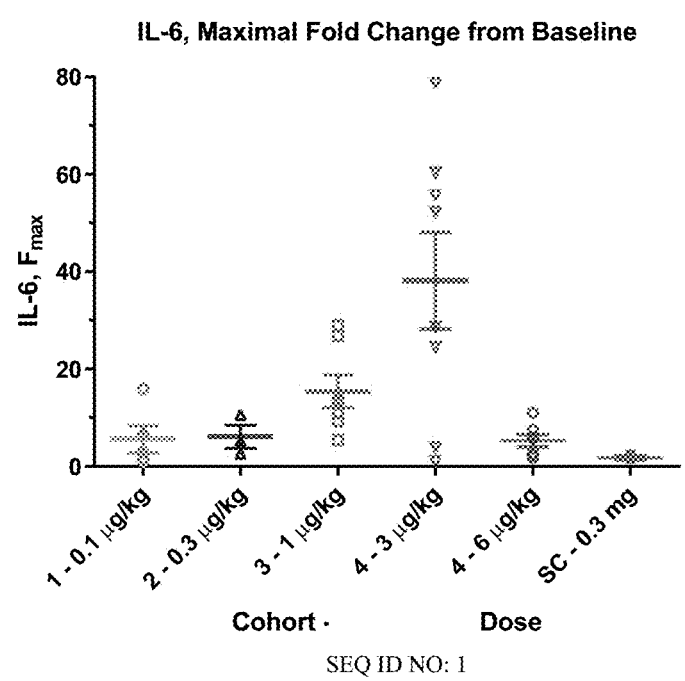
FIG. 9 is a graph comparing maximal fold change in IL-6 over baseline in human patients who have been administered with the fusion protein of SEQ ID NO: 1 at various IV doses or as a SC dose in accordance with the invention.

The maximal fold change in IL-6 cytokine levels over baseline as measured in the patient's blood serum after q7d subcutaneous administration is at least 2-fold less than that of qdx5 intravenous administration of an equivalent dose of the fusion protein of SEQ ID NO: 1 (FIG. 9).

IFNγ is a pleiotropic cytokine with anti-tumor and immunomodulatory properties. IFNγ directly acts as a cytotoxic CD8+ T cell differential signal and it is essential for the induction of cytotoxic T cell precursor proliferation. IFNγ also upregulates cell surface MEW class II on APCs thus promoting peptide-specific activation of CD4+T regulatory cells. In addition, IFNγ activates macrophages toward a pro-inflammatory profile, anti-tumor profile.

IL-6 on the other hand is a pro-inflammatory cytokine released by various cells in the tumor microenvironment including the cancerous cells. IL-6 plays a critical role in the expansion and differentiation of tumor cells. Increased levels of IL-6 in the serum and tumor site has been demonstrated in several cancers. Usually this increase is accompanied with a poor prognosis and lower survival rate. Downregulation of IL-6 has been correlated with a better response to cancer treatment.

Example 3—an Ongoing Phase ½ Study of the Fusion Protein of SEQ ID NO: 1 Administered Subcutaneously as Monotherapy and in Combination with Pembrolizumab in Subjects with Advanced Solid Tumors The fusion protein of SEQ ID NO: 1 is a fusion of circularly permuted IL-2 and IL-2 Receptor a (IL-2Rα) designed to selectively activate the intermediate-affinity IL-2R, comprised of IL-2Rβ and γ, for activation of cytotoxic CD8+ T cells and NK cells. The intermediate-affinity IL-2R is expressed predominantly on effector lymphocytes, which play an important role in driving antitumor immune responses. Wild-type IL-2 activates the high-affinity IL-2R, comprised of IL-2Rα, β, and $γ_c$, driving the expansion of immunosuppressive $T_{reg}$ cells at concentrations below those at which intermediate-affinity IL-2R-bearing effector cells are activated. Selective activation of the intermediate affinity IL-2R has the potential to enhance tumor killing and was shown to possess enhanced antitumor activity relative to IL-2 in murine models.

List of Abbreviations and Definitions of Terms

| Abbreviation or Term | Full Form of Definition |
| --- | --- |
| AE | adverse event |
| CD | cluster of differentiation |
| CR | complete response |
| CSA | Clinical Study Agreement |
| CTCAE | Common Terminology Criteria for Adverse Events |
| ctDNA | circulating tumor DNA |
| DCR | disease control rate |
| DLT | dose-limiting toxicity |
| DOR | duration of response |
| ECG | electrocardiogram |
| ECOG PS | Eastern Cooperative Oncology Group Performance Status |
| eCRF | electronic case report form |
| GCP | Good Clinical Practice |
| HCC | hepatocellular carcinoma |
| iBOR | immune best overall response |
| ICF | informed consent form |
| ICH | International Council for Harmonisation |
| iCR | immune complete response |
| iDCR | immune disease control rate |
| iDOR | immune duration of response |
| IEC | Independent Ethics Committee |
| IL | interleukin |
| IL-2R | interleukin-2-receptor |
| iORR | immune overall response rate |
| iPFS | immune progression-free survival |
| iPR | immune partial response |
| IRB | Institutional Review Board |
| iRECIST | immune Response Evaluation Criteria in Solid Tumors |
| iSD | immune stable disease |
| iTTR | immune time to response |
| iUPD | immune unconfirmed progressive disease |

Protocol SEQ ID NO: 1—

| Abbreviation or Term | Full Form of Definition |
| --- | --- |
| IV | intravenous(ly) |
| MTD | maximum tolerated dose |
| NCI | National Cancer Institute |
| NK | natural killer [cells] |
| NSCLC | non-small-cell lung cancer |
| ORR | overall response rate |
| PD | pharmacodynamic(s) |
| PD-1 | programmed death receptor-1 |
| PD-L1 | programmed death ligand-1 |
| PFS | progression-free survival |
| PK | pharmacokinetic(s) |
| PR | partial response |
| q7d | every 7 days |
| q21d | every 21 days |
| RECIST | Response Evaluation Criteria in Solid Tumors |
| RP2D | recommended Phase 2 dose |
| SAE | serious adverse event |
| SAP | Statistical Analysis Plan |
| SC | subcutaneous(ly) |
| SCCHN | squamous cell carcinoma of the head and neck |
| SCLC | small-cell lung cancer |

-continued

| Abbreviation or Term | Full Form of Definition |
|---|---|
| SD | stable disease |
| SRC | Safety Review Committee |
| TEAE | treatment-emergent adverse event |
| TIL | tumor-infiltrating lymphocyte |
| TME | tumor microenvironment |
| Tregs | T regulatory cells |
| TTR | time to response |
| ULN | upper limit of normal |
| USPI | United States prescribing information |
| WHO-ATC | World Health Organization-Anatomical Therapeutic Chemical (classification system) |
| WOCBP | women of childbearing potential |

Overall Study Design and Plan

This is a Phase ½ study that is ongoing. The study is being conducted in 2 phases: Phase 1 is a dose-escalation phase with multiple ascending doses of SC SEQ ID NO: 1 as lead-in monotherapy followed by combination with pembrolizumab. Phase 2 is a dose-expansion phase with SC SEQ ID NO: 1 administered at the RP2D (determined from Phase 1) in combination with pembrolizumab.

Phase 2 will enroll subjects into 1 of 5 cohorts based on 4 specific tumor types and 1 specific tumor histology. Subjects may remain on study treatment until confirmed progressive disease, intolerance to SC SEQ ID NO: 1, removal by the Investigator, subject request, or any of the other criteria for study discontinuation. At a minimum, subjects are eligible to receive treatment with the study regimen for as long as the subject is deriving clinical benefit.

Phase 1 Dose Escalation

The serum PK of SEQ ID NO: 1 and presence of anti-SEQ ID NO: 1 antibodies was determined. In addition, PD effect of SEQ ID NO: 1 was assessed throughout the study based on measurement of circulating $CD8^+$ T cells, $T_{regs}$, and NK cells in blood, as well as serum levels of certain cytokines. Safety evaluation was based on AEs, vital signs, clinical laboratory tests, and electrocardiograms. The severity of AEs was assessed using the NCI CTCAE version 5.0.

In Phase 1, following a 21-day screening window, subjects entered the 6-week monotherapy lead-in period. Subjects were treated with SC SEQ ID NO: 1 in 1 of 2 different dosing schedules (q7d and q21d). After 6 weeks of monotherapy lead-in treatment, if the subject has tolerated SEQ ID NO: 1, treatment with pembrolizumab 200 mg every 3 weeks will be added to the ongoing SC SEQ ID NO: 1 regimen. Subjects receiving combination treatment with SC SEQ ID NO: 1 and pembrolizumab will continue to receive treatment with the study regimen for as long as the subject derives clinical benefit or until the occurrence of any of the other criteria for treatment discontinuation or study discontinuation.

The monotherapy starting dose and regimen was 0.3 mg q7d (Cohort 1). AS no DLT was observed in the first 3 evaluable subjects or no more than 1 DLT was observed in the first 6 evaluable subjects, enrollment in Cohort A2 (1.0 mg q7d) and Cohort B2 (1.0 mg q21d) began.

From the point at which subjects are enrolled in Cohorts A2 and B2 onward, enrollment in the 2 dosing schedule cohort tracks (ie, q7d and q21d) will proceed independently. Dose escalation along a cohort track will occur only after the preceding dose in that track has been determined to be adequately tolerable, as described above.

Each cohort will be evaluated for safety and tolerability using a 3+3 study design with allowance for over-enrollment with 4 to 7 subjects and a minimum of 3 evaluable subjects per cohort to receive SC SEQ ID NO: 1 at the specified dose and schedule. The highest dose level cohort (q7d or q21d) will enroll up to 6 to 7 subjects.

Doses in subsequent cohorts will be escalated up to 30 mg/injection as shown in FIG. 3 or until the RP2D is identified or the maximum tolerated dose (MTD) is reached. Data for dose escalation up to 3 mg per dose SC is provided in Example 4.

Dose-limiting toxicities are defined by any of the following events possibly, probably, or definitely related to SC SEQ ID NO: 1 that are observed during the first 28 days of SC SEQ ID NO: 1 lead-in monotherapy:

Grade 4 neutrophil count decreased (neutropenia) that has not recovered to Grade 2 ($\geq 1000$ cells/mm$^3$) before the next scheduled dose or requires an urgent intervention (eg, use of hematopoietic colony-stimulating factors) or is associated with clinically significant infection. Dosing with SC SEQ ID NO: 1 in the current cycle will not be stopped due to neutropenia in the absence of urgent intervention or clinically significant infection.

Febrile neutropenia (absolute neutrophil count [ANC] <1000 cells/mm$^3$ with temperature >38.3° C. [101° F.]) that persists for more than 48 hours or requires an urgent intervention (eg, use of hematopoietic colony-stimulating factors) or is associated with clinically significant infection.

Grade 4 thrombocytopenia that does not recover to Grade ≤2 before the next dose.

Thrombocytopenia with a platelet count <30,000 with clinically significant bleeding.

Any Grade 3 cardiac or central nervous system toxicity.

Liver transaminase elevation higher than 8×ULN or total bilirubin higher than 6×ULN that does not recover to Grade ≤2 or baseline within 1 week.

Grade 4 hypoalbuminemia.

Fever >40° C. sustained for >24 hours unrelated to ongoing infection.

Hypotension requiring use of pressors (e.g., phenylephrine or dopamine administered for the purpose of increasing blood pressure) or prolonged hospitalization (>48 hours) for hypotension requiring medical intervention.

Increase in amylase or lipase that meets the following criterion.

>3×ULN with acute severe abdominal pain (other mild symptoms at Grade 3 will not be considered as DLTs).

Grade 3 or higher nausea, vomiting, or diarrhea lasting longer than 48 hours despite maximum supportive care.

Any other Grade 4 non-hematologic toxicity or any other Grade 3 non-hematologic toxicity that does not resolve to Grade ≤2 within 96 hours, other than fatigue or anorexia. Fatigue or anorexia will not be considered DLTs.

Any other toxicity or AE not defined above that results in subject removal from the study or permanent discontinuation of dosing by the Investigator (dose delays during Cycle 2 or later are not considered DLTs).

Any laboratory value that meets the DLT criteria as described above must be confirmed with a second result for DLT criteria to be met.

Based on the interpretation of PK, PD, preliminary anti-tumor activity, and safety data (including AEs observed after the initial 4-week DLT observation period), a single dose level (i.e., mg/injection) and dosing schedule (i.e., q7d or q21d) of SC SEQ ID NO: 1 treatment will be selected for further evaluation in combination with pembrolizumab in the expansion phase of the study (i.e., the RP2D). The RP2D will be equal to or less than the MTD.

If the RP2D has not been reached within the proposed dose range, additional dose escalations will be considered and will be added to the study via a protocol amendment. Additional cohorts with dose levels below the DLT level may be evaluated to determine the MTD for each dosing schedule (i.e., q7d and q21d). Prior to any dose escalation, the Principal Investigators who have enrolled subjects on the study, the Sponsor's Medical Monitor, and certain other representatives from the Sponsor (the Safety Review Committee [SRC]) will review the safety data from the current cohort and will decide if dose escalation is warranted.

Dose escalation in one of the dosing schedule cohort tracks (i.e., q7d or q21d) will be discontinued if the other dosing schedule demonstrates superior tolerability, antitumor activity, and/or PD responses.

An individual subject participating in Phase 1 of the study may be permitted to have his/her dose escalated (i.e., intrasubject dose escalation) if the subject meets specific criteria. Such escalations would increase the subject's dose to the protocol-defined dose level that is one level higher than the subject's current dose level.

Subjects without a DLT who receive fewer than the protocol-specified number of doses during the DLT evaluation period (ie, less than 4 for q7d or less than 2 for q21d regimens) will be replaced at the same dose level if the minimum number of evaluable subjects has not been reached for the cohort. However, the subject may remain in the study if the Investigator feels the risk/benefit ratio is acceptable.

Following the initial 4-week DLT observation period, safety and tolerability will continue to be monitored closely. Adverse events meeting DLT criteria but arising after the subject's DLT observation period has concluded may be reviewed by the SRC and may lead to decisions to cease further dose escalation in the monotherapy lead-in phase and/or to de-escalate doses in the combination phase.

Once the MTD/RP2D is defined, a safety expansion cohort may be added before starting Phase 2. Up to 12 additional subjects may be treated to evaluate the combination of SEQ ID NO: 1 and pembrolizumab administered concomitantly starting from Cycle 1 Day 1. The purpose of this MTD/RP2D expansion cohort is to characterize the safety and tolerability of the combination regimen and to confirm the RP2D before enrolling subjects into the Phase 2 expansion cohorts. If approximately one third or more of the subjects treated in the MTD expansion cohort experience a DLT or if the integrated cohort assessment merits, a lower dose level may be assessed.

After the last patient in a cohort has completed the 28-day DLT observation period, the Sponsor and Clinical Research Organization Medical Monitor and Investigators will meet to review all available safety data. Based on this review, any of the following actions may be taken with either one or both schedules of administration (q7d or q21d), to gain additional safety data:
  Halt or continue dose escalation as defined per protocol
  Expand the current dose level in either one or both schedules of administration
  De-escalate to a dose (e.g., 0.1 mg or 0.2 mg) lower than the starting dose level
  Explore a dose that is intermediate between the current dose and the previous dose level
  Explore a dose that is intermediate between the current dose and the next higher dose level as defined in the protocol.

At the conclusion of dose escalation, either the q7d or the q21d schedule will be selected as the go-forward schedule based on a review of available data by the Safety Review Committee Phase 2 Dose Expansion In Phase 2, following a 21-day screening window, subjects with the following tumor types and specific histology will be enrolled into the following cohorts:
  NSCLC
  SCCHN
  Squamous tumor agnostic
  HCC
  SCLC.

Subjects will receive treatment with the RP2D and recommended dosing schedule identified in Phase 1 of SC SEQ ID NO: 1 in combination with pembrolizumab 200 mg every 3 weeks (Subjects receiving combination treatment with SC SEQ ID NO: 1 and pembrolizumab will continue to receive treatment with the study regimen for as long as the subject is deriving clinical benefit.

Study Drug Dose and Administration

Sites must have written procedures in place detailing the healthcare personnel required to be on site during subject dosing, the availability of equipment and medications necessary to treat an emergency (should it occur), and the process for transferring a subject to a medical facility if necessary. Emergency resuscitation equipment should be available.

SEQ ID NO: 1 Dosing and Administration

During the monotherapy lead-in of Phase 1, the SEQ ID NO: 1 regimen consists of 1 treatment day of SC SEQ ID NO: 1 either q7d (±1 day) or q21d (±1 day). During combination therapy in Phase 1 or 2, all treatment cycles are every 3 weeks. For the q7d dosing schedule, SC SEQ ID NO: 1 will be administered on Days 1, 8, and 15 of each cycle with a window (±1 day), and pembrolizumab will be administered on Day 1 (±1 day) of each cycle. For the q21d dosing schedule, SC SEQ ID NO: 1 and pembrolizumab are administered on Day 1 (±3 days) of each q3w cycle; however, SC SEQ ID NO: 1 dosing must stay aligned with pembrolizumab.

SEQ ID NO: 1 will be administered by SC injection q7d and q21d, continuing for as long as subjects are deriving clinical benefit. Injection-site locations will include the back of the arm, the thigh, or the abdomen.

On Day 1 of the monotherapy lead-in period, an observation period of 8 hours following the SC SEQ ID NO: 1 injection will be required. Subjects may be observed for less time during subsequent injections.

In Phase 1 or 2, on days where SC SEQ ID NO: 1 is administered in combination with pembrolizumab, SEQ ID NO: 1 should be administered as an SC injection 60 to 90 minutes prior to the pembrolizumab infusion. Subjects will be monitored for at least 1 hour for potential acute reactions to SEQ ID NO: 1 prior to administration of pembrolizumab.

Pembrolizumab Dosing and Administration

Pembrolizumab is to be administered as an IV infusion over 30 minutes in a dose of 200 mg every 3 weeks for as long as subjects are deriving clinical benefit (i.e., objective response or stable disease [SD]), in accordance with the prescribing information (Keytruda USPI). Pembrolizumab is available as single-dose vials of either lyophilized powder or solution.

Infusion- and Injection-Site Reactions

SEQ ID NO: 1 administered by SC injection may be associated with local injection-site reactions. Injection-site reactions should be treated at the discretion of the Investigator. Subjects who experience Grade 3 injection-site reactions may be rechallenged with SC SEQ ID NO: 1 after consultation with the Medical Monitor. Grade 4 injection-site reactions should not be rechallenged with SC SEQ ID NO: 1.

Infusion-related reactions associated with the use of pembrolizumab should be managed in accordance with the prescribing information for pembrolizumab (Keytruda USPI). SEQ ID NO: 1 drug product is supplied in 2 mg, 10 mg, and 30 mg single-dose vials that, when reconstituted, result in a clear, colorless solution of SEQ ID NO: 1 of 1 mg/mL, 5 mg/mL, and 15 mg/mL, respectively.

SEQ ID NO: 1 is supplied as a sterile, white to off-white, lyophilized powder and is supplied separately with sterile 0.32% sodium chloride diluent (SC saline diluent) for reconstitution.

Following completion of the SC SEQ ID NO: 1 monotherapy lead-in period in Phase 1, if the subject has tolerated therapy, pembrolizumab will be added. Pembrolizumab is administered as an IV infusion over 30 minutes in a dose of 200 mg every 3 weeks. Pembrolizumab will also be administered with SC SEQ ID NO: 1 in Phase 2. Pembrolizumab will be obtained from the study sites' pharmacies from commercial supplies or provided by Sponsor in countries where pembrolizumab is not yet approved. The Directions for Use will be distributed to the study centers and detailed dose preparation, handling, and administration instructions will be provided.

Assessment of Efficacy
Primary Efficacy Endpoint

During Phase 2, ORR will be determined for each of 5 cohorts (NSCLC, SCCHN, squamous tumor agnostic, HCC, and SCLC) per RECIST.

Secondary Efficacy Endpoint(s)
Tumor Assessments

Antitumor activity will be determined by the measurement of the extent of neoplastic disease at baseline and approximately every 9 weeks. (After Cycle 10, this should be reduced to every 12 weeks.) Appropriate radiological procedures (computed tomography scanning, magnetic resonance imaging, and radionuclide imaging) should be conducted to evaluate areas of neoplastic disease. Superficial skin tumors will be measured with calipers and photographed for evaluation. It is requested that the initial method of measurement be maintained throughout the course of the study. The determination of response will be conducted according to the standard RECIST criteria as well as the iRECIST. Tumors are assessed as complete response (CR)/immune CR (iCR), partial response (PR)/immune PR (iPR), SD/immune SD (iSD), or progressive disease/immune progressive disease (iPD). Refer to the guidelines for RECIST and iRECIST for definitions for each of these tumor assessments. For the purposes of this study, subjects must meet the definition for SD/iSD for a minimum of 12 weeks before an assessment of SD/iSD can be determined.

In studies with immunotherapeutic agents, CR, PR, or SD may not occur until after an increase in tumor burden characterized as progression of disease by RECIST criteria. The conventional response criteria such as RECIST may not adequately assess the activity of immunotherapeutic agents. Progressive disease evaluated radiologically may not mean therapeutic failure, as responses to immune therapies may occur after conventional PD. The appearance of measurable antitumor activity may take longer for immune therapies than for cytotoxic therapies.

With immunotherapeutic agents, there should be allowance for clinically insignificant progression of disease, defined as small new lesions in the presence of other responsive lesions, which may occur even though the subject is responding to the immunotherapy. Stable disease may also represent antitumor activity with iRECIST. Therefore, RECIST and iRECIST will be used to ensure a more comprehensive evaluation of tumor response for SC SEQ ID NO: 1.

Antitumor activity will be expressed as the ORR or immune ORR (iORR) based on RECIST and iRECIST. All target and nontarget lesions will be measured radiographically or by using a photo for superficial skin tumors. Overall tumor response rate will be determined. The ORR/iORR is the number of subjects exhibiting a CR/iCR or PR or iPR divided by the number of subjects evaluable for antitumor activity. Duration of response will also be determined. The ORR/iORR will be calculated separately for subjects in the dose-escalation portion of the study and in the dose-expansion combination therapy phase of the study (Phase 2).

Assessment of PK, PD and Immunogenicity
Pharmacokinetics

Serum samples for evaluation of SC SEQ ID NO: 1 PK will be obtained at predetermined time points. A validated electrochemiluminescence method will be used for the quantitation of SEQ ID NO: 1 in human serum. Noncompartmental PK analysis will be performed to estimate the PK parameters for SEQ ID NO: 1. Remaining serum PK samples obtained during scheduled PK blood draws in Phase 2, may be analyzed for pembrolizumab concentrations at a future date.

Immunogenicity

Data on the presence of anti-SEQ ID NO: 1 antibodies will be summarized by treatment cohort/dose level. Remaining serum samples will be stored for potential analysis of anti-pembrolizumab antibody induction at a future date.

Pharmacodynamics and Biomarkers

The PD response of various biomarkers will be assessed in blood and serum samples collected from all subjects in the study. Plasma samples will also be collected for isolation of circulating tumor DNA (ctDNA) from subjects in Phase 2; those 10-mL samples will be taken at screening, predose on Cycle 1 Day 8, predose on Cycle 2 Day 1, predose on Cycle 3 Day 1, end-of-treatment, and at time of progression among subjects who experienced CR, PR, or SD. Additional biomarker analyses including PD-L1 expression may be performed on tumor tissue samples. DNA from the baseline fecal samples collected from phase 2 subjects will also be isolated and can be used for correlative analysis.

Blood-Based Biomarkers

Blood samples for the assessment of the PD effect of SC SEQ ID NO: 1, as measured by circulating $CD8^+$ T cells, $T_{regs}$, and NK cells in peripheral blood, will be obtained from each subject at predetermined time points. Validated biomarker assays will be used for the measurement of numbers as well as activity of circulating $CD8^+$ T cells, $T_{regs}$, and NK cells in peripheral blood. Expression of IL-2 receptors on immune cells will also be assessed.

Circulating tumor DNA isolated from plasma may be subject to genetic and epigenetic analysis. In addition, serum samples for assessment of serum cytokine levels will be obtained from each subject at predetermined time points. Concentration of multiple proinflammatory cytokines including interferon-γ, tumor necrosis factor-α, IL-1, IL-6, and IL-10 will be determined using a validated cytokine assay kit.

Tumor Tissue Biomarkers
Tumor Biopsies

Collection of fresh tumor samples via biopsy is optional but encouraged during the study. Subjects with accessible tumors who are willing to undergo biopsy should provide samples at screening (both phases) and while on treatment during Days 29 to 33 in the monotherapy lead-in period (Phase 1 only) and during Cycle 2 Days 8 to 14 in the combination therapy period (both phases). These samples will be analyzed by immunohistochemistry and/or immunofluorescence for markers of immune activation. They can also be used for gene expression analysis using method such as NanoString. Comparison of on-treatment versus baseline results can be used to demonstrate the pharmacologic impact to tumor microenvironment. The analysis of the baseline tumor tissues will be used for correlative analysis. Refer to the Laboratory Manual for tumor sample handling and processing information.

Example 4: Results from Phase I Dose Escalation Study

As discussed in Example 3, initial results from dose escalation to a dose of up to 3 mg administered q7d and q21d was obtained wherein the 3 mg cohort comprised 2 individuals with up to 7 individuals currently undergoing enrollment. The data obtained includes the data shown in FIGS. 13-17.

Pharmacokinetics of SEQ ID NO: 1 after Subcutaneous (SC) Administration

Figure 13:
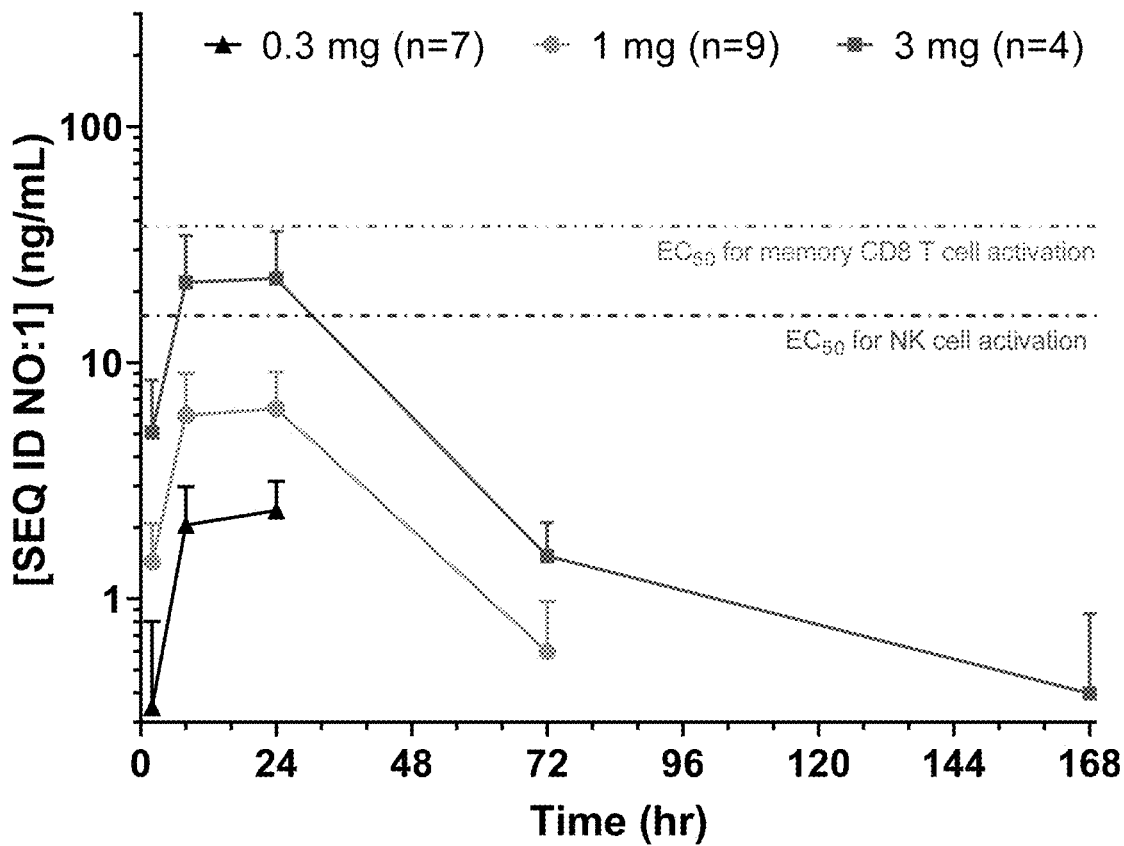
FIG. 13 is a graph comparing mean (±standard deviation) serum concentrations (ng/mL) of SEQ ID NO: 1 in patients with advanced solid tumors after the first SC dose of SEQ ID NO: 1.
Figure 14:
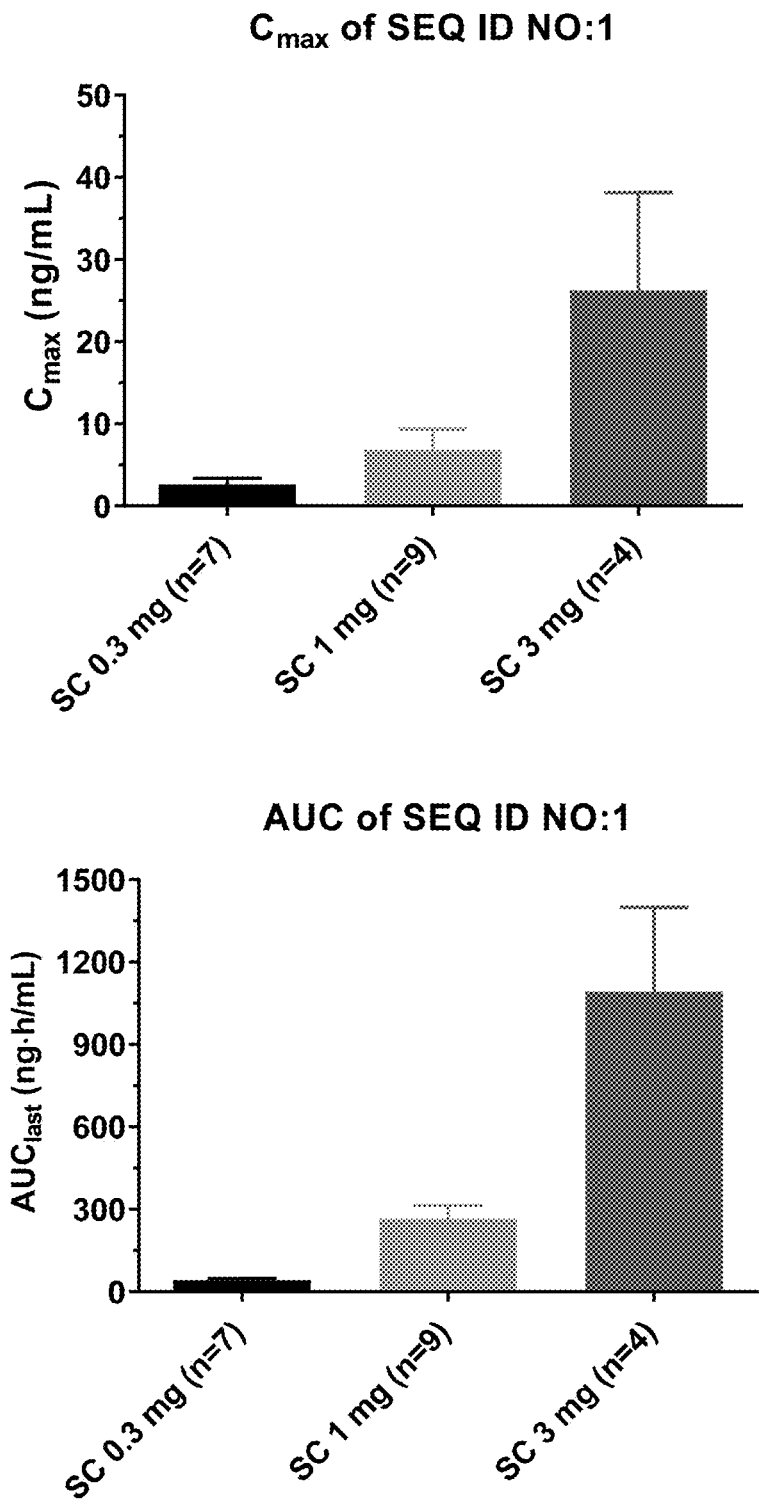
FIG. 14 is a graph comparing mean (±standard error) maximum serum concentration ($C_{max}$) and area under the concentration vs. time curve from time 0 to the last measurable concentration ($AUC_{last}$) in patients with advanced solid tumors after the first SC dose of SEQ ID NO: 1.

SEQ ID NO: 1 serum concentration vs time profiles after the first SC dose of SEQ ID NO: 1 (monotherapy lead-in Cycle 1 Day 1) are depicted in FIG. 13. Mean peak ($C_{max}$) and total serum exposure ($AUC_{last}$) of SEQ ID NO: 1 over the dose range of 0.3 mg to 3 mg are shown in FIG. 14. After a single SC dose of SEQ ID NO: 1, peak serum SEQ ID NO: 1 concentrations were reached between 8 and 24 hours post dose then declined slowly with measurable concentrations up to 168 hours (7 days) post dose at 3 mg dose. Systemic exposure to SEQ ID NO: 1 ($C_{max}$ and $AUC_{last}$) increased with increase in dose. The increase in $C_{max}$ was approximately dose proportional and the increase in $AUC_{last}$ was greater than dose proportional over the dose range 0.3 mg to 3 mg.

Pharmacodynamic Effects of SEQ ID NO: 1 after SC Administration

Figure 15:
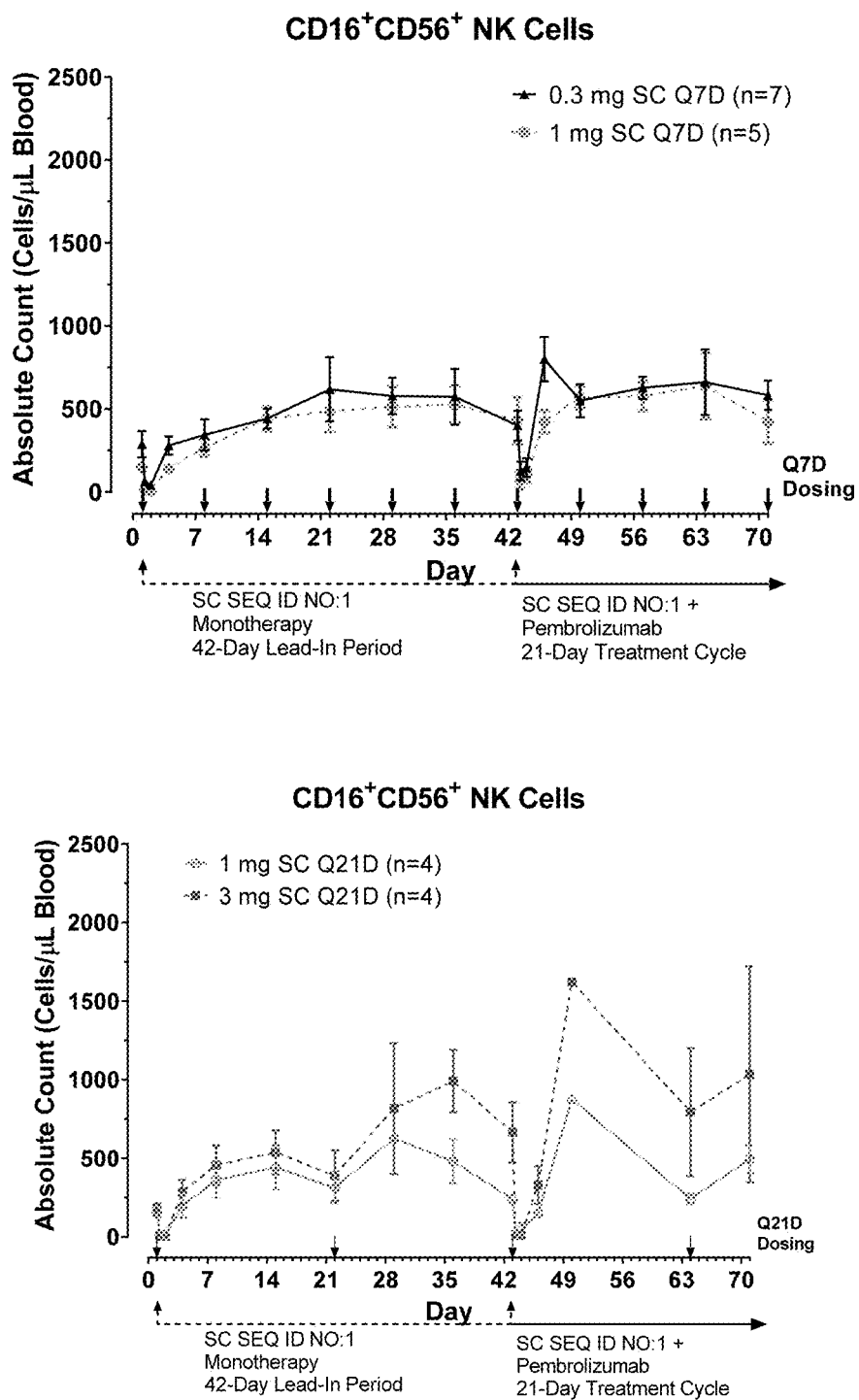
FIG. 15 are graphs comparing mean (±standard error) absolute counts (cells/μL blood of total NK cells, total CD8+ T cells and $T_{regs}$ in patients with advanced solid tumors after SC administration of SEQ ID NO: 1 on q7d or q21d.
Figure 15:
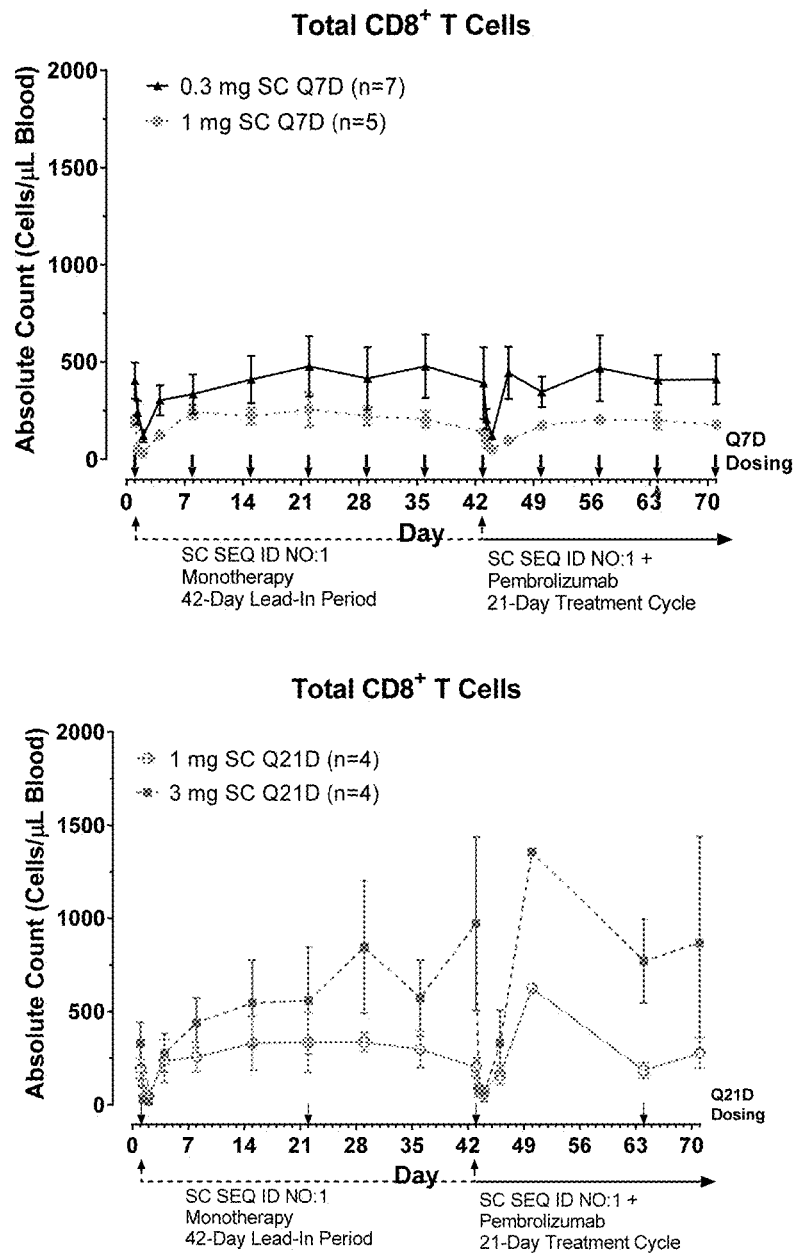
Figure 15:
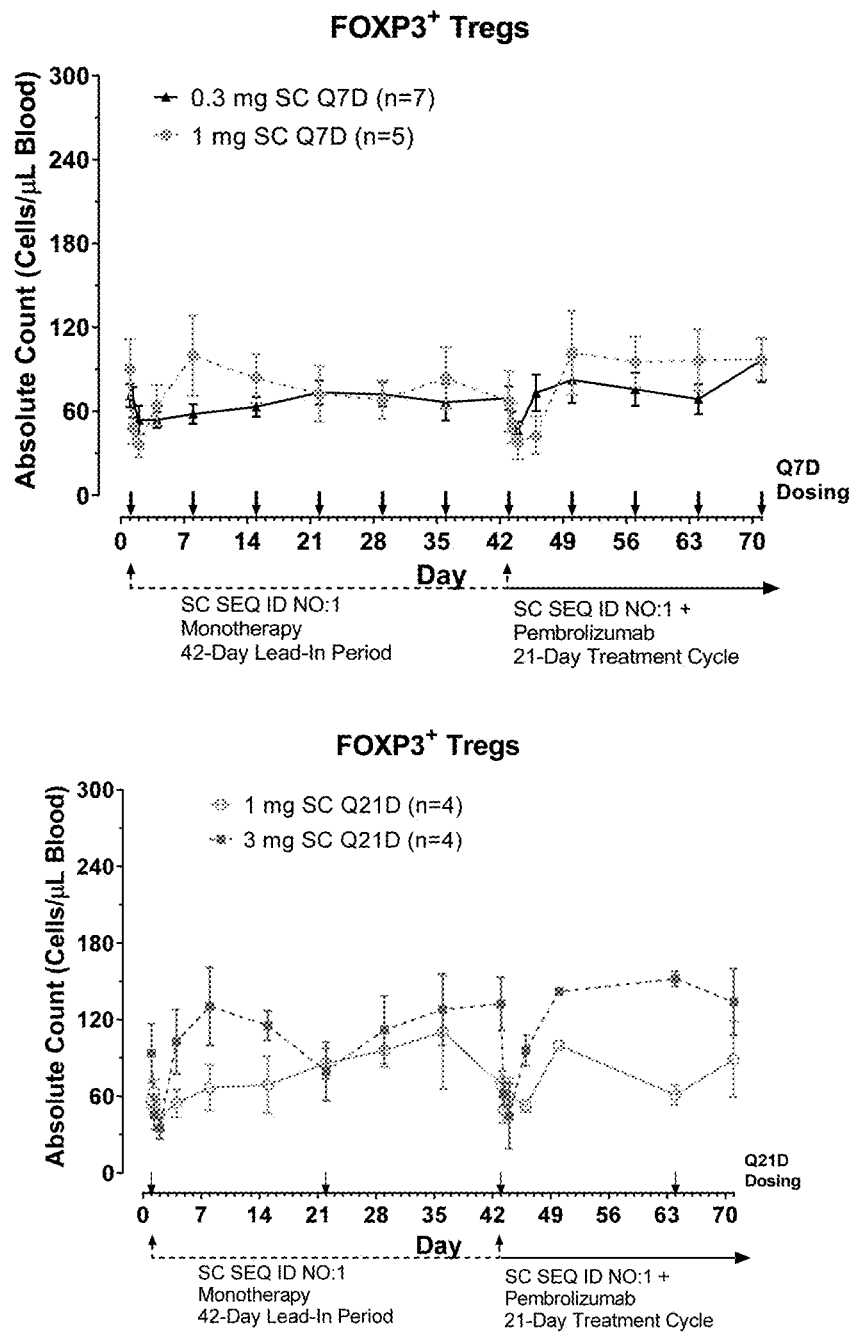
Figure 16:
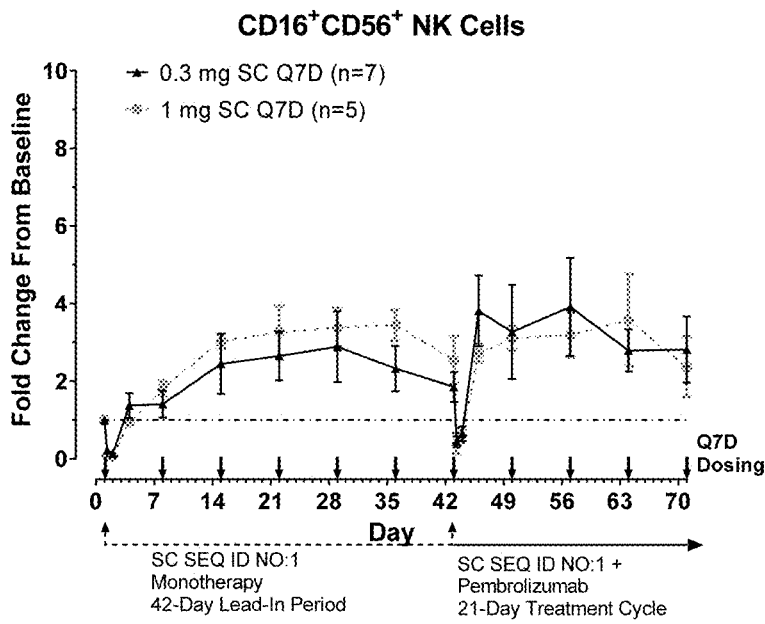
FIG. 16 are graphs comparing mean (±standard error) fold change from baseline in absolute counts (cells/μL blood of total NK cells, total CD8+ T cells and $T_{regs}$ in patients with advanced solid tumors after SC administration of SEQ ID NO: 1 on q7d or q21d.
Figure 16:
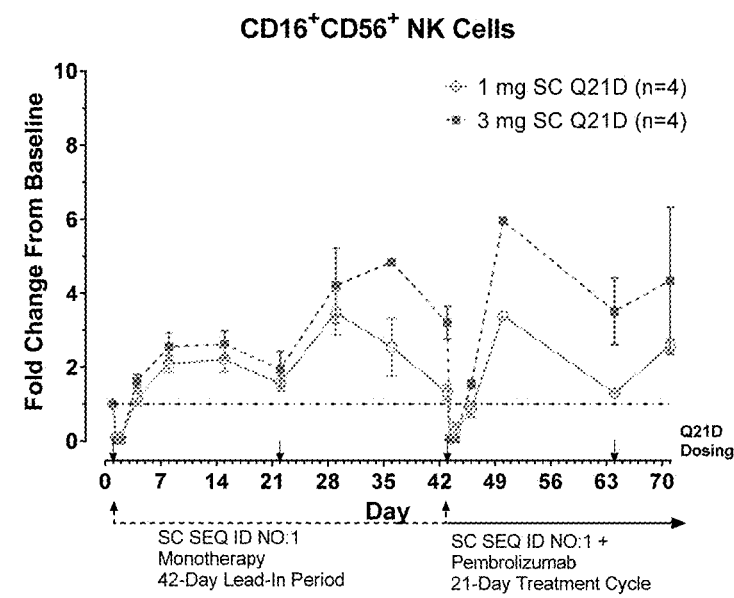
Figure 16:
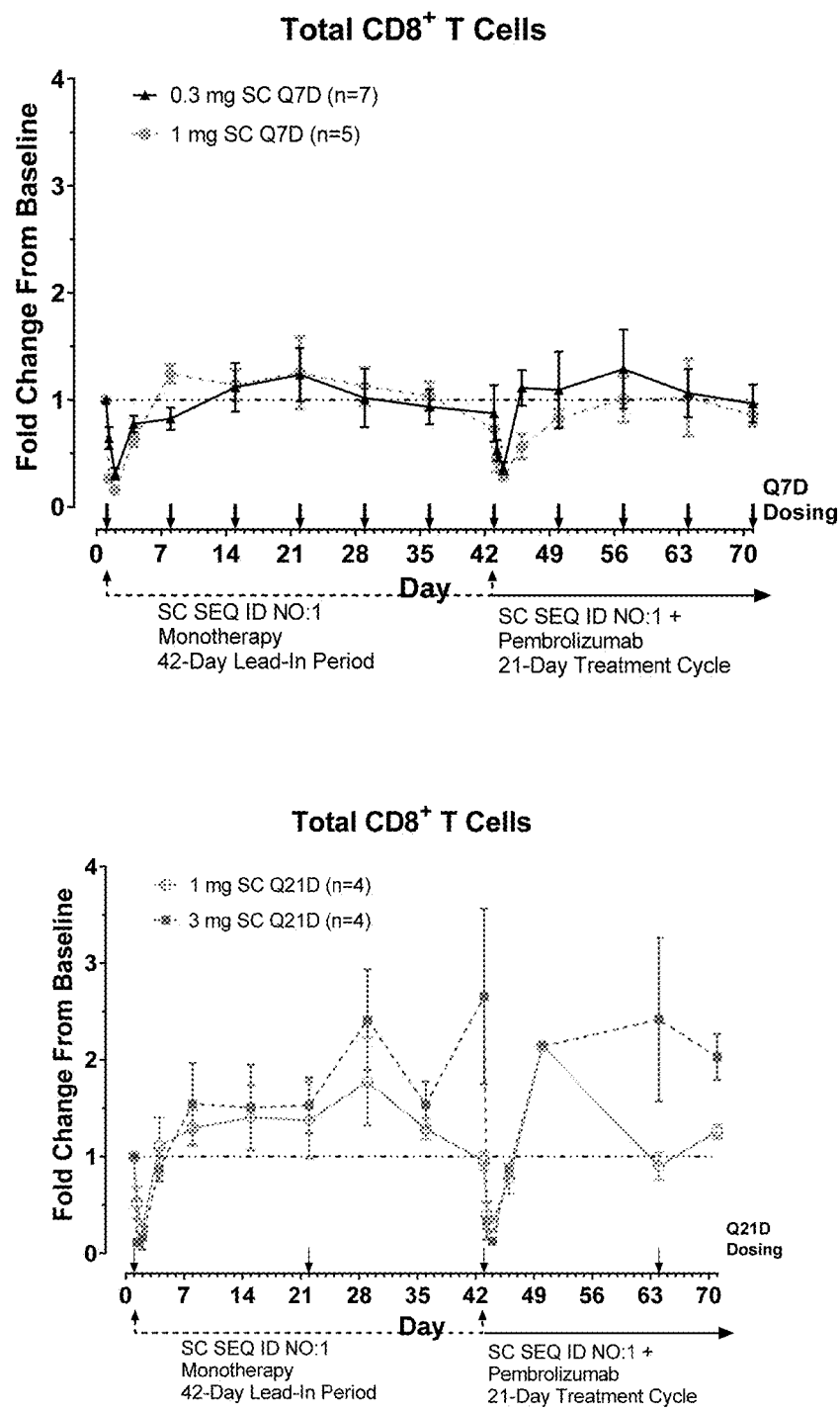
Figure 16:
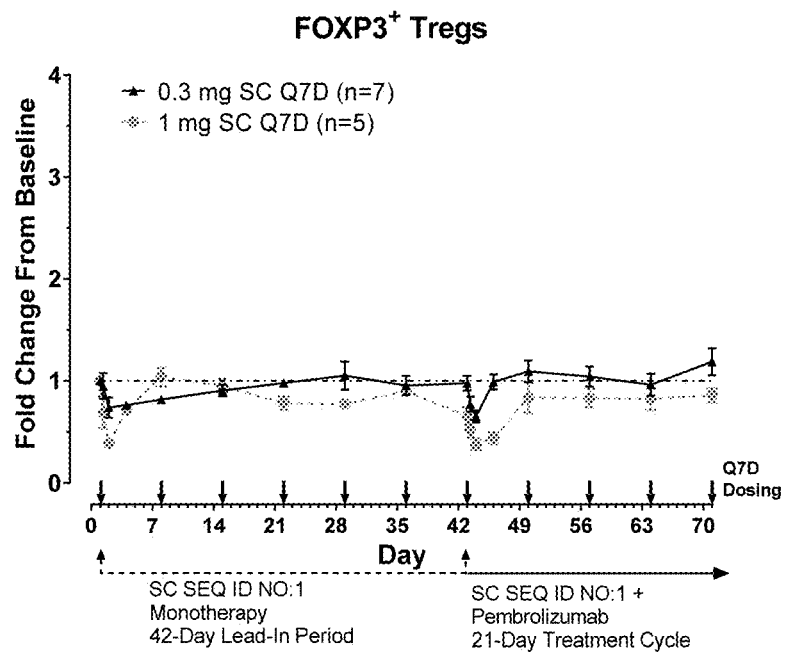
Figure 16:
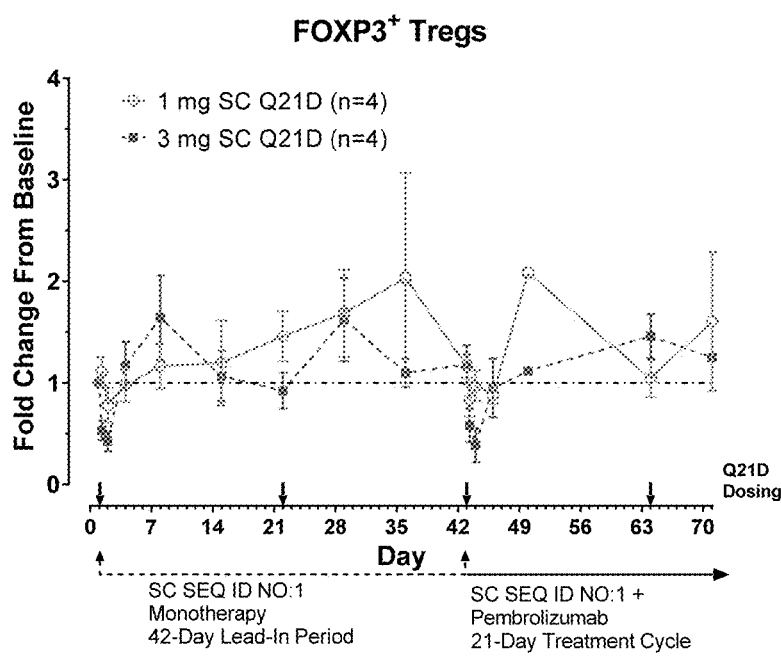

The time course of cell populations of total NK cells, total $CD8^+$ T cells and regulatory T cells ($T_{reg}$) in peripheral blood after SC administration of SEQ ID NO: 1 once every 7 days (Q7D) or once every 21 days (Q21D) are depicted in FIG. 15. The corresponding fold changes from baseline in total NK cells, total $CD8^+$ T cells and $T_{reg}$ are depicted in FIG. 16.

SEQ ID NO: 1 induced dose dependent increase in circulating NK and $CD8^+$ T cells with minimum effect on $T_{reg}$.

Figure 17:
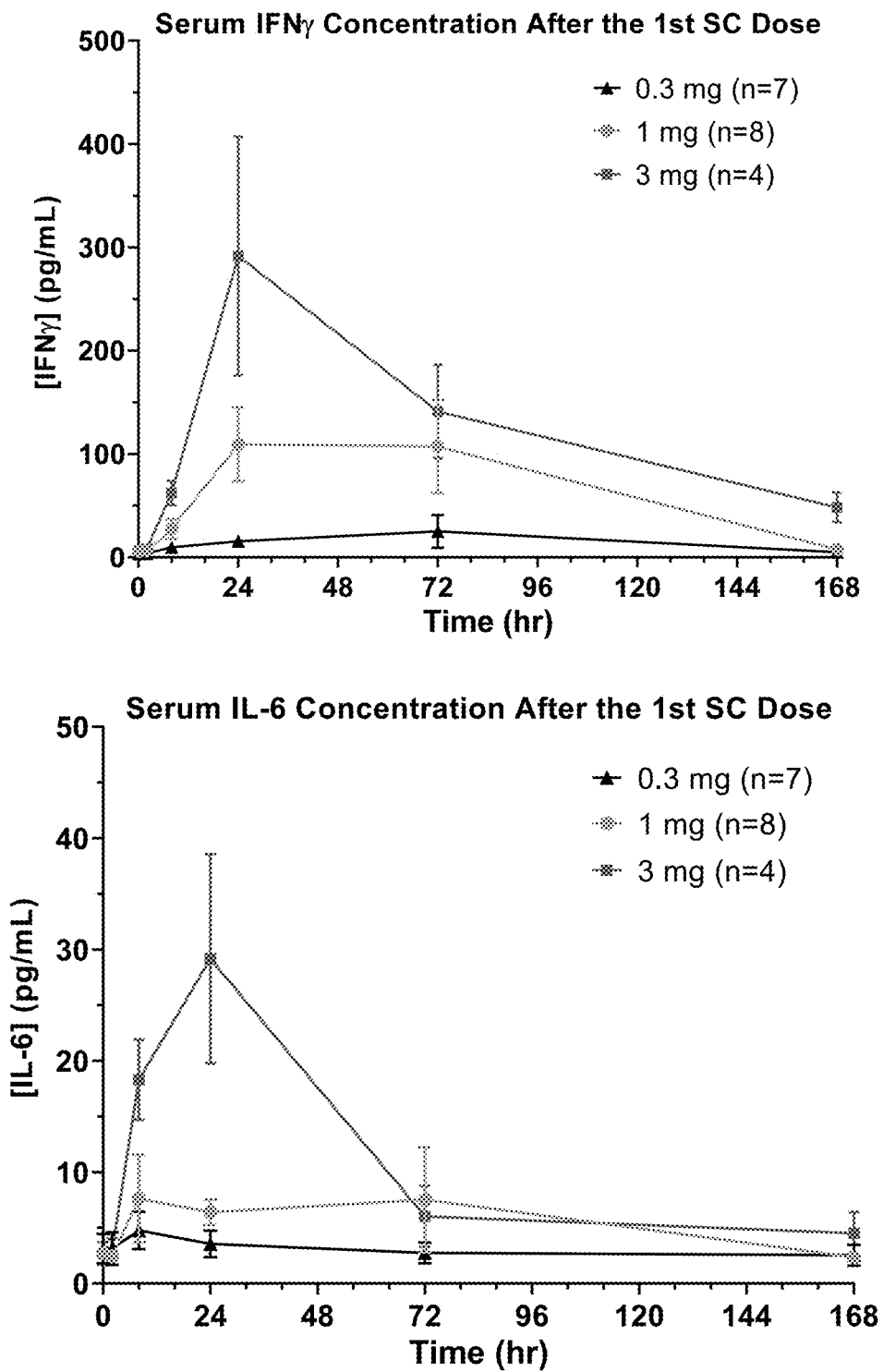
FIG. 17 are graphs comparing mean (±standard error) serum concentrations (pg/mL) of IFNγ and IL-6 in patients with advanced solid tumors after the first SC dose of SEQ ID NO: 1.

The serum concentration vs time profiles of interferon gamma (IFNγ) and IL-6 after the first SC dose of SEQ ID NO: 1 (monotherapy lead-in Cycle 1 Day 1) are depicted in FIG. 17.

Transient elevation of serum concentrations of IFNγ and IL-6 was observed after SC dosing, more pronounced at 3 mg. The peak IFNγ and IL-6 concentrations were observed at 24 hours post dose and returned toward baseline levels by 72 hours post dose. As discussed in Example 2, IFNγ is a pleiotropic cytokine with desirable anti-tumor and immunomodulatory properties. IL-6 on the other hand is a pro-inflammatory cytokine released by various cells in the tumor microenvironment including the cancerous cells. Down-regulation of IL-6 has been correlated with a better response to cancer treatment.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A method of treating cancer in a patient comprising periodically subcutaneously administering to the patient a dose of a fusion protein of SEQ ID NO: 1, or a fusion protein having a sequence identity of at least 80% over a contiguous sequence of at least about 20 amino acids up to the full length of SEQ ID NO: 1, wherein the periodic dosing is once every about 3 days to once every about 60 days.

2. The method of claim 1, wherein
the periodic dosing is once every about 3 days to once every about 21 days.

3. The method of claim 1, wherein periodic subcutaneous administration results in a greater increase in circulating CD8+ T cells in the patient as compared to daily subcutaneous administration.

4. The method of claim 1, wherein the cancer being treated is one or both of a solid tumor and a blood cancer.

5. The method of claim 1, wherein
the patient has a lower risk of T cell exhaustion relative to daily subcutaneous or intravenous administration.

6. The method of claim 1, further comprising co-administering to the patient a therapeutically effective amount of a therapeutic agent.

7. The method of claim 1, wherein the ratio of increase in IFNγ present in a patient's peripheral blood, serum or plasma resulting from subcutaneous administration is at least about 2-fold greater as compared to intravenous administration of an equivalent dose.

8. The method of claim 1, wherein the ratio of increase in IL-6 present in a patient's peripheral blood, serum or plasma when resulting from subcutaneous administration is at least about 2-fold less as compared to intravenous administration of an equivalent dose.

9. The method of claim 1, wherein the dose is provided as a pharmaceutical composition formulated for subcutaneous administration.

10. The method of claim 1, wherein periodic subcutaneous administration results in a greater ratio of CD8+ T cells to CD4+ $T_{regs}$ in the patient as compared to daily subcutaneous administration.

11. The method of claim 8, wherein the ratio of increase in IL-6 present in a patient's peripheral blood, serum or plasma resulting from subcutaneous administration is less than the ratio of increase in IFNγ.

12. The method of claim 1, further comprising repeating administration of the fusion protein of SEQ ID NO: 1 if the cancer reoccurs, or a new cancer develops in the patient.

13. The method of claim 1, wherein the method results a mean fold change from baseline in IFNγ present in a patient's peripheral blood, serum or plasma that is greater than the mean fold change from baseline in IL-6 present in a patient's peripheral blood, serum or plasma.

14. A method of treating small cell lung cancer (SCLC) in a patient comprising subcutaneously administering to the patient a dose of the fusion protein of SEQ ID NO: 1, or a fusion protein having a sequence identity of at least 80% over a contiguous sequence of at least about 20 amino acids up to the full length of SEQ ID NO: 1.

15. The method of claim 14, wherein the patient is periodically subcutaneously administered a dose of the fusion protein of SEQ ID NO: 1, or a fusion protein having a sequence identity of at least 80% over a contiguous sequence of at least about 20 amino acids up to the full length of SEQ ID NO: 1.

16. The method of claim 14, further comprising co-administering to the patient a therapeutically effective amount of a therapeutic agent.

17. A method of treating ovarian cancer in a patient comprising subcutaneously administering to the patient a dose of the fusion protein of SEQ ID NO: 1, or a fusion protein having a sequence identity of at least 80% over a contiguous sequence of at least about 20 amino acids up to the full length of SEQ ID NO: 1.

18. The method of claim 17, wherein the patient is periodically subcutaneously administered a dose of the fusion protein of SEQ ID NO: 1, or a fusion protein having a sequence identity of at least 80% over a contiguous sequence of at least about 20 amino acids up to the full length of SEQ ID NO: 1.

19. The method of claim 17, further comprising co-administering to the patient a therapeutically effective amount of a therapeutic agent.

20. The method of claim 2, wherein the periodic dosing is once every 3 days, once every 4 days, once every 14 days or once every 21 days.

21. The method of claim 2, wherein the periodic dosing is once every 7 days.

22. The method of claim 1, wherein the dose is about 0.1 mgs to about 30 mgs of the fusion protein of SEQ ID NO: 1.

23. The method of claim 22, wherein the dose is 1 mg, 3 mg, 6 mg, 10 mg, 15 mg, 20 mg or 30 mg.

24. The method of claim 22, wherein the dose is 3 mg.

25. The method of claim 1, wherein the dose is about 1 μg/kg to about 500 μg/kg.

26. The method of claim 1, wherein the dose is a corresponding fixed dose based on an about 60 to about 70 kg adult or based on an about 12 kg to about 50 kg or more child.

27. The method of claim 3, wherein the increase in circulating CD8+ T cells in the patient is at least 2-fold over baseline.

28. The method of claim 3, the ratio of increase of CD8+ T cells in the patient is greater than the ratio of increase in to CD4+ T regulatory cells ($T_{regs}$).

29. The method of claim 3, the ratio of increase in circulating CD8+ cells in the patient is greater than the ratio of increase in circulating CD4+ Treg cells.

30. The method of claim 4, wherein the solid tumor is a carcinoma, sarcoma or lymphoma.

31. The method of claim 4, wherein the size of the solid tumor is reduced.

32. The method of claim 4, wherein the blood cancer is leukemia, non-Hodgkin lymphoma, Hodgkin lymphoma and multiple myeloma.

33. The method of claim 1, wherein the cancer being treated is renal cell carcinoma (RCC), lymphomas, melanoma, hepatic cell carcinoma (HCC), non-small cell lung cancer (NSCLC), small cell lung cancer (SCLC), squamous cell carcinoma of the head and neck (SCCHN) breast cancer, pancreatic cancer, prostate cancer, colon and rectal cancer, bladder cancer, cervical cancer, thyroid cancer, esophageal cancer, oral cancer, mesothelioma, gastrointestinal cancer, ovarian cancer, and non-melanoma skin cancer.

34. The method of claim 1, wherein the patient has a lower risk of capillary leak syndrome (CLS) or cytokine release syndrome (CRS) relative to daily subcutaneous or intravenous administration.

35. The method of claim 1, wherein the patient has a lower risk of weight loss relative to daily subcutaneous or intravenous administration.

36. The method of claim 1, wherein the method results in at least a partial response in the patient.

37. The method of claim 6, wherein the therapeutic agent is a PARP inhibitor, a cytotoxic agent, a chemotherapeutic agent, or an immune checkpoint protein inhibitor.

38. The method of claim 37, wherein the immune checkpoint inhibitor inhibits the interaction of PD-1 and PD-L1.

39. The method of claim 37, wherein the immune checkpoint inhibitor is pembrolizumab.

40. The method of claim 39, wherein the pembrolizumab is co-administered prior to, simultaneously with, or subsequent to, administration of the fusion protein of SEQ ID NO:1.

41. The method of claim 1, wherein the ratio of increase in IFNγ present in a patient's peripheral blood, serum or plasma resulting from subcutaneous administration is at least about 5-fold greater as compared to intravenous administration of an equivalent dose.

42. The method of claim 1, wherein the ratio of increase in IFNγ present in a patient's peripheral blood, serum or plasma resulting from subcutaneous administration is about 2 fold to about 5 fold greater, as compared to intravenous administration of an equivalent dose.

43. The method of claim 40, wherein the pembrolizumab is co-administered in a separate composition from the fusion protein of SEQ ID NO: 1.

44. The method of claim 40, wherein the pembrolizumab is administered in an amount of 200 mg by I.V. injection or infusion.

45. The method of claim 40, wherein the pembrolizumab is administered on the first day of administration of the fusion protein of SEQ ID NO: 1.

46. The method of claim 40, wherein the pembrolizumab is administered about once a week or once every 3 weeks.

47. The method of claim 9, wherein the pharmaceutical composition is a stable aqueous solution ready for administration.

48. The method of claim 9, wherein the pharmaceutical composition is lyophilized.

49. The method of claim 48, wherein the lyophilized pharmaceutical composition is reconstituted with a pharmaceutically acceptable vehicle suitable for injection.

50. The method of claim 9, wherein the dose comprises about 1 mg to about 30 mg of the fusion protein of SEQ ID NO: 1.

51. The method of claim 15, wherein the periodic dosing is once every about 3 days to once every about 60 days.

52. The method of claim 16, wherein the therapeutic agent is a PARP inhibitor, a cytotoxic agent, a chemotherapeutic agent, or an immune checkpoint protein inhibitor.

53. The method of claim 52, wherein the immune checkpoint inhibitor inhibits the interaction of PD-1 and PD-L1.

54. The method of claim 52, wherein the immune checkpoint inhibitor is pembrolizumab.

55. The method of claim 18, wherein the periodic dosing is once every about 3 days to once every about 60 days.

56. The method of claim 19, wherein the therapeutic agent is a PARP inhibitor, a cytotoxic agent, a chemotherapeutic agent, or an immune checkpoint protein inhibitor.

57. The method of claim 56, wherein the immune checkpoint inhibitor inhibits the interaction of PD-1 and PD-L1.

58. The method of claim 56, wherein the immune checkpoint inhibitor is pembrolizumab.

* * * * *

SEQUENCE LISTING

```
<160> NUMBER OF SEQ ID NOS: 3

<210> SEQ ID NO 1
<211> LENGTH: 303
<212> TYPE: PRT
<213> ORGANISM: Artificial Sequence
<220> FEATURE:
<223> OTHER INFORMATION: Synthetic peptide

<400> SEQUENCE: 1

Ser Lys Asn Phe His Leu Arg Pro Arg Asp Leu Ile Ser Asn Ile Asn
1               5                   10                  15

Val Ile Val Leu Glu Leu Lys Gly Ser Glu Thr Thr Phe Met Cys Glu
            20                  25                  30

Tyr Ala Asp Glu Thr Ala Thr Ile Val Glu Phe Leu Asn Arg Trp Ile
        35                  40                  45

Thr Phe Ser Gln Ser Ile Ile Ser Thr Leu Thr Gly Gly Ser Ser Ser
```

```
                    50                  55                  60
Thr Lys Lys Thr Gln Leu Gln Leu Glu His Leu Leu Asp Leu Gln
 65                  70                  75                  80

Met Ile Leu Asn Gly Ile Asn Asn Tyr Lys Asn Pro Lys Leu Thr Arg
                     85                  90                  95

Met Leu Thr Phe Lys Phe Tyr Met Pro Lys Lys Ala Thr Glu Leu Lys
                    100                 105                 110

His Leu Gln Cys Leu Glu Glu Leu Lys Pro Leu Glu Glu Val Leu
                    115                 120                 125

Asn Leu Ala Gln Gly Ser Gly Gly Ser Glu Leu Cys Asp Asp Asp
            130                 135                 140

Pro Pro Glu Ile Pro His Ala Thr Phe Lys Ala Met Ala Tyr Lys Glu
145                 150                 155                 160

Gly Thr Met Leu Asn Cys Glu Cys Lys Arg Gly Phe Arg Arg Ile Lys
                    165                 170                 175

Ser Gly Ser Leu Tyr Met Leu Cys Thr Gly Asn Ser Ser His Ser Ser
                180                 185                 190

Trp Asp Asn Gln Cys Gln Cys Thr Ser Ser Ala Thr Arg Asn Thr Thr
                195                 200                 205

Lys Gln Val Thr Pro Gln Pro Glu Glu Gln Lys Glu Arg Lys Thr Thr
            210                 215                 220

Glu Met Gln Ser Pro Met Gln Pro Val Asp Gln Ala Ser Leu Pro Gly
225                 230                 235                 240

His Cys Arg Glu Pro Pro Pro Trp Glu Asn Glu Ala Thr Glu Arg Ile
                245                 250                 255

Tyr His Phe Val Val Gly Gln Met Val Tyr Tyr Gln Cys Val Gln Gly
                260                 265                 270

Tyr Arg Ala Leu His Arg Gly Pro Ala Glu Ser Val Cys Lys Met Thr
                275                 280                 285

His Gly Lys Thr Arg Trp Thr Gln Pro Gln Leu Ile Cys Thr Gly
            290                 295                 300

<210> SEQ ID NO 2
<211> LENGTH: 309
<212> TYPE: PRT
<213> ORGANISM: Artificial Sequence
<220> FEATURE:
<223> OTHER INFORMATION: Synthetic peptide

<400> SEQUENCE: 2

Ser Lys Ser Phe Gln Leu Glu Asp Ala Glu Asn Phe Ile Ser Asn Ile
 1               5                  10                  15

Arg Val Thr Val Val Lys Leu Lys Gly Ser Asp Asn Thr Phe Glu Cys
                20                  25                  30

Gln Phe Asp Asp Glu Ser Ala Thr Val Val Asp Phe Leu Arg Arg Trp
            35                  40                  45

Ile Ala Phe Cys Gln Ser Ile Ile Ser Thr Ser Pro Gln Gly Gly Ser
        50                  55                  60

Ser Ser Thr Gln Gln Gln Gln Gln His Leu Glu Gln Leu Leu Met Asp
 65                  70                  75                  80

Leu Gln Glu Leu Leu Ser Arg Met Glu Asn Tyr Arg Asn Leu Lys Leu
                85                  90                  95

Pro Arg Met Leu Thr Phe Lys Phe Tyr Leu Pro Lys Gln Ala Thr Glu
                100                 105                 110

Leu Lys Asp Leu Gln Cys Leu Glu Asp Glu Leu Gly Pro Leu Arg His
```

-continued

```
                  115                 120                 125
Val Leu Asp Leu Thr Gln Gly Ser Gly Gly Ser Glu Leu Cys Leu
            130                 135                 140

Tyr Asp Pro Pro Glu Val Pro Asn Ala Thr Phe Lys Ala Leu Ser Tyr
145                 150                 155                 160

Lys Asn Gly Thr Ile Leu Asn Cys Glu Cys Lys Arg Gly Phe Arg Arg
                165                 170                 175

Leu Lys Glu Leu Val Tyr Met Arg Cys Leu Gly Asn Ser Trp Ser Ser
            180                 185                 190

Asn Cys Gln Cys Thr Ser Asn Ser His Asp Lys Ser Arg Lys Gln Val
            195                 200                 205

Thr Ala Gln Leu Glu His Gln Lys Glu Gln Gln Thr Thr Thr Asp Met
        210                 215                 220

Gln Lys Pro Thr Gln Ser Met His Gln Glu Asn Leu Thr Gly His Cys
225                 230                 235                 240

Arg Glu Pro Pro Pro Trp Lys His Glu Asp Ser Lys Arg Ile Tyr His
                245                 250                 255

Phe Val Glu Gly Gln Ser Val His Tyr Glu Cys Ile Pro Gly Tyr Lys
            260                 265                 270

Ala Leu Gln Arg Gly Pro Ala Ile Ser Ile Cys Lys Met Lys Cys Gly
        275                 280                 285

Lys Thr Gly Trp Thr Gln Pro Gln Leu Thr Cys Val Asp Gly Ser His
    290                 295                 300

His His His His His
305

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Met Tyr Arg Met Gln Leu Leu Ser Cys Ile Ala Leu Ser Leu Ala Leu
1               5                   10                  15

Val Thr Asn Ser
            20
```